United States Patent
Waldman et al.

(10) Patent No.: US 12,005,220 B2
(45) Date of Patent: Jun. 11, 2024

(54) MICRONEEDLE PATCH FOR IMMUNOSTIMULATORY DRUG DELIVERY

(71) Applicant: VERADERMICS INCORPORATED, San Antonio, TX (US)

(72) Inventors: Reid Waldman, West Hartford, CT (US); Madeline DeWane, Hamden, CT (US); Ming Hua Lee, Chicago, IL (US); Lauren Sweeney Durso, Washington, DC (US)

(73) Assignee: Veradermics Incorporated, West Hartford, CT (US)

( * ) Notice: Subject to any disclaimer, the term of this patent is extended or adjusted under 35 U.S.C. 154(b) by 596 days.

(21) Appl. No.: 17/100,722

(22) Filed: Nov. 20, 2020

(65) Prior Publication Data

US 2021/0154456 A1    May 27, 2021

Related U.S. Application Data

(60) Provisional application No. 62/939,447, filed on Nov. 22, 2019.

(51) Int. Cl.
*A61M 37/00* (2006.01)
*A61K 39/00* (2006.01)
*A61K 39/12* (2006.01)

(52) U.S. Cl.
CPC ..... *A61M 37/0015* (2013.01); *A61K 39/0002* (2013.01); *A61K 39/12* (2013.01); *A61K 2039/55555* (2013.01); *A61M 2037/0023* (2013.01); *A61M 2037/0061* (2013.01)

(58) Field of Classification Search
CPC ...... A61M 37/0015; A61M 2037/0023; A61M 2037/0061; A61M 2037/0046; A61K 39/0002; A61K 39/12; A61K 2039/55555; A61K 39/35; A61B 17/205
See application file for complete search history.

(56) References Cited

U.S. PATENT DOCUMENTS

| | | | |
|---|---|---|---|
| 6,835,184 B1 | 12/2004 | Sage et al. |
| 7,108,681 B2 | 9/2006 | Gartstein et al. |
| 8,603,384 B2 | 12/2013 | Luttge et al. |
| 9,180,173 B2 | 11/2015 | Neider |
| 9,459,746 B2 | 10/2016 | Rosenberg et al. |
| 9,549,746 B2 | 1/2017 | Woolfson et al. |
| 9,550,053 B2 | 1/2017 | Ross |
| 10,322,272 B2 | 6/2019 | Pettis et al. |

(Continued)

FOREIGN PATENT DOCUMENTS

| | | |
|---|---|---|
| CN | 109701152 A | 5/2019 |
| EP | 3281627 A1 | 2/2018 |

(Continued)

OTHER PUBLICATIONS

International Search Report and Written Opinion for PCT/US2020/061667 dated Feb. 25, 2021.

(Continued)

*Primary Examiner* — Amber R Stiles
(74) *Attorney, Agent, or Firm* — DLA Piper LLP

(57) ABSTRACT

The application provides a dissolvable microneedle device to deliver immune stimulants to the skin. The application also provides a method of treating a skin condition comprising applying a dissolvable microneedle device to the skin.

30 Claims, 14 Drawing Sheets

(56) References Cited

U.S. PATENT DOCUMENTS

| | | |
|---|---|---|
| 10,398,885 B2 | 9/2019 | Frits et al. |
| 2004/0106904 A1 | 6/2004 | Gonnelli et al. |
| 2005/0175634 A1 | 8/2005 | Hom et al. |
| 2007/0275045 A1* | 11/2007 | Evans .................. A61K 9/0034 |
| | | 424/449 |
| 2008/0009811 A1* | 1/2008 | Cantor .............. A61M 37/0015 |
| | | 604/272 |
| 2009/0182306 A1* | 7/2009 | Lee ......................... B29C 41/04 |
| | | 604/506 |
| 2011/0245776 A1* | 10/2011 | Kendall ............... A61B 17/205 |
| | | 604/173 |
| 2012/0045413 A1 | 2/2012 | Nakagawa et al. |
| 2012/0130306 A1* | 5/2012 | Terahara .............. A61K 9/0021 |
| | | 604/46 |
| 2014/0005606 A1 | 1/2014 | Chen et al. |
| 2015/0080802 A1* | 3/2015 | Kang ................ A61M 37/0015 |
| | | 604/173 |
| 2016/0120799 A1* | 5/2016 | Chiang .................. A61K 39/12 |
| | | 424/224.1 |
| 2016/0220843 A1 | 8/2016 | Iwata |
| 2017/0196966 A1 | 7/2017 | Henderson |
| 2018/0078498 A1 | 3/2018 | Petersson et al. |
| 2018/0177990 A1* | 6/2018 | Alary .................. A61M 37/0015 |
| 2018/0229017 A1 | 8/2018 | Schwab et al. |
| 2018/0236215 A1 | 8/2018 | Liu et al. |

FOREIGN PATENT DOCUMENTS

| | | |
|---|---|---|
| JP | 2012504160 A | 2/2012 |
| JP | 2016087474 A | 5/2016 |
| WO | 2015149031 A1 | 10/2015 |
| WO | 2017085248 A1 | 5/2017 |
| WO | 2017151727 A1 | 9/2017 |
| WO | 2019135717 A1 | 7/2019 |
| WO | 2019200081 A1 | 10/2019 |
| WO | 2020002905 A1 | 1/2020 |
| WO | 2020033329 A1 | 2/2020 |
| WO | 2022204255 A1 | 9/2022 |

OTHER PUBLICATIONS

International Search Report and Written Opinion for PCT/US2022/030235 dated Oct. 6, 2022.

Majid et al., "Immunotherapy with Intralesional Candida Albicans Antigen in Resistant or Recurrent Warts: A Study," Indian Journal of Dermatology, Sep.-Oct. 2013;58(5): pp. 360-365.

Nofal et al., "Significance of Interferon Gamma in the Prediction of Successful Therapy of Common Warts by Intralesional Injection of Candida Antigen," International Journal of Dermatology, Aug. 8, 2017; vol. 56, Issue 10; 3 pages.

Nofal et al., "Intralesional Candida Antigen Versus Intralesional Tuberculin in the Treatment of Recalcitrant Genital Warts: A Comparative Study," Mendeley Data, Version 2; Jan. 31, 2020.

Phillips et al., "Treatment of Warts with Candida Antigen Injection," Archives of Dermatology, Oct. 2001, 7 pages.

Nassar et al., "Candida Antigen Immunotherapy for Treatment of Cutaneous Warts: A One-Year Zagazig University—Dermatology Clinic Experience," Articles in Press, Oct. 21, 2019.

Demuth, "Engineered Microneedles for Transcutaneous Vaccine Delivery," Department of Biological Engineering, Massachusetts Institute of Technology, Mar. 12, 2013; 165 pages.

Ye et al., "Polymeric Microneedles for Transdermal Protein Delivery," Adv Drug Dellv Rev., Jun. 27, 2018; 30 pages.

International Search Report and Written Opinion for PCT/US2022/021503 dated Jun. 14, 2022.

* cited by examiner

MICRONEEDLE PATCH FOR IMMUNOSTIMULATORY DRUG DELIVERY

CROSS-REFERENCE TO RELATED APPLICATIONS

This application claims benefit of priority to U.S. Provisional Application No. 62/939,447 entitled "Microneedle Patch for Immunostimulatory Drug Delivery," filed Nov. 22, 2019, which is incorporated herein by reference in its entirety.

TECHNICAL FIELD

The present application generally relates to a microneedle patch composition capable of delivering immediate as well as sustained release of therapeutically active ingredients for local immune stimulation. More specifically, the present application relates to microneedle compositions for stimulating a local immune response using immediate and/or sustained release microneedles intended for the treatment of skin conditions.

BACKGROUND

At first glance, transdermal drug delivery appears to be an attractive route of drug administration because the skin has a large surface area and is relatively, accessible allowing for drugs to be applied directly to areas affected by skin diseases. However, in practice, transdermal drug delivery is not a suitable route of administration for many therapeutic active ingredients because the skin serves as a protective barrier that keeps these ingredients from reaching clinically meaningful concentrations within the epidermis and dermis.

The skin's ability to serve as a barrier to effective drug delivery is predominately attributed to the lipid-rich outer layer of the epidermis called the stratum corneum. The lipids contained within the stratum corneum prevent transit of hydrophilic molecules across the skin barrier. Additionally, tight junctions between cells in the epidermis (e.g. adherens junctions, desmosomes, and zonula occludens) prevent substances greater than 500 kilodaltons in size from penetrating through the skin. Resultantly, the large immunogenic proteins and peptides that comprise the class of cutaneous immunotherapy cannot reliably be administered into skin using traditional preparations.

There have been many attempts to facilitate transdermal drug delivery of large substances like cutaneous immune stimulants through several methods. These include addition of chemical penetration enhancers such as ethanol, propylene glycol, and hydrophobic vesicles to topical formulations, cell membrane polarization through the use of iontophoresis, and mechanical delivery using cavitation ultrasound. Unfortunately, these methods for augmenting transdermal drug delivery have two major pitfalls. They are either too toxic to underlying tissues to allow routine clinical use and/or they are too burdensome to patients because of cosmetic unacceptability (i.e. preparations containing chemical enhancers are greasy) or need for cumbersome equipment (e.g. cavitation ultrasound, iontophoresis).

Microneedles are another drug delivery approach that have been used to deliver drugs into the epidermis and/or dermis. Microneedles create micron sized pathways or channels in the skin that allow for drugs to be directly delivered to the desired depth within the epidermis and/or dermis where they can enact their desired function. One subtype of microneedles, dissolving microneedles, are composed entirely of degradable polymer complexed with active ingredient. Thus, when they are inserted into the skin, they are completely consumed during the process of dissolution.

Microneedles used for treatment of skin diseases currently deliver active ingredients that are immune suppressors (e.g. corticosteroids, calcipotriene, antibiotics) or chemotherapeutic agents (e.g. bleomycin, doxorubicin). Despite more than 40 years of microneedle research, microneedles have not been used to deliver cutaneous immune stimulators for the purposes of creating a local immune response to treat skin disease.

One grouping of skin conditions that would benefit from finely tuned administration of immune stimulants into the skin are infectious and malignant neoplasms such as viral warts, molluscum contagiosum, and non-melanoma skin cancer. These conditions are not adequately treated by microneedles containing immune suppressors or chemotherapy for several reasons. Principally, these neoplasms vary in size and shape, even between lesions occurring on the same patient. Treating these neoplasms with immune suppressors or chemotherapy would require providing a patient with microneedle patches that are the exact size of each neoplasm that the patient has. The reason these drug classes need to be administered using exactly sized microneedle patches is to allow for the drug to reach all neoplastic cells while simultaneously minimizing damage to surrounding cells. The creation of numerous sizes of microneedle patches as would be required for these types of ingredients is impractical from a manufacturing standpoint and has thus limited the limited the use of immune suppressor and chemotherapeutic microneedles in the treatment skin disease. Furthermore, these types of neoplasms often present with multiple skin lesions arising on the same patient. Treating neoplasms with microneedles comprised of immune suppressors or local chemotherapy would require applying a microneedle patch to each individual neoplasm which is burdensome from a clinical administration standpoint.

One condition in particular that would benefit from finetuned delivery of immune stimulants into the skin is viral warts. Viral warts are exceptionally common affecting nearly 20% of school aged children. Unfortunately, currently available treatments for warts are: 1) painful; 2) ineffective; 3) leave scars; 4) require daily applications for months at a time; and/or 5) scare children. These treatments include treatments that are used to destroy wart tissue (e.g. cryotherapy with liquid nitrogen, cantharidin), topical preparations containing salicylic acid that break down the adhesions between cells comprising a wart, and immune stimulants that are applied topically or injected into a wart. Destructive wart treatments are painful, create open wounds in the skin, and may leave behind permanent scars. Salicylic acidcontaining products must be applied under occlusion daily and worn around the clock for several months at a time limiting real world adherence to treatment as well as treatment efficacy.

Cutaneous immunotherapy is a type of wart treatment where immune stimulants are either applied topically to the wart or injected into the wart to create a localized immune response that recognizes and destroys the wart's causative viral infection. Use of immunotherapy in clinical practice is limited by problems with current formulations: creams and injectable solutions. Topical application of creams requires burdensome and time-consuming patient adherence with daily application of the cream for up to several months at a time. The reason that immunotherapy creams require so many applications to be efficacious is because the stratum corneum limits penetration of the topically applied immunotherapy active ingredient into the skin. Injectable immune stimulators require less frequent administration than topical preparations because injection bypasses the stratum corneum. However, the use of injectable immune stimulators is limited by the pain associated with injection and because injectable immune stimulators cannot be reliably placed in the epidermis because intercellular junctions prevent liquid volume expansion within the epidermis. Furthermore, because injections of immune stimulators into warts have to be performed by experienced medical providers, their use requires patients to have medical appointments every 2-4 weeks to be treated. The need for frequent medical office visits places time constraints on patients and medical providers alike and decreases the rate of completed treatment courses.

Creation of the first-ever cutaneous immunotherapy-containing dissolving microneedles addresses current limitations in cutaneous immunotherapy delivery by allowing for precise delivery of immune stimulants into the epidermis and dermis where key immune effector cells, Langerhans cells and dermal dendritic cells, respectively, reside. Not only does this invention allow for painless and precise delivery of cutaneous immune stimulants into the skin to treat skin diseases, but also it is the only cutaneous immunotherapy formulation that allows for sustained release of immune stimulants creating controlled and continuous immune stimulation.

SUMMARY

Embodiments of the application are directed to a dissolvable microneedle patch for delivery of a therapeutically active ingredient to the skin comprising a plurality of microneedles comprising microneedles of at least two different lengths; and a removable substrate; wherein the plurality of microneedles are attached to the removable substrate; wherein the plurality of microneedles comprise a tapered tip that extends away from the removal substrate; wherein the plurality of microneedles comprise a biodegradable polymer and a therapeutically active ingredient dispersed in the biodegradable polymer; and wherein the active ingredient is selected from the group consisting of a vaccine, an immune stimulating molecule, an immune stimulating organism, and an immune stimulating protein.

Embodiments of the present application are directed to a method of treating a skin condition comprising i) applying a dissolvable microneedle patch for delivery of the therapeutically active ingredient to the skin comprising a plurality of microneedles comprising microneedles of at least two different lengths; and a removable substrate; wherein the plurality of microneedles are attached to the removable substrate; wherein the plurality of microneedles comprise a tapered tip that extends away from the removal substrate; wherein the plurality of microneedles comprise a biodegradable polymer and a therapeutically active ingredient dispersed in the biodegradable polymer; and wherein the active ingredient is selected from the group consisting of a vaccine, an immune stimulating molecule, an immune stimulating organism, and an immune stimulating protein; and ii) exerting sufficient force on the dissolvable microneedle patch to permit the microneedles to penetrate to a location selected from the group consisting of the epidermis, the dermis, and the papillary dermis; and iii) allowing the plurality of microneedles to remain in the skin until the biodegradable polymer degrades and iv) removing adhesive substrate from the patch composition.

BRIEF DESCRIPTION OF THE DRAWINGS

The accompanying drawings, which are incorporated in and form a part of the specification, illustrate the embodiments of the application and together with the written description serve to explain the principles, characteristics, and features of the invention. In the drawings.

DETAILED DESCRIPTION

Figure 1:
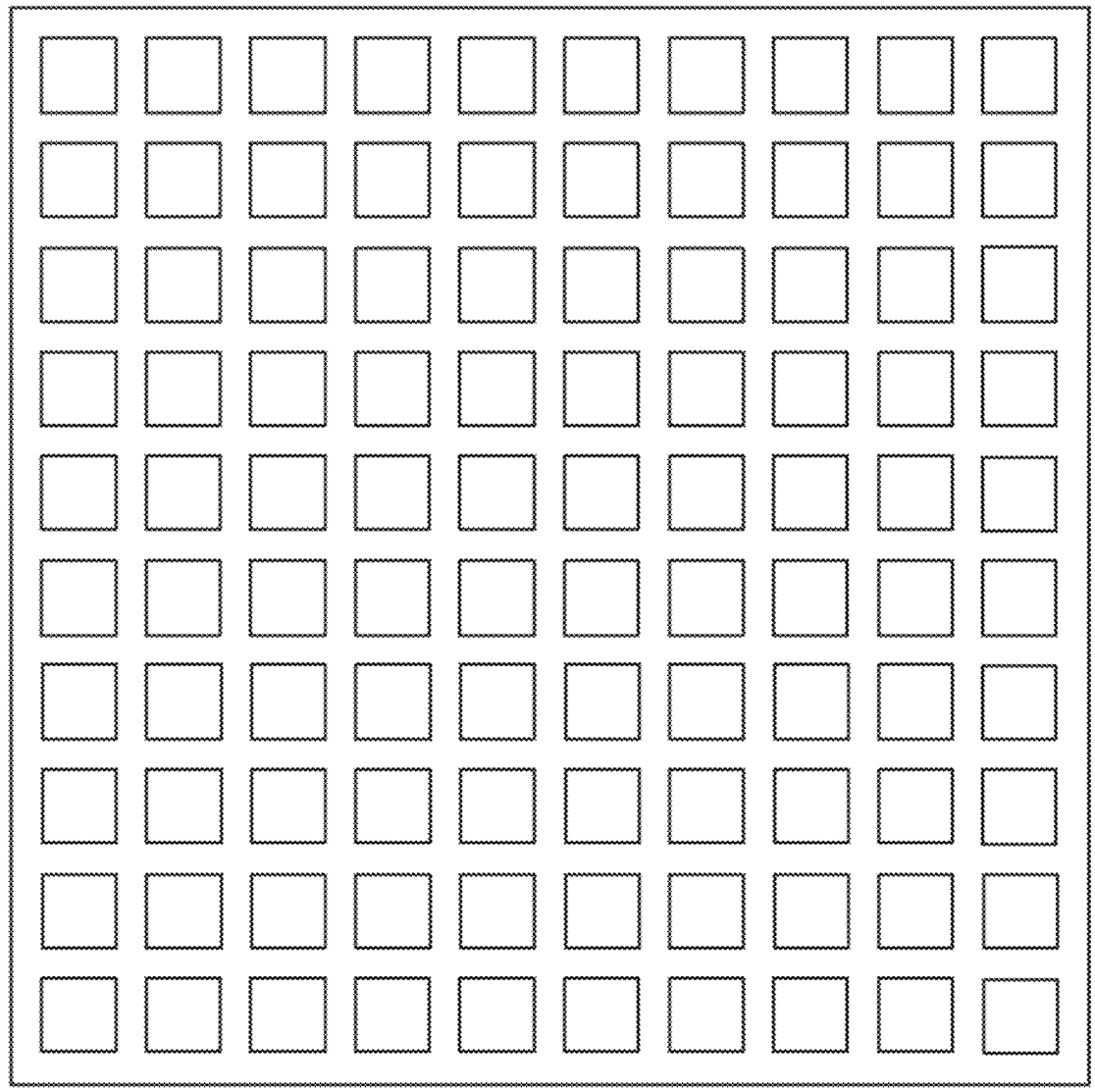
FIG. 1 is an illustration of the microneedle patch of the present application as viewed from the top, if the adhesive were translucent, to show the pyramidal needles below.

This disclosure is not limited to the particular systems, devices and methods described, as these may vary. The terminology used in the description is for the purpose of describing the particular versions or embodiments only, and is not intended to limit the scope. Such aspects of the disclosure be embodied in many different forms; rather, these embodiments are provided so that this disclosure will be thorough and complete, and will fully convey its scope to those skilled in the art.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

All percentages, parts and ratios are based upon the total weight of the compositions and all measurements made are at about 25° C., unless otherwise specified.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art. Where the context of the disclosure indicates otherwise, or is inconsistent with such an interpretation, the above-stated interpretation may be modified as would be readily apparent to a person skilled in the art. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The term "substantially free" as used herein indicates that a specified substance referred to is present in amounts not more than 10% by weight or volume of the total composition.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "animal" as used herein includes, but is not limited to, humans and non-human vertebrates such as wild, domestic, and farm animals.

The term "tissue" refers to any aggregation of similarly specialized cells which are united in the performance of a particular function.

The term "disorder" is used in this disclosure to mean, and is used interchangeably with, the terms disease, condition, or illness, unless otherwise indicated.

The term "wart" as used herein refers to a small, hard, benign growth on the skin, caused by a virus.

The terms "administer," "administering" or "administration" as used herein refer to either directly administering a compound (also referred to as an agent of interest) or pharmaceutically acceptable salt of the compound (agent of interest) or a composition to a subject.

The term "treat," "treated," or "treating" as used herein refers to both therapeutic treatment and prophylactic or preventative measures, wherein the object is to reduce the frequency of, or delay the onset of, symptoms of a medical condition, enhance the texture, appearance, color, sensation, or hydration of the intended tissue treatment area of the tissue surface in a subject relative to a subject not receiving the compound or composition, or to otherwise obtain beneficial or desired clinical results. For the purposes of this invention, beneficial or desired clinical results include, but are not limited to, reversal, reduction, or alleviation of symptoms of a condition; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

In some embodiments, the compounds and methods disclosed herein can be utilized with or on a subject in need of such treatment, which can also be referred to as "in need thereof." As used herein, the phrase "in need thereof" means that the subject has been identified as having a need for the particular method or treatment and that the treatment has been given to the subject for that particular purpose.

As used herein, the term "therapeutic" or "therapeutic agent" or "pharmaceutically active agent" means an agent utilized to treat, combat, ameliorate, prevent or improve an unwanted condition or disease of a patient.

The term "composition" as used herein refers to a combination or a mixture of two or more different ingredients, components, or substances.

The term "immune stimulator" as used herein refers to an external source that activates the immune system. An immune stimulator can come from multiple sources such as immunogenic antigens including *Candida* antigen, *Trichophyton* antigen, and tuberculin, immunogenic organisms including *Corynebacterium parvum, Cutibacterium acnes*, and *Mycobacterium indicus pranii* (formerly *Mycobacterium w*), immunogenic molecules such as imiquimod, and immunogenic vaccines such as human papillomavirus vaccine, measles-mumps-rubella vaccine, mumps vaccine, *Bacillus* Calmette-Guérin vaccine, and the *Mycobacterium w* vaccine.

The phrase "therapeutically effective" is intended to qualify the amount of active ingredients (i.e, the compounds or derivatives thereof) used in the treatment of a disease or disorder or on the effecting of a clinical endpoint.

A "therapeutically effective amount" or "effective amount" of a compound or composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The term "inhibiting" includes the administration of a compound of the present invention to prevent the onset of the symptoms, alleviating the symptoms, reducing the symptoms, delaying or decreasing the progression of the disease and/or its symptoms, or eliminating the disease, condition or disorder.

As used herein, the phrase "essentially no therapeutically active ingredient" refers to an amount of therapeutically active ingredient that would not lead to a physiological response. "Essentially no therapeutically active ingredient" may be defined as about 10% or less of therapeutically active ingredient.

The term "excipients" as used herein encompasses carriers and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum spinosum.

The terms "topically" and "topical" as used herein refer to application of the compositions to the surface of the skin, mucosal cells, keratins and tissues. Examples of keratins are nails and hair.

The term "skin: as used herein refers to the thin layer of tissue forming the natural outer covering of the body of a person or animal. The skin is made of the epidermis and dermis. As used herein, the stratum corneum is the outermost layer of the epidermis and the papillary dermis is the uppermost layer of the dermis.

The term "immediate release" as used herein refers to polymers designed to release at least 75% of the therapeutically active ingredients on a timescale of about 0 hours to about 24 hours.

The term "sustained release" as used herein refers to polymers that do not release more than 75% of the therapeutically active ingredients until a time greater than about 24 hours after application.

The term "biodegradable polymer" as used herein refers to a polymer that breaks down or dissolved after introduction to the skin and release of the therapeutically active ingredient.

The term "sufficient force" as used herein refers to the force required to apply the microneedle patch so that the microneedles penetrate the skin to the desired depth.

The term "sensitization" as used herein refers to the administration of the therapeutic agent or stimulant to prime the immune system for the purpose of obtaining a more robust response upon subsequent administration.

The term "hypersensitivity" as used herein refers to undesirable reactions produced by the normal immune system, including allergies and autoimmunity.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, structures, or groups thereof, or any members of a claimed group, less than the full measure of this disclosure can be claimed for any reason. Throughout this disclosure, various patents, patent applications and publications are referenced. The disclosures of these patents, patent applications and publications are incorporated into this disclosure by reference in their entireties in order to more fully describe the state of the art as known to those skilled therein as of the date of this disclosure. This disclosure will govern in the instance that there is any inconsistency between the patents, patent applications and publications cited and this disclosure.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

Dissolvable Microneedle Patch

Embodiments of the application are directed to a dissolvable microneedle patch for delivery of a therapeutically active ingredient to the skin. The microneedle patch comprising a plurality of microneedles comprising microneedles of at least two different lengths and a removable substrate, wherein the plurality of microneedles are attached to the removable substrate. The plurality of microneedles comprise a tapered tip that extends away from the removable substrate. The plurality of microneedles comprise a biodegradable polymer and a therapeutically active ingredient dispersed in the biodegradable polymer. The therapeutically active ingredient is selected from the group consisting of a vaccine, and immune stimulating molecule, an immune stimulating organism, and an immune-stimulating protein.

In some embodiments, the dissolvable microneedle patch comprises a plurality of microneedles wherein the at least two different lengths are selected from the group consisting of a length to terminate in the epidermis and a length to terminate in the reticular or papillary dermis. In some embodiments, the dissolvable microneedle patch comprises a plurality of microneedles with one to five different lengths. In some embodiments, the dissolvable microneedle patch comprises a plurality of microneedles wherein the at least two varying lengths may be different based on the location on the body, patient age, or the skin condition to be treated. In some embodiments, the needles of at least two different lengths are of equal proportion. In some embodiments, the needles of at least two different lengths can be of different proportions. In an alternate embodiment, the dissolvable microneedle patch comprises a plurality of microneedles wherein the microneedles are of a single length. In some embodiments, the dissolvable microneedle patch comprises a plurality of microneedles wherein the microneedles are of equal lengths. In some embodiments, the dissolvable microneedle patch comprises a plurality of microneedles wherein the at least two varying lengths range from about 10 microns to about 1000 microns, about 10 microns to about 900 microns, about 10 microns to about 800 microns, about 10 microns to about 700 microns, about 10 microns to about 600 microns, about 10 microns to about 500 microns, about 10 microns to about 400 microns, about 10 microns to about 300 microns, about 10 microns to about 200 microns, about 10 microns to about 100 microns, about 10 microns to about 90 microns, about 10 microns to about 80 microns, about 10 microns to about 70 microns, about 10 microns to about 60 microns, about 10 microns to about 50 microns, about 10 microns to about 40 microns, about 10 microns to about 30 microns, about 10 microns to about 20 microns, about 10 microns to about 15 microns, about 20 microns to about 1000 microns, about 20 microns to about 900 microns, about 20 microns to about 800 microns, about 20 microns to about 700 microns, about 20 microns to about 600 microns, about 20 microns to about 500 microns, about 20 microns to about 400 microns, about 20 microns to about 300 microns, about 20 microns to about 200 microns, about 20 microns to about 100 microns, about 20 microns to about 90 microns, about 20 microns to about 80 microns, about 20 microns to about 70 microns, about 20 microns to about 60 microns, about 20 microns to about 50 microns, about 20 microns to about 40 microns, about 20 microns to about 30 microns, about 20 microns to about 25 microns, about 50 microns to about 1000 microns, about 50 microns to about 900 microns, about 50 microns to about 800 microns, about 50 microns to about 700 microns, about 50 microns to about 600 microns, about 50 microns to about 500 microns, about 50 microns to about 400 microns, about 50 microns to about 300 microns, about 50 microns to about 200 microns, about 50 microns to about 100 microns, about 100 microns to about 1000 microns, about 100 microns to about 900 microns, about 100 microns to about 800 microns, about 100 microns to about 700 microns, about 100 microns to about 600 microns, about 100 microns to about 500 microns, about 100 microns to about 400 microns, about 100 microns to about 300 microns, about 100 microns to about 200 microns, about 200 microns to about 1000 microns, about 200 microns to about 900 microns, about 200 microns to about 800 microns, about 200 microns to about 700 microns, about 200 microns to about 600 microns, about 200 microns to about 500 microns, about 200 microns to about 400 microns, about 200 microns to about 300 microns, about 500 microns to about 1000 microns, about 500 microns to about 900 microns, about 500 microns to about 800 microns, about 500 microns to about 700 microns, about 500 microns to about 600 microns, about 800 microns to about 1000 microns, about 800 microns to about 900 microns, about 900 microns to about 1000 microns, or a value within these ranges In some embodiments, the dissolvable microneedle patch comprises a plurality of microneedles wherein the microneedles are tapered to a point to facilitate the insertion of the microneedles into the skin. In some embodiments, the dissolvable microneedle patch comprises a plurality of microneedles wherein the microneedles have a tapered tip portion containing a therapeutically active ingredient dispersed in a matrix or suspension of a biodegradable polymer.

In some embodiments, the dissolvable microneedle patch comprises a plurality of microneedles comprising microneedles of at least two different lengths are composed of equal volumes of biodegradable polymer. In some embodiments, the dissolvable microneedle patch comprises a plurality of microneedles wherein the volume of each microneedle may remain constant which is achieved by changing the diameter of each of the microneedles as required. In some embodiments, the dissolvable microneedle patch comprises a plurality of microneedles wherein the volume of each microneedle is unequal. In some embodiments, the dissolvable microneedle patch comprises a plurality of microneedles wherein the volume will depend on the concentration of the specific immune stimulants used.

In some embodiments, the dissolvable microneedle patch comprises a plurality of microneedles with a tip portion. In some embodiments, the dissolvable microneedle patch comprises a plurality of microneedles with a tip portion, wherein the tip portion constitutes about 5% to about 99% of the total volume of the microneedle. In some embodiments, the microneedle tip portion constitutes about 20% to about 90% of the total volume of the microneedle. In some embodiments, the microneedle tip portion constitutes about 50% of the total volume of the microneedle. In some embodiments, the microneedle tip portion constitutes about 75% of the total volume of the microneedle. In some embodiments, the microneedle tip portion constitutes about 5% to about 99%, about 5% to about 95%, about 5% to about 90%, about 5% to about 85%, about 5% to about 80%, about 5% to about 75%, about 5% to about 70%, about 5% to about 60%, about 5% to about 50%, about 5% to about 40%, about 5% to about 30%, about 5% to about 20%, about 5% to about 15%, about 5% to about 10%, about 10% to about 99%, about 10% to about 95%, about 10% to about 90%, about 10% to about 85%, about 10% to about 80%, about 10% to about 75%, about 10% to about 70%, about 10% to about 60%, about 10% to about 50%, about 10% to about 40%, about 10% to about 30%, about 10% to about 20%, about 10% to about 15%, about 15% to about 99%, about 15% to about 95%, about 15% to about 90%, about 15% to about 85%, about 15% to about 80%, about 15% to about 75%, about 15% to about 70%, about 15% to about 60%, about 15% to about 50%, about 15% to about 40%, about 15% to about 30%, about 15% to about 20%, about 25% to about 99%, about 25% to about 95%, about 25% to about 90%, about 25% to about 85%, about 25% to about 80%, about 25% to about 75%, about 25% to about 70%, about 25% to about 60%, about 25% to about 50%, about 25% to about 40%, about 25% to about 30%, about 50% to about 99%, about 50% to about 95%, about 50% to about 90%, about 50% to about 85%, about 50% to about 80%, about 50% to about 75%, about 50% to about 70%, about 50% to about 60%, about 60% to about 99%, about 60% to about 95%, about 60% to about 90%, about 60% to about 85%, about 60% to about 80%, about 60% to about 75%, about 60% to about 70%, about 70% to about 99%, about 70% to about 95%, about 70% to about 90%, about 70% to about 85%, about 70% to about 80%, about 70% to about 75%, about 80% to about 99%, about 80% to about 95%, about 80% to about 90%, about 80% to about 85%, about 90% to about 99%, about 90% to about 95%, or a value within these ranges. Specific examples may include about 99%, about 95%, about 90%, about 85%, about 80%, about 75%, about 70%, about 65%, about 60%, about 55%, about 50%, about 45%, about 40%, about 35%, about 30%, about 25%, about 20% about 15%, about 10%, about 9%, about 8%, about 7%, about 6%, about 5%, or a range between any two of these values. In some embodiments, the plurality of microneedles comprise a therapeutically active ingredient. In some embodiments, the plurality of microneedles each comprise about the same amount of the therapeutically active ingredient. In some embodiments, the plurality of microneedles each comprise different amounts of the therapeutically active ingredient.

In some embodiments, the method of treating a skin condition comprising applying a dissolvable microneedle patch wherein the skin condition is a wart, condyloma acuminatum, Bowenoid papulosis, molluscum contagiosum, actinic keratosis, squamous cell carcinoma, basal cell carcinoma, verrucous carcinoma, epidermodysplasia verruciformis, Gorlin's syndrome, and alopecia areata, vitiligo.

Certain compounds disclosed herein may possess useful immune stimulating activity and may be used in the treatment or prophylaxis of a disease or condition in which the immune system can play an active role. In some embodiments, successful delivery of immune stimulant results in classic clinical signs of inflammation such as, rubor, tumor, and calor (redness, swelling and warmth, respectively). Thus, embodiments are also directed to pharmaceutical compositions comprising one or more compounds disclosed herein together with a pharmaceutically acceptable carrier, as well as methods of making and using the compounds and compositions. Certain embodiments are directed to methods for stimulating the immune system. Other embodiments are directed to methods for treating a skin condition in a patient in need of such treatment, comprising administering to said patient a therapeutically effective amount of a compound or composition according to the present invention. Also provided is the use of certain compounds disclosed herein in the manufacture of a medicament for the treatment of a disease or condition ameliorated by the activation of the immune system.

In some embodiments, a method of treating a skin condition by administering a pharmaceutical composition of embodiments disclosed herein. In some embodiments, the compound is in a therapeutically effective amount. In some embodiments, the therapeutically effective amount is an amount disclosed herein. In some embodiments, administration of the dissolvable microneedle patch leads to a disappearance of the conditions being treated. In some embodiments, administration of the dissolvable microneedle patch leads to disappearance of the skin lesion or skin lesions in direct contact with the dissolvable microneedle patch. In some embodiments, administration of the dissolvable microneedle patch leads to the disappearance of the skin lesion or skin lesions adjacent to the dissolvable microneedle patch.

In some embodiments, the plurality of microneedles comprise a therapeutically active ingredient wherein therapeutically active ingredient is selected from the group consisting of a vaccine, an immune stimulating molecule, immune stimulating organism, and an immune stimulating protein. In some embodiments, the dissolvable microneedle patch delivers the therapeutically active ingredient to stimulate a local immune response. In some embodiments, the therapeutically active ingredient is a vaccine, wherein the vaccine is selected from the group consisting of measles-mumps-rubella vaccine, mumps vaccine, *Bacillus* Calmette-Guérin vaccine, human papillomavirus vaccine, and *Mycobacterium w* vaccine. In some embodiments, the therapeutically active ingredient is an immune stimulating molecule, wherein the immune stimulating molecule is imiquimod. In some embodiments, the therapeutically active ingredient is an immune stimulating organism, wherein the immune stimulating organism is *Corynebacterium parvus, Cutibacterium acnes, Propionibacterium*, and/or *Mycobacterium indicus pranii* (formerly *Mycobacterium w*). In some embodiments, the therapeutically active ingredient is an immune stimulating protein, wherein the immune stimulating protein is selected from the group consisting of *Candida* antigen, *Trichophyton* antigen, tuberculin, purified protein derivative (also), human papillomavirus surface proteins, interferon alpha, interferon beta, and interferon gamma.

In some embodiments, the plurality of microneedles comprise a therapeutically active ingredient wherein therapeutically active ingredient is *Candida* antigen. In some embodiments, the therapeutically active ingredient is *Candida* antigen. In some embodiments, the *Candida* antigen is substantially free of glycerin. In some embodiments, the *Candida* antigen is glycerin free. In some embodiments, the glycerin free *Candida* antigen is lyophilized.

In some embodiments, the plurality of microneedles comprise a therapeutically active ingredient wherein therapeutically active ingredient is dispersed throughout the polymer. In some embodiments, the plurality of microneedles comprise a therapeutically active ingredient wherein the therapeutically active ingredient is evenly distributed throughout the microneedle. In some embodiments, the plurality of microneedles comprise a therapeutically active ingredient wherein the therapeutically active ingredient is concentrated at the tip of the microneedle. In some embodiments, the plurality of microneedles comprise a microneedle with essentially no therapeutically active ingredient in the half of the microneedle closest to the base. In some embodiments, the plurality of microneedles comprise a microneedle with no therapeutically active ingredient in the half of the microneedle closest to the base. In some embodiments, the therapeutically active ingredient is a solid powder. In some embodiments, the therapeutically active ingredient is a solid powder dispersed throughout the polymer. In some embodiments, the therapeutically active ingredient is lyophilized. In some embodiments, the therapeutically active ingredient is lyophilized and dispersed throughout the polymer.

Some embodiments disclosed herein also include pharmaceutical compositions which contain, as the active ingredient, one or more of the compounds disclosed herein in combination with one or more pharmaceutically acceptable carriers (excipients).

The active compound can be effective over a wide dosage range and can be generally administered in a therapeutically effective amount. It will be understood, however, that the amount of the compound actually administered will usually be determined by a physician, according to the relevant circumstances, including the condition to be treated, the actual compound administered, the age, weight, and response of the individual patient, the severity of the patient's symptoms, and the like. In some embodiments, the plurality of microneedles will contain equal amounts of therapeutically active ingredient. In some embodiments, the plurality of microneedles will contain unequal amounts of therapeutically active ingredient.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. In some embodiments, that condition is selected from a wart, condyloma acuminatum, Bowenoid papulosis, molluscum contagiosum, actinic keratosis, squamous cell carcinoma, basal cell carcinoma, verrucous carcinoma, epidermodysplasia verruciformis and successful treatment of these conditions results in a one point improvement on any ordinal or interval assessment scale, such as the Physician Global Assessment or the Investigator Global Assessment. In some embodiments, the condition is selected from a wart, condyloma acuminatum, Bowenoid papulosis, molluscum contagiosum, actinic keratosis, squamous cell carcinoma, basal cell carcinoma, verrucous carcinoma, epidermodysplasia verruciformis and successful treatment of these conditions results in about 100% loss of skin lesions by clinical, histopathological, or dermatoscopic assessment as well as assessment by optical coherence tomography or confocal microscopy in the location of the patch is administered. In some embodiments, the condition is selected from a wart, condyloma acuminatum, Bowenoid papulosis, molluscum contagiosum, actinic keratosis, squamous cell carcinoma, basal cell carcinoma, verrucous carcinoma, epidermodysplasia verruciformis and successful treatment of these conditions results in about 50% loss of skin lesions by clinical, histopathological, or dermatoscopic assessment as well as assessment by optical coherence tomography or confocal microscopy in the location of the patch is administered. In some embodiments, successful treatment of a wart, condyloma acuminatum, Bowenoid papulosis, molluscum contagiosum, actinic keratosis, squamous cell carcinoma, basal cell carcinoma, verrucous carcinoma, epidermodysplasia verruciformis with the dissolvable microneedle patch results in reduction of skin lesions in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include reducing skin lesions, by clinical, histopathological, or dermatoscopic assessment as well as assessment by optical coherence tomography or confocal microscopy by about 100%, about 99%, about 95%, about 90%, about 85%, about 80%, about 75%, about 70%, about 65%, about 60%, about 55%, about 50% or a range between any two of these values.

In some embodiments, successful treatment of a wart, condyloma acuminatum, Bowenoid papulosis, molluscum contagiosum, actinic keratosis, squamous cell carcinoma, basal cell carcinoma, verrucous carcinoma, epidermodysplasia verruciformis with the dissolvable microneedle patch results in reduction of in the width, length, or height of skin lesions in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include reducing the width, length, or height of skin lesions measured by clinical, histopathological, or dermatoscopic assessment as well as assessment by optical coherence tomography or confocal microscopy by about 100%, about 99%, about 95%, about 90%, about 85%, about 80%, about 75%, about 70%, about 65%, about 60%, about 55%, about 50% or a range between any two of these values.

In some embodiments, the condition is alopecia areata and successful treatment of this condition results in a one point improvement on any ordinal or interval assessment scale, such as the Physician Global Assessment or the Investigator Global Assessment. In some embodiments, the condition is alopecia areata and successful treatment of this condition results in about 100% restoration of hair growth in the location of the patch is administered. In some embodiments, the condition is alopecia areata and successful treatment of this condition results in at least about 50% increase in hair growth as defined by number of hair follicles with actively growing hair shafts as seen with clinical, trichoscopic, or histopathological assessment in the location the patch is administered. In some embodiments, successful treatment of alopecia areata with the dissolvable microneedle patch results in an increase in hair growth in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include increasing hair growth as defined by the number of hair follicles with actively growing hair shafts as seen with clinical, trichoscopic, or histopathologic assessment, by about 100%, about 99%, about 95%, about 90%, about 85%, about 80%, about 75%, about 70%, about 65%, about 60%, about 55%, about 50% or a range between any two of these values.

In some embodiments, successful treatment of alopecia areata with the dissolvable microneedle patch results in improvement in the Severity Alopecia Tool (SALT) score in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include improving the Severity Alopecia Tool (SALT) score by about 100%, about 99%, about 95%, about 90%, about 85%, about 80%, about 75%, about 70%, about 65%, about 60%, about 55%, about 50% or a range between any two of these values.

In some embodiments, each dissolvable microneedle patch will contain a standardized amount of therapeutically active ingredient.

In some embodiments, the dissolvable microneedles may comprise about 1% to about 90% of one or more therapeutically active ingredients disclosed herein. In some embodiments, the dissolvable microneedles may comprise about 50% to about 75% of one or more therapeutically active ingredients disclosed herein. In some embodiments, the dissolvable microneedles may comprise about 25% to about 50% of one or more therapeutically active ingredients disclosed herein. In some embodiments, the dissolvable microneedles may comprise about 25% to about 75% of one or more therapeutically active ingredients disclosed herein. In some embodiments, the dissolvable microneedles may comprise about 40% to about 60% of one or more therapeutically active ingredients disclosed herein. In some embodiments, the dissolvable microneedles may comprise about 60% to about 80% of one or more therapeutically active ingredients disclosed herein. In some embodiments, the one or more therapeutically active ingredients are in an amount of about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45% 15% to about 40%, about 15% to about 35%, about 15% to about 30%, about 15% to about 25%, about 15% to about 20%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 35% to about 90%, about 35% to about 85%, about 35% to about 80%, about 35% to about 75%, about 35% to about 70%, about 35% to about 65%, about 35% to about 60%, about 35% to about 60%, about 35% to about 55%, about 35% to about 50%, about 35% to about 45%, about 35% to about 40%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 45% to about 90%, about 45% to about 85%, about 45% to about 80%, about 45% to about 75%, about 45% to about 70%, about 45% to about 65%, about 45% to about 60%, about 45% to about 55%, about 45% to about 50%, about 50% to about 90%, about 50% to about 85%, about 50% to about 80%, about 50% to about 75%, about 50% to about 70%, about 50% to about 65%, about 50% to about 60%, about 50% to about 55%, about 55% to about 90%, about 55% to about 85%, about 55% to about 80%, about 55% to about 75%, about 55% to about 70%, about 55% to about 65%, about 55% to about 60%, about 60% to about 90%, about 60% to about 85%, about 60% to about 80%, about 60% to about 75%, about 60% to about 70%, about 60% to about 65%, about 65% to about 90%, about 65% to about 85%, about 65% to about 80%, about 65% to about 75%, about 65% to about 70%, about 70% to about 90%, about 70% to about 85%, about 70% to about 80%, about 70% to about 75%, about 75% to about 90%, about 75% to about 85%, about 75% to about 80%, about 80% to about 90%, about 80% to about 85%, about 85% to about 90%, or a value within one of these ranges. Specific examples may include about 90%, about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 9%, about 8%, about 7%, about 6%, about 5%, about 4% about 3%, about 2%, about 1%. The foregoing all representing weight percentages of the pharmaceutical composition. In some embodiments, the pharmaceutical composition is suitable for transdermal administration.

In some embodiments, the therapeutically active ingredient is in a therapeutically effective amount. In some embodiments, the therapeutically effective amount may be about 1 microgram to 999 micrograms, 1 microgram to 100 micrograms, 100 micrograms to 200 micrograms, 200 micrograms to 300 micrograms, 300 micrograms to 400 micrograms, 400 micrograms to 500 micrograms, 500 micrograms to 600 micrograms, 600 micrograms to 700 micrograms, 700 micrograms to 800 micrograms, 800 micrograms to 900 micrograms, 900 micrograms to 999 micrograms, 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg, or any value between the ranges disclosed above.

In some embodiments, the therapeutically effective amount can vary according to, for example, the particular use for which the treatment is made, the location of administration of the microneedle patch, the health and condition of the patient, and the judgment of the prescribing physician. The proportion or concentration of a compound in a dissolvable microneedle can vary depending upon a number of factors including dosage, chemical characteristics (e.g., hydrophobicity), and the type of microneedle polymer. The dosage is likely to depend on such variables as the type and extent of progression of the disease or disorder, the overall health status of the particular patient, the relative biological efficacy of the compound selected, composition of the excipient, and its location of administration. Effective doses can be extrapolated from dose-response curves derived from in vitro or animal model test systems.

In some embodiments, the dissolvable microneedle patch comprises a plurality of microneedles, wherein the microneedles comprise a biodegradable polymer. In some embodiments, the dissolvable microneedle patch comprises a plurality of microneedles, wherein the microneedles comprise poly(lactic-co-glycolic acid) (PLGA). In some embodiments, the dissolvable microneedle patch comprises a plurality of microneedles, wherein the microneedles comprise a polymer selected from PLGA (poly(lactic-co-glycolic acid)), polyglycolic acid, fibroin, PLA (polylactic acid), PVP (polyvinylpyrrolidone), or PCL (polycaprolactone). In some embodiments, the dissolvable microneedle patch comprises a plurality of microneedles, wherein the microneedles comprise a single biodegradable polymer. In some embodiments, the dissolvable microneedle patch comprises a plurality of microneedles, wherein the microneedles comprise two biodegradable polymers. In some embodiments, the dissolvable microneedle patch comprises a plurality of microneedles, wherein the microneedles comprise a plurality of biodegradable polymers.

In some embodiments, the biodegradable polymer is capable of providing immediate release of a therapeutically active ingredient after insertion of the microneedle patch into the skin. In further embodiments, the immediate release biodegradable polymer is water soluble and comprises carboxy methylcellulose, chondroitin sulfate, dextran, dextrin, polyvinylpyrrolidone, maltose, trehalose, sucrose, galactose, amylopectin, polyvinyl alcohol, and/or polyvinylpyrrolidone-methacrylic acid. In further embodiments, the immediate release biodegradable polymer releases the therapeutically active ingredient within about 0 hours to about 24 hours after insertion of the microneedle patch to the skin. In some embodiments, the immediate release biodegradable polymer releases at least about 75% of the therapeutically active ingredient on a timescale of about 0 hours to about 24 hours. In some embodiments, the immediate release biodegradable polymer releases about 100% of the therapeutically active ingredient on a timescale of about 0 hours to about 24 hours. In some embodiments, the immediate release biodegradable polymer releases therapeutically active ingredient on a timescale of about 0 hours to about 24 hours in a range of about 75% to about 100%, about 75% to about 95%, about 75% to about 90%, about 75% to about 85%, about 75% to about 80%, about 80% to about 100%, about 80% to about 95%, about 80% to about 90%, about 80% to about 85%, about 85% to about 100%, about 85% to about 95%, about 85% to about 90%, about 90% to about 100%, about 90% to about 95%, about 95% to about 100%, or a value within these ranges. Specific examples may include about 75%, about 80%, about 85%, about 90%, about 95%, about 99%, about 100%, or a range between any two of these values.

In some embodiments, the immediate release biodegradable polymer releases the therapeutically active ingredient within about 0 hours to about 24 hours after insertion of the microneedle patch to the skin. In some embodiments, the immediate release biodegradable polymer releases the therapeutically active ingredient within about 0 minutes to about 10 minutes after insertion of the microneedle patch to the skin. In some embodiments, the immediate release biodegradable polymer releases the therapeutically active ingredient within about 0 minutes to about 5 minutes after insertion of the microneedle patch to the skin. In some embodiments, the immediate release biodegradable polymer releases therapeutically active ingredient within about 0 hours to about 24 hours, about 0 hours to about 23 hours, about 0 hours to about 22 hours, about 0 hours to about 21 hours, about 0 hours to about 20 hours, about 0 hours to about 18 hours, about 0 hours to about 16 hours, about 0 hours to about 14 hours, about 0 hours to about 12 hours, about 0 hours to about 10 hours, about 0 hours to about 9 hours, about 0 hours to about 8 hours, about 0 hours to about 7 hours, about 0 hours to about 6 hours, about 0 hours to about 5 hours, about 0 hours to about 4 hours, about 0 hours to about 3 hours, about 0 hours to about 2 hours, about 0 hours to about 1 hour, about 1 hour to about 24 hours, about 1 hour to about 23 hours, about 1 hour to about 22 hours, about 1 hour to about 21 hours, about 1 hour to about 20 hours, about 1 hour to about 18 hours, about 1 hour to about 16 hours, about 1 hour to about 14 hours, about 1 hour to about 12 hours, about 1 hour to about 10 hours, about 1 hour to about 9 hours, about 1 hour to about 8 hours, about 1 hour to about 7 hours, about 1 hour to about 6 hours, about 1 hour to about 5 hours, about 1 hour to about 4 hours, about 1 hour to about 3 hours, about 1 hour to about 2 hours, about 2 hours to about 24 hours, about 2 hours to about 23 hours, about 2 hours to about 22 hours, about 2 hours to about 21 hours, about 2 hours to about 20 hours, about 2 hours to about 18 hours, about 2 hours to about 16 hours, about 2 hours to about 14 hours, about 2 hours to about 12 hours, about 2 hours to about 10 hours, about 2 hours to about 9 hours, about 2 hours to about 8 hours, about 2 hours to about 7 hours, about 2 hours to about 6 hours, about 2 hours to about 5 hours, about 2 hours to about 4 hours, about 2 hours to about 3 hours, about 5 hours to about 24 hours, about 5 hours to about 23 hours, about 5 hours to about 22 hours, about 5 hours to about 21 hours, about 5 hours to about 20 hours, about 5 hours to about 18 hours, about 5 hours to about 16 hours, about 5 hours to about 14 hours, about 5 hours to about 12 hours, about 5 hours to about 10 hours, about 5 hours to about 9 hours, about 5 hours to about 8 hours, about 5 hours to about 7 hours, about 5 hours to about 6 hours, about 12 hours to about 24 hours, about 12 hours to about 23 hours, about 12 hours to about 22 hours, about 12 hours to about 21 hours, about 12 hours to about 20 hours, about 12 hours to about 18 hours, 12 hours to about 16 hours, about 12 hours to about 14 hours, about 12 hours to about 13 hours, about 18 hours to about 24 hours, about 18 hours to about 23 hours, about 18 hours to about 22 hours, about 18 hours to about 21 hours, about 18 hours to about 20 hours, about 18 hours to about 19 hours, about 20 hours to about 24 hours, about 20 hours to about 23 hours, about 20 hours to about 22 hours, about 20 hours to about 21 hours, about 0 minutes to about 60 minutes, about 0 minutes to about 50 minutes, about 0 minutes to about 45 minutes, about 0 minutes to about 30 minutes, about 0 minutes to about 15 minutes, about 0 minutes to about 10 minutes, about 0 minutes to about 5 minutes, about 0 minutes to about 4 minutes, about 0 minutes to about 3 minutes, 0 minutes to about 2 minutes, 0 minutes to about 1 minute, about 5 minutes to about 60 minutes, about 5 minutes to about 50 minutes, about 5 minutes to about 45 minutes, about 5 minutes to about 30 minutes, about 5 minutes to about 15 minutes, about 5 minutes to about 10 minutes, about 10 minutes to about 60 minutes, about 10 minutes to about 50 minutes, about 10 minutes to about 45 minutes, about 10 minutes to about 30 minutes, about 10 minutes to about 15 minutes, about 15 minutes to about 60 minutes, about 15 minutes to about 50 minutes, about 15 minutes to about 45 minutes, about 15 minutes to about 30 minutes, about 15 minutes to about 25 minutes, about 15 minutes to about 20 minutes, about 30 minutes to about 60 minutes, about 30 minutes to about 50 minutes, about 30 minutes to about 45 minutes, about 30 minutes to about 40 minutes, about 30 minutes to about 35 minutes, about 45 minutes to about 60 minutes, about 45 minutes to about 50 minutes, or a value within these ranges. Specific examples may include about 24 hours, about 23 hours, about 22 hours, about 21 hours, about 20 hours, about 18 hours, about 16 hours, about 14 hours, about 12 hours, about 10 hours, about 9 hours, about 8 hours, about 7 hours, about 6 hours, about 5 hours, about 4 hours, about 3 hours, about 2 hours about 1 hour, about 60 minutes, about 55 minutes, about 50 minutes, about 45 minutes, about 40 minutes, about 35 minutes, about 30 minutes, about 25 minutes, about 20 minutes, about 15 minutes, about 10 minutes, about 9 minutes, about 8 minutes, about 7 minutes, about 6 minutes, about 5 minutes, about 4 minutes about 3 minutes, about 2 minutes, about 1 minute, or a range between any two of these values.

In some embodiments, the biodegradable polymer is capable of providing sustained release of a therapeutically active ingredient after insertion of the microneedle patch into the skin. In further embodiments, the sustained release biodegradable polymer is water soluble and includes PLGA (poly(lactic-co-glycolic acid)), polyglycolic acid, fibroin, PLA (polylactic acid), PVP (polyvinylpyrrolidone), or PCL (polycaprolactone). In further embodiments, the sustained release biodegradable polymer releases the therapeutically active ingredient after about 24 hours of insertion of the microneedle patch to the skin. In some embodiments, the sustained release biodegradable polymer does not release more than 75% of the therapeutically active ingredient until a time greater than about 24 hours after insertion of the microneedle patch to the skin. In some embodiments, the sustained release biodegradable polymer does not release therapeutically active ingredient until a time greater than about 24 hours in amounts of about 75% to about 100%, about 75% to about 99%, about 75% to about 95%, about 75% to about 90%, about 75% to about 85%, about 75% to about 80%, about 80% to about 100%, about 80% to about 99%, about 80% to about 95%, about 80% to about 90%, about 80% to about 85%, about 85% to about 100%, about 85% to about 99%, about 85% to about 95%, about 85% to about 90%, about 90% to about 100%, about 90% to about 99%, about 90% to about 95%, about 95% to about 100%, about 95% to about 99%, about 99% to about 100%, or a value within these ranges. Specific examples may include about 75%, about 80% about 85%, about 90%, about 95%, about 99%, about 100%.

In some embodiments, the sustained release biodegradable polymer releases the therapeutically active ingredient over about 1 day to about 30 days. In some embodiments, the sustained release biodegradable polymer releases the therapeutically active ingredient over about 2 days to about 21 days. In some embodiments the sustained release biodegradable polymer releases the therapeutically active over about 1 day to about 30 days, about 1 day to about 28 days, about 1 day to about 26 days, about 1 day to about 24 days, about 1 days to about 22 days, about 1 day to about 21 days, about 1 day to about 14 days, about 1 day to about 7 days, about 1 day to about 6 days, about 1 day to about 5 days, about 1 day to about 4 days, about 1 day to about 3 days, about 1 day to about 2 days, about 2 days to about 30 days, about 2 days to about 28 days, about 2 days to about 26 days, about 2 days to about 24 days, about 2 days to about 22 days, about 2 days to about 21 days, about 2 days to about 14 days, about 2 days to about 7 days, about 2 days to about 6 days, about 2 days to about 5 days, about 2 days to about 4 days, about 2 days to about 3 days, about 3 days to about 30 days, about 3 days to about 28 days, about 3 days to about 26 days, about 3 days to about 24 days, about 3 days to about 22 days, about 3 days to about 21 days, about 3 days to about 14 days, about 3 days to about 7 days, about 3 days to about 6 days, about 3 days to about 5 days, about 3 days to about 4 days, about 4 days to about 30 days, about 4 days to about 28 days, about 4 days to about 26 days, about 4 days to about 24 days, about 4 days to about 22 days, about 4 days to about 21 days, about 4 days to about 14 days, about 4 days to about 7 days, about 4 days to about 6 days, about 4 days to about 5 days, about 5 days to about 30 days, about 5 days to about 28 days, about 5 days to about 26 days, about 5 days to about 24 days, about 5 days to about 22 days, about 5 days to about 21 days, about 5 days to about 14 days, about 5 days to about 7 days, about 5 days to about 6 days, about 7 days to about 30 day, about 7 days to about 28 days, about 7 days to about 26 days, about 7 days to about 24 days, about 7 days to about 24 days, about 7 days to about 22 days, about 7 days to about 21 days, about 7 days to about 14 days, about 14 days to about 30 days, about 14 days to about 28 days, about 14 days to about 26 days, about 14 days to about 24 days, about 14 days to about 22 days, about 14 days to about 21 days, about 21 days to about 30 days, about 21 days to about 28 days, about 21 days to about 26 days, about 21 days to about 24 days, about 21 days to about 22 days or a value within these ranges. Specific examples may include about 30 days, about 28 days, about 26 days, about 24 days, about 22 days about 21 days, about 14 days, about 7 days, about 6 days, about 5 days, about 4 days, about 3 days, about 2 days, about 1 day or a range between any two of these values.

In some embodiments, the biodegradable polymer is capable of providing both sustained release and immediate release of a therapeutically active ingredient after insertion of the microneedle patch into the skin. In some embodiments, the plurality of microneedles comprise immediate release biodegradable polymer and sustained release biodegradable polymer. In some embodiments, the plurality of microneedles contain immediate release biodegradable polymer at the base of the microneedle and sustained release biodegradable polymer at the tip of the microneedle. In some embodiments, the plurality of microneedles contain immediate release biodegradable polymer at the base of the microneedle and alternating layers of immediate release biodegradable polymer and sustained release biodegradable polymer at the tip of the microneedle.

In some embodiments, the dissolvable microneedle patch is applied on a skin lesion of a patient in need thereof to treat a skin condition. In some embodiments, the dissolvable microneedle patch is applied adjacent to a skin lesion of a patient in need thereof to treat a skin condition. In some embodiments, the dissolvable microneedle patch is applied to an area of the skin that is determined to be optimal based on the age of the patient. In some embodiments, the dissolvable microneedle patch is applied to an area of the skin that is determined to be optimal based on the type of skin in need of treatment.

In some embodiments, the dissolvable microneedle patch comprises a plurality of microneedles, wherein the microneedles are spatially separated within the skin wherein one microneedle does not touch another microneedle. In some embodiments, the dissolvable microneedle patch comprises a plurality of microneedles, wherein the microneedle patch comprises at least about one to about 200 microneedles per square centimeter, about one to about 175 microneedles per square centimeter, about one to about 150 microneedles per square centimeter, about one to about 125 microneedles per square centimeter, about one to about 100 microneedles per square centimeter, about one to about 90 microneedles per square centimeter, about one to about 80 microneedles per square centimeter, about one to about 70 microneedles per square centimeter, about one to about 60 microneedles per square centimeter, about one to about 50 microneedles per square centimeter, about one to about 40 microneedles per square centimeter, about one to about 30 microneedles per square centimeter, about one to about 25 microneedles per square centimeter, about one to about 20 microneedles per square centimeter, about one to about 15, about one to about 10 microneedles per square centimeter, about one to about 5 microneedles per square centimeter, about 5 to about 200 microneedles per square centimeter, about 5 to about 175 microneedles per square centimeter, about 5 to about 150 microneedles per square centimeter, about 5 to about 125 microneedles per square centimeter, about 5 to about 100 microneedles per square centimeter, about 5 to about 90 microneedles per square centimeter, about 5 to about 80 microneedles per square centimeter, about 5 to about 70 microneedles per square centimeter, about 5 to about 60 microneedles per square centimeter, about 5 to about 50 microneedles per square centimeter, about 5 to about 40 microneedles per square centimeter, about 5 to about 30 microneedles per square centimeter, about 5 to about 25 microneedles per square centimeter, about 5 to about 20 microneedles per square centimeter, about 5 to about 15 microneedles per square centimeter, about 5 to about 20 microneedles per square centimeter, about 10 to about 200 microneedles per square centimeter, about 10 to about 175 microneedles per square centimeter, about 10 to about 150 microneedles per square centimeter, about 10 to about 150 microneedles per square centimeter, about 10 to about 125 microneedles per square centimeter, about 10 to about 100 microneedles per square centimeter, about 10 to about 90 microneedles per square centimeter, about 10 to about 80 microneedles per square centimeter, about 10 to about 70 microneedles per square centimeter, about 10 to about 60 microneedles per square centimeter, about 10 to about 50 microneedles per square centimeter, about 10 to about 40 microneedles per square centimeter, about 10 to about 30 microneedles per square centimeter, about 10 to about 25 microneedles per square centimeter, about 10 to about 20 microneedles per square centimeter, about 10 to about 15 microneedles per square centimeter, about 25 to about 200 microneedles per square centimeter, about 25 to about 175 microneedles per square centimeter, about 25 to about 150 microneedles per square centimeter, about 25 to about 125 microneedles per square centimeter, about 25 to about 100 microneedles per square centimeter, about 25 to about 90 microneedles per square centimeter, about 25 to about 80 microneedles per square centimeter, about 25 to about 70 microneedles per square centimeter, about 25 to about 60 microneedles per square centimeter, about 25 to about 50 microneedles per square centimeter, about 25 to about 40 microneedles per square centimeter, about 25 to about 30 microneedles per square centimeter, about 50 to about 200 microneedles per square centimeter, about 50 to about 175 microneedles per square centimeter, about 50 to about 150 microneedles per square centimeter, about 50 to about 125 microneedles per square centimeter, about 50 to about 100 microneedles per square centimeter, about 50 to about 90 microneedles per square centimeter, about 50 to about 80 microneedles per square centimeter, about 50 to about 70 microneedles per square centimeter, about 50 to about 60 microneedles per square centimeter, about 75 to about 200 microneedles per square centimeter, about 75 to about 175 microneedles per square centimeter, about 75 to about 150 microneedles per square centimeter, about 75 to about 125 microneedles per square centimeter, about 75 to about 100 microneedles per square centimeter, about 75 to about 90 microneedles per square centimeter, about 75 to about 80 microneedles per square centimeter, about 100 to about 200 microneedles per square centimeter, about 100 to about 175 microneedles per square centimeter, about 100 to about 150 microneedles per square centimeter, about 100 to about 125 microneedles per square centimeter, about 125 to about 200 microneedles per square centimeter, about 125 to about 175 microneedles per square centimeter, about 125 to about 150 microneedles per square centimeter, about 150 to about 200 microneedles per square centimeter, about 150 to about 175 microneedles per square centimeter, about 175 to about 200 microneedles per square centimeter, or a value within these ranges. Specific examples may include a dissolvable microneedle patch comprising a plurality of microneedles, wherein the microneedle patch comprises at least about 200 microneedles per square centimeter, at least about 175 microneedles per square centimeter, at least about 150 microneedles per square centimeter, at least about 125 microneedles per square centimeter, at least about 100 microneedles per square centimeter, at least about 90 microneedles per square centimeter, at least about 80 microneedles per square centimeter, at least about 70 microneedles per square centimeter, at least about 60 microneedles per square centimeter, at least about 50 microneedles per square centimeter, at least about 40 microneedles per square centimeter, at least about 30 microneedles per square centimeter, at least about 25 microneedles per square centimeter, at least about 20 microneedles per square centimeter, at least about 15 microneedles per square centimeter, at least about 10 microneedles per square centimeter, at least about 5 microneedles per square centimeter, at least about 4 microneedles per square centimeter, at least about 3 microneedles per square centimeter, at least about 2 microneedles per square centimeter, at least about 1 microneedle per square centimeter, or a range between any two of these values.

In some embodiments, the dissolvable microneedle patch is any shape necessary to accommodate the surface topology of the skin. In some embodiments, the dissolvable microneedle patch has any of n number of sides with n ranging from about 0 sides to about 1000 sides. In some embodiments, the dissolvable microneedle patch has about 0 sides to about 1000 sides, about 0 sides to about 900 sides, about 0 sides to about 800 sides, about 0 sides to about 700 sides, about 0 sides to about 600 sides, about 0 sides to about 500 sides, about 0 sides to about 400 sides, about 0 sides to about 300 sides, about 0 sides to about 200 sides, about 0 sides to about 100 sides, about 0 sides to about 90 sides, about 0 sides to about 80 sides, about 0 sides to about 70 sides, about 0 sides to about 60 sides, about 0 sides to about 50 sides, about 0 sides to about 40 sides, about 0 sides to about 30 sides, about 0 sides to about 20 sides, about 0 sides to about 10 sides, about 0 sides to about 9 sides, about 0 sides to about 8 sides, about 0 sides to about 7 sides, about 0 sides to about 6 sides, about 0 sides to about 5 sides, about 0 sides to about 4 sides, about 0 sides to about 3 sides, about 0 sides to about 2 sides, about 10 sides to about 1000 sides, about 10 sides to about 900 sides, about 10 sides to about 800 sides, about 10 sides to about 700 sides, about 10 sides to about 600 sides, about 10 sides to about 500 sides, about 10 sides to about 400 sides, about 10 sides to about 300 sides, about 10 sides to about 200 sides, about 10 sides to about 100 sides, about 10 sides to about 90 sides, about 10 sides to about 80 sides, about 10 sides to about 70 sides, about 10 sides to about 60 sides, about 10 sides to about 50 sides, about 10 sides to about 40 sides, about 10 sides to about 30 sides, about 10 sides to about 20 sides, about 20 sides to about 1000 sides, about 20 sides to about 900 sides, about 20 sides to about 800 sides, about 20 sides to about 700 sides, about 20 sides to about 600 sides, about 20 sides to about 500 sides, about 20 sides to about 400 sides, about 20 sides to about 300 sides, about 20 sides to about 200 sides, about 20 sides to about 100 sides, about 20 sides to about 90 sides, about 20 sides to about 80 sides, about 20 sides to about 70 sides, about 20 sides to about 60 sides, about 20 sides to about 50 sides, about 20 sides to about 40 sides, about 20 sides to about 30 sides, about 30 sides to about 1000 sides, about 30 sides to about 900 sides, about 30 sides to about 800 sides, about 30 sides to about 700 sides, about 30 sides to about 600 sides, about 30 sides to about 500 sides, about 30 sides to about 400 sides, about 30 sides to about 300 sides, about 30 sides to about 200 sides, about 30 sides to about 100 sides, about 30 sides to about 90 sides, about 30 sides to about 80 sides, about 30 sides to about 70 sides, about 30 sides to about 60 sides, about 30 sides to about 50 sides, about 30 sides to about 40 sides, about 50 sides to about 1000 sides, about 50 sides to about 900 sides, about 50 sides to about 800 sides, about 50 sides to about 700 sides, about 50 sides to about 600 sides, about 50 sides to about 500 sides, about 50 sides to about 400 sides, about 50 sides to about 300 sides, about 50 sides to about 200 sides, about 50 sides to about 100 sides, about 50 sides to about 90 sides, about 50 sides to about 80 sides, about 50 sides to about 70 sides, about 50 sides to about 60 sides, about 75 side to about 1000 sides, about 75 to about 900 sides, about 75 to about 800 sides, about 75 to about 700 sides, about 75 to about 600 sides, about 75 to about 500 sides, about 75 to about 400 sides, about 75 to about 300 sides, about 75 to about 200 sides, about 75 to about 200 sides, about 75 to about 100 sides, about 75 to about 90 sides, about 75 to about 80 sides, about 100 sides to about 1000 sides, about 100 sides to about 900 sides, about 100 sides to about 800 sides, about 100 sides to about 700 sides, about 100 sides to about 600 sides, about 100 sides to about 500 sides, about 100 sides to about 400 sides, about 100 sides to about 300 sides, about 100 sides to about 200 sides, about 250 sides to about 1000 sides, about 250 sides to about 900 sides, about 250 sides to about 800 sides, about 250 to about 700 sides, about 250 sides to about 600 sides, about 250 sides to about 500 sides, about 250 sides to about 400 sides, about 250 sides to about 300 sides, about 500 sides to about 1000 sides, about 500 sides to about 900 sides, about 500 sides to about 800 sides, about 500 sides to about 700 sides, about 500 sides to about 600 sides, about 750 sides to about 1000 sides, about 750 sides to about 900 sides, about 750 sides to about 800 sides, about 900 sides to about 1000 sides or a value within these ranges. Specific examples may include a dissolvable microneedle patch has about 1000 sides, about 900 sides, about 800 sides, about 700 sides, about 600 sides, about 500 sides, about 400 sides, about 300 sides, about 200 sides, about 100 sides, about 90 sides, about 80 sides, about 70 sides, about 60 sides, about 50 sides, about 40 sides, about 30 sides, about 20 sides, about 10 sides, about 9 sides, about 8 sides, about 7 sides, about 6 sides, about 5 sides, about 4 sides, about 3 sides, about 2 sides, or a range between any two of these values.

In further embodiments, the dissolvable microneedle patch may have sides of equal length. In further embodiments, the dissolvable microneedle patch may have sides of unequal length. In some embodiments, the dissolvable microneedle patch is shaped as a medical bandage. In some embodiments, the dissolvable microneedle patch ranges in size from about 0.1 square centimeters to about 1000 square centimeters, about 0.1 square centimeters to about 900 square centimeters, about 0.1 square centimeters to about 800 square centimeters, about 0.1 square centimeters to about 700 square centimeters, about 0.1 square centimeters to about 600 square centimeters, about 0.1 square centimeters to about 500 square centimeters, about 0.1 square centimeters to about 400 square centimeters, about 0.1 square centimeters to about 300 square centimeters, about 0.1 square centimeters to about 200 square centimeters, about 0.1 square centimeters to about 100 square centimeters, about 0.1 square centimeters to about 90 square centimeters, about 0.1 square centimeters to about 80 square centimeters, about 0.1 square centimeters to about 70 square centimeters, about 0.1 square centimeters to about 60 square centimeters, about 0.1 square centimeters to about 50 square centimeters, about 0.1 square centimeters to about 40 square centimeters, about 0.1 square centimeters to about 30 square centimeters, about 0.1 square centimeters to about 20 square centimeters, about 0.1 square centimeters to about 10 square centimeters, about 0.1 square centimeters to about 5 square centimeters, about 0.1 square centimeters to about 4 square centimeters, about 0.1 square centimeters to about 3 square centimeters, about 0.1 square centimeters to about 2 square centimeters, about 0.1 square centimeters to about 1 square centimeters, about 0.1 square centimeters to about 0.9 square centimeters, about 0.1 square centimeters to about 0.8 square centimeters, about 0.1 square centimeters to about 0.7 square centimeters, about 0.1 square centimeters to about 0.6 square centimeters, about 0.1 square centimeters to about 0.5 square centimeters, about 0.1 square centimeters to about 0.4 square centimeters, about 0.1 square centimeters to about 0.3 square centimeters, about 0.1 square centimeters to about 0.2 square centimeters, about 0.5 square centimeters to about 1000 square centimeters, about 0.5 square centimeters to about 900 square centimeters, about 0.5 square centimeters to about 800 square centimeters, about 0.5 square centimeters to about 700 square centimeters, about 0.5 square centimeters to about to about 600 square centimeters, about 0.5 square centimeters to about to about 500 square centimeters, about 0.5 square centimeters to about 400 square centimeters, about 0.5 square centimeters to about 300 square centimeters, about 0.5 square centimeters to about 200 square centimeters, about 0.5 square centimeters to about 100 square centimeters, about 0.5 square centimeters to about 90 square centimeters, about 0.5 square centimeters to about 80 square centimeters, about 0.5 square centimeters to about 70 square centimeters, about 0.5 square centimeters to about 60 square centimeters, about 0.5 square centimeters to about 50 square centimeters, about 0.5 square centimeters to about 40 square centimeters, about 0.5 square centimeters to about 30 square centimeters, about 0.5 square centimeters to about 20 square centimeters, about 0.5 square centimeters to about 10 square centimeters, about 0.5 square centimeters to about 5 square centimeters, about 0.5 square centimeters to about 4 square centimeters, about 0.5 square centimeters to about 3 square centimeters, about 0.5 square centimeters to about 2 square centimeters, about 0.5 square centimeters to about 1 square centimeters, about 0.5 square centimeters to about 0.9 square centimeters, about 0.5 square centimeters to about 0.8 square centimeters, about 0.5 square centimeters to about 0.7 square centimeters, about 0.5 square centimeters to about 0.6 square centimeters, about 1 square centimeters to about 1000 square centimeters, about 1 square centimeters to about 900 square centimeters, about 1 square centimeters to about 800 square centimeters, about 1 square centimeters to about 700 square centimeters, about 1 square centimeters to about 600 square centimeters, about 1 square centimeters to about 500 square centimeters, about 1 square centimeters to about 400 square centimeters, about 1 square centimeters to about 300 square centimeters, about 1 square centimeters to about 200 square centimeters, about 1 square centimeters to about 100 square centimeters, about 1 square centimeters to about 90 square centimeters, about 1 square centimeters to about 80 square centimeters, about 1 square centimeters to about 70 square centimeters, about 1 square centimeters to about 60 square centimeters, about 1 square centimeters to about 50 square centimeters, about 1 square centimeters to about 40 square centimeters, about 1 square centimeters to about 30 square centimeters, about 1 square centimeters to about 20 square centimeters, about 1 square centimeters to about 10 square centimeters, about 1 square centimeters to about 5 square centimeters, about 1 square centimeters to about 4 square centimeters, about 1 square centimeters to about 3 square centimeters, about 1 square centimeters to about 2 square centimeters, about 10 square centimeters to about 1000 square centimeters, about 10 square centimeters to about 900 square centimeters, about 10 square centimeters to about 800 square centimeters, about 10 square centimeters to about 700 square centimeters, about 10 square centimeters to about 600 square centimeters, about 10 square centimeters to about 500 square centimeters, about 10 square centimeters to about 400 square centimeters, about 10 square centimeters to about 300 square centimeters, about 10 square centimeters to about 200 square centimeters, about 10 square centimeters to about 100 square centimeters, about 10 square centimeters to about 90 square centimeters, about 10 square centimeters to about 80 square centimeters, about 10 square centimeters to about 70 square centimeters, about 10 square centimeters to about 60 square centimeters, about 10 square centimeters to about 50 square centimeters, about 10 square centimeters to about 40 square centimeters, about 10 square centimeters to about 30 square centimeters, about 10 square centimeters to about 20 square centimeters, about 50 square centimeters to about 1000 square centimeters, about 50 square centimeters to about 900 square centimeters, about 50 square centimeters to about 800 square centimeters, about 50 square centimeters to about 700 square centimeters, about 50 square centimeters to about 600 square centimeters, about 50 square centimeters to about 500 square centimeters, about 50 square centimeters to about 400 square centimeters, about 50 square centimeters to about 300 square centimeters, about 50 square centimeters to about 200 square centimeters, about 50 square centimeters to about 100 square centimeters, about 75 square centimeters to about 1000 square centimeters, about 75 square centimeters to about 900 square centimeters, about 75 square centimeters to about 800 square centimeters, about 75 square centimeters to about 700 square centimeters, about 75 square centimeters to about 600 square centimeters, about 75 square centimeters to about 500 square centimeters, about 75 square centimeters to about 400 square centimeters, about 75 square centimeters to about 300 square centimeters, about 75 square centimeters to about 200 square centimeters, about 75 square centimeters to about 100 square centimeters, about 100 square centimeters to about 1000 square centimeters, about 100 square centimeters to about 900 square centimeters, about 100 square centimeters to about 800 square centimeters, about 100 square centimeters to about 700 square centimeters, about 100 square centimeters to about 600 square centimeters, about 100 square centimeters to about 500 square centimeters, about 100 square centimeters to about 400 square centimeters, about 100 square centimeters to about 300 square centimeters, about 100 square centimeters to about 200 square centimeters, about 250 square centimeters to about 1000 square centimeters, about 250 square centimeters to about 900 square centimeters, about 250 square centimeters to about 800 square centimeters, about 250 square centimeters to about 700 square centimeters, about 250 square centimeters to about 600 square centimeters, about 250 square centimeters to about 500 square centimeters, about 250 square centimeters to about 400 square centimeters, about 250 square centimeters to about 300 square centimeters, about 500 square centimeters to about 1000 square centimeters, about 500 square centimeters to about 900 square centimeters, about 500 square centimeters to about 800 square centimeters, about 500 square centimeters to about 700 square centimeters, about 500 square centimeters to about 600 square centimeters, about 750 square centimeters to about 1000 square centimeters, about 750 square centimeters to about 900 square centimeters, about 750 square centimeters to about 800 square centimeters, or a range between any two of these values. Specific examples of the dissolvable microneedle patch range in size from about 1000 square centimeters, about 900 square centimeters, about 800 square centimeters, about 700 square centimeters, about 600 square centimeters, about 500 square centimeters, about 400 square centimeters, about 300 square centimeters, about 200 square centimeters, about 100 square centimeters, about 90 square centimeters, about 80 square centimeters, about 70 square centimeters, about 60 square centimeters, about 50 square centimeters, about 40 square centimeters, about 30 square centimeters, about 20 square centimeters, about 10 square centimeters, about 5 square centimeters, about 4 square centimeters, about 3 square centimeters, about 2 square centimeters, about 1 square centimeters, about 0.9 square centimeters, about 0.8 square centimeters, about 0.7 square centimeters, about 0.6 square centimeters, about 0.7 square centimeters, about 0.6 square centimeters, about 0.5 square centimeters, about 0.4 square centimeters, about 0.3 square centimeters, about 0.2 square centimeters, about 0.1 square centimeters, or a range between any two of these values.

In some embodiments, the dissolvable microneedle patch comprises a backing layer and a microneedle layer. In some embodiments, the dissolvable microneedle patch comprises a backing layer and a microneedle layer wherein the microneedle layer is placed directly on top of the skin. In some embodiments, the dissolvable microneedle patch comprises a backing layer wherein the backing layer is composed of adhesive medical tape. In some embodiments, the dissolvable microneedle patch comprises a backing layer wherein the backing layer comprises a therapeutically active ingredient.

In some embodiments, the dissolvable microneedle patch comprises a backing layer wherein the backing layer is a removable substrate. In some embodiments, the dissolvable microneedle patch wherein the removable substrate comprises an adhesive medical tape. In some embodiments, the backing layer comprises a quick dissolving polymer. In some embodiments, the dissolvable microneedle patch wherein the removable substrate comprises a therapeutically active ingredient dispersed in a polymer. In some embodiments, the dissolvable microneedle patch wherein the plurality of microneedles are attached to the removable substrate and comprise a tapered tip that extends away from the removal substrate. In some embodiments, the dissolvable microneedle patch wherein the removable substrate releases at least about 90% of the microneedles from the adhesive surface within a period of about 20 minutes after application to skin. In some embodiments, the dissolvable microneedle patch wherein the removable substrate releases at least about 90% of the microneedles from the adhesive surface within a period of about 5 minutes after application to skin. In some embodiments, the dissolvable microneedle patch wherein 90% of the microneedles are released from the adhesive surface within a period of about 0 minutes to about 20 minutes, about 0 minutes to about 15 minutes, about 0 minutes to about 10 minutes, about 0 minutes to about 9 minutes, about 0 minutes to about 8 minutes, about 0 minutes to about 7 minutes, about 0 minutes to about 6 minutes, about 0 minutes to about 5 minutes, about 0 minutes to about 4 minutes, about 0 minutes to about 3 minutes, about 0 minutes to about 2 minutes, about 0 minutes to about 1 minutes, about 1 minute to about 20 minutes, about 1 minute to about 15 minutes, about 1 minute to about 10 minutes, about 1 minute to about 9 minutes, about 1 minute to about 8 minutes, about 1 minute to about 7 minutes, about 1 minute to about 6 minutes, about 1 minute to about 5 minutes, about 1 minute to about 4 minutes, about 1 minute to about 3 minutes, about 1 minute to about 2 minutes, about 2 minutes to about 20 minutes, about 2 minutes to about 15 minutes, about 2 minutes to about 10 minutes, about 2 minutes to about 9 minutes, about 2 minutes to about 8 minutes, about 2 minutes to about 7 minutes, about 2 minutes to about 6 minutes, about 2 minutes to about 5 minutes, about 2 minutes to about 4 minutes, about 2 minutes to about 3 minutes, about 5 minutes to about 20 minutes, about 5 minutes to about 15 minutes, about 5 minutes to about 10 minutes, about 5 minutes to about 9 minutes, about 5 minutes to about 8 minutes, about 5 minutes to about 7 minutes, about 5 minutes to about 6 minutes, about 10 minutes to about 20 minutes, about 10 minutes to about 15 minutes, about 15 minutes to about 20 minutes, about 0 seconds to about 60 seconds, about 0 seconds to about 0 seconds to about 45 seconds, about 0 seconds to about 30 seconds, about 0 seconds to about 15 seconds, about 0 seconds to about 10 seconds, about 0 seconds to about 9 seconds, about 0 seconds to about 8 seconds, about 0 seconds to about 7 seconds, about 0 seconds to about 6 seconds, about 0 seconds to about 5 seconds, about 0 seconds to about 4 seconds, about 0 seconds to about 3 seconds, about 0 seconds to about 2 seconds, about 0 seconds to about 1 seconds, about 1 second to about 60 seconds, about 1 second to about 45 seconds, about 1 second to about 30 seconds, about 1 second to about 15 seconds, about 1 second to about 10 seconds, about 1 second to about 9 seconds, about 1 second to about 8 seconds, about 1 second to about 7 seconds, about 1 second to about 6 seconds, about 1 second to about 5 seconds, about 1 second to about 4 seconds, about 1 second to about 3 seconds, about 1 second to about 2 seconds, about 2 seconds to about 60 seconds, about 2 seconds to about 45 seconds, about 2 seconds to about 30 seconds, about 2 seconds to about 15 seconds, about 2 seconds to about 10 seconds, about 2 seconds to about 9 seconds, about 2 seconds to about 8 seconds, about 2 seconds to about 7 seconds, about 2 seconds to about 6 seconds, about 2 seconds to about 5 seconds, about 2 seconds to about 4 seconds, about 2 seconds to about 3 seconds, about 5 seconds to about 60 seconds, about 5 seconds to about 45 seconds, about 5 seconds to about 30 seconds, about 5 seconds to about 15 seconds, about 5 seconds to about 10 seconds, about 5 seconds to about 9 seconds, about 5 seconds to about 8 seconds, about 5 seconds to about 7 seconds, about 5 seconds to about 6 seconds, about 10 seconds to about 60 seconds, about 10 seconds to about 45 seconds, about 10 seconds to about 30 seconds, about 10 seconds to about 15 seconds, about 15 seconds to about 60 seconds, about 15 seconds to about 45 seconds, about 15 seconds to about 30 seconds, about 30 seconds to about 60 seconds, about 30 seconds to about 45 seconds, about 45 seconds to about 60 seconds, or a value within these ranges. In specific examples, 90% of the microneedles are released from the adhesive surface of the dissolvable microneedle patch within about 20 minutes, about 15 minutes, about 10 minutes, about 9 minutes, about 8 minutes, about 7 minutes, about 6 minutes, about 5 minutes, about 4 minutes, about 3 minutes, about 2 minutes, about 1 minute, about 60 seconds, about 45 seconds, about 30 seconds, about 15 seconds, about 10 seconds, about 9 seconds, about 8 seconds, about 7 seconds, about 6 seconds, about 5 seconds, about 4 seconds, about 3 seconds, about 2 seconds, about 1 second or a range between any two of these values.

In some embodiments, the dissolvable microneedle patch wherein the backing layer overlays the base of the tip portion in such a manner that each microneedle is separated from the other microneedles on the patch and forms a discrete entity when the substrate is removed upon application of the patch on the skin.

In some embodiments, the dissolvable microneedle patch is (i) placed on a surface area of the skin of a patient in need of treatment, or pre-treatment testing to assess for hypersensitivity reaction, general tolerability, or other adverse events, (ii) exerting sufficient force on the patch composition to permit the microneedles to penetrate through the epidermis into the papillary dermis, and (iii) allowing the plurality of microneedles to remain in the skin until the biodegradable polymer degrades (iv) removing the adhesive substrate from the patch composition, wherein the step (ii) is carried out by applying pressure with a finger, wherein the pressure is sufficient for a force ranging from about 0N to about 1,000N. In the preferred embodiment of the present application, the pressure applied is about 10N. In an alternate embodiment of the present application the step (ii) is carried out by impact insertion using an applicator device, wherein the pressure is sufficient for a force ranging from about 0 to about 1,000N. In the preferred embodiment of the present application, the pressure applied is about 10N. In some embodiments, the force applied by a finger or an applicator device ranges from about 0N to about 1,000 N, about 0N to about 900N, about 0N to about 800N, about 0N to about 700N, about 0N to about 600N, about 0N to about 500N, about 0N to about 400N, about 0N to about 300N, about 0N to about 200N, about 0N to about 100N, about 0N to about 90N, about 0N to about 80N, about 0N to about 70N, about 0N to about 60N, about 0N to about 50N, about 0N to about 40N, about 0N to about 30N, about 0N to about 20N, about 0N to about 10N, about 0N to about 9N, about 0N to about 8N, about 0N to about 7N, about 0N to about 6N, about 0N to about 5N, about 0N to about 4N, about 0N to about 3N, about 0N to about 2N, about 0 N to about 1N, about 0N to about 0.9N, about 0N to about 0.8N, about 0N to about 0.7N, about 0N to about 0.6N, about 0N to about 0.5N, about 0N to about 0.4N, about 0N to about 0.3N, about 0N to about 0.2N, about 0N to about 0.1N, about 0.1N to about 1000N, about 0.1N to about 900N, about 0.1 N to about 800N, about 0.1N to about 700N, about 0.1N to about 600N, about 0.1N to about 500N, about 0.1N to about 400N, about 0.1N to about 300N, about 0.1N to about 200N, about 0.1N to about 100N, about 0.1N to about 90N, about 0.1N to about 80N, about 0.1N to about 70N, about 0.1N to about 60N, about 0.1N to about 50N, about 0.1N to about 40N, about 0.1N to about 30N, about 0.1N to about 20N, about 0.1N to about 10N, about 9N, about 0.1N to about 8N, about 0.1N to about 7N, about 0.1N to about 6N, about 0.1N to about 5N, about 0.1N to about 4N, about 0.1N to about 3N, about 0.1N to about 2N, about 0.1N to about 1N, about 0.1N to about 0.9N, about 0.1N to about 0.8N, about 0.1N to about 0.7N, about 0.1N to about 0.6N, about 0.1N to about 0.5N, about 0.1N to about 0.4N, about 0.1N to about 0.3N, about 0.1N to about 0.2N, about 1N to about 1000N, about 1N to about 900N, about 1N to about 800 N, about 1N to about 700N, about 1N to about 600N, about 1N to about 500N, about 1N to about 400N, about 1N to about 300N, about 1N to about 200N, about 1N to about 100N, about 1N to about 90N, about 1N to about 80N, about 1N to about 70N, about 1N to about 60N, about 1N to about 50N, about 1N to about 40N, about 1N to about 30N, about 1N to about 20N, about 1N to about 10N, about 1N to about 9N, about 1N to about 8N, about 1N to about 7N, about 1N to about 6N, about 1N to about 5N, about 1N to about 4N, about 1N to about 3N, about 1N to about 2N, about 10N to about 1000N, about 10N to about 900 N, about 10N to about 800N, about 10N to about 700N, about 10N to about 600N, about 10N to about 500N, about 10N to about 400N, about 10N to about 300N, about 10N to about 200N, about 10N to about 100N, about 10N to about 90N, about 10N to about 80N, about 10N to about 70N, about 10N to about 60N, about 10N to about 50N, about 10N to about 40N, about 10N to about 30N, about 10N to about 20N, about 50N to about 1000N, about 50N to about 900N, about 50N to about 800N, about 50N to about 700N, about 50N to about 600N, about 50N to about 500N, about 50N to about 400N, about 50N to about 300N, about 50N to about 200N, about 50N to about 100N, about 100N to about 1000N, about 100N to about 900N, about 100N to about 800N, about 100N to about 700N, about 100N to about 600N, about 100N to about 500N, about 100N to about 400N, about 100N to about 300N, about 100N to about 200N, about 200N to about 1000N, about 200N to about 900N, about 200N to about 800N, about 200N to about 700N, about 200N to about 600N, about 200N to about 500N, about 200N to about 400N, about 200N to about 300N, about 500N to about 1000N, about 500N to about 900N, about 500N to about 800N, about 500N to about 700N, about 500N to about 600N, or a value within these ranges. In specific examples, the force applied by a finger or an applicator device is about 0N, about 0.1N, about 0.2N, about 0.3N, about 0.4N, about 0.5N, about 0.6N, about 0.7N, about 0.8N, about 0.9N, about 1N, about 2N, about 3N, about 4N, about 5N, about 6N, about 7N, about 8N, about 9N, about 10N, about 15N, about 20N, about 30N, about 40N, about 50N, about 60N, about 70N, about 80N, about 90N, about 100N, about 200N, about 300N, about 400N, about 500N, about 600N, about 700N, about 800N, about 900N, or a range between and two of these values.

Method of Treating a Skin Condition

Embodiments of the application are directed to methods of treating a skin condition comprising applying a dissolvable microneedle patch for delivery of a therapeutically active ingredient to the skin; exerting sufficient force on the dissolvable microneedle patch to permit the microneedles to penetrate to a location selected from the group consisting of the epidermis, the dermis and the papillary dermis; removing adhesive substrate from the patch composition; and allowing the plurality of microneedles to remain in the skin until the biodegradable polymer degrades.

In some embodiments, the method of treating a skin condition comprising applying a dissolvable microneedle patch comprises a plurality of microneedles are selected from the group consisting of a length to terminate in the epidermis and a length to terminate in the reticular or papillary dermis. In some embodiments, the dissolvable microneedle patch comprises a plurality of microneedles with one to five different lengths. In some embodiments, the dissolvable microneedle patch comprises a plurality of microneedles wherein the at least two varying lengths may be different based on the location on the body, patient age, or the skin condition to be treated. In some embodiments, the needles of at least two different lengths are of equal proportion. In some embodiments, the needles of at least two different lengths can be of different proportions. In an alternate embodiment, the dissolvable microneedle patch comprises a plurality of microneedles wherein the microneedles are of a single length. In some embodiments, the dissolvable microneedle patch comprises a plurality of microneedles wherein the microneedles are of equal lengths. In some embodiments, the dissolvable microneedle patch comprises a plurality of microneedles wherein the length of the plurality of microneedles range from about 10 microns to about 1000 microns, about 10 microns to about 900 microns, about 10 microns to about 800 microns, about 10 microns to about 700 microns, about 10 microns to about 600 microns, about 10 microns to about 500 microns, about 10 microns to about 400 microns, about 10 microns to about 300 microns, about 10 microns to about 200 microns, about 10 microns to about 100 microns, about 10 microns to about 90 microns, about 10 microns to about 80 microns, about 10 microns to about 70 microns, about 10 microns to about 60 microns, about 10 microns to about 50 microns, about 10 microns to about 40 microns, about 10 microns to about 30 microns, about 10 microns to about 20 microns, about 10 microns to about 15 microns, about 20 microns to about 1000 microns, about 20 microns to about 900 microns, about 20 microns to about 800 microns, about 20 microns to about 700 microns, about 20 microns to about 600 microns, about 20 microns to about 500 microns, about 20 microns to about 400 microns, about 20 microns to about 300 microns, about 20 microns to about 200 microns, about 20 microns to about 100 microns, about 20 microns to about 90 microns, about 20 microns to about 80 microns, about 20 microns to about 70 microns, about 20 microns to about 60 microns, about 20 microns to about 50 microns, about 20 microns to about 40 microns, about 20 microns to about 30 microns, about 20 microns to about 25 microns, about 50 microns to about 1000 microns, about 50 microns to about 900 microns, about 50 microns to about 800 microns, about 50 microns to about 700 microns, about 50 microns to about 600 microns, about 50 microns to about 500 microns, about 50 microns to about 400 microns, about 50 microns to about 300 microns, about 50 microns to about 200 microns, about 50 microns to about 100 microns, about 100 microns to about 1000 microns, about 100 microns to about 900 microns, about 100 microns to about 800 microns, about 100 microns to about 700 microns, about 100 microns to about 600 microns, about 100 microns to about 500 microns, about 100 microns to about 400 microns, about 100 microns to about 300 microns, about 100 microns to about 200 microns, about 200 microns to about 1000 microns, about 200 microns to about 900 microns, about 200 microns to about 800 microns, about 200 microns to about 700 microns, about 200 microns to about 600 microns, about 200 microns to about 500 microns, about 200 microns to about 400 microns, about 200 microns to about 300 microns, about 500 microns to about 1000 microns, about 500 microns to about 900 microns, about 500 microns to about 800 microns, about 500 microns to about 700 microns, about 500 microns to about 600 microns, about 800 microns to about 1000 microns, about 800 microns to about 900 microns, about 900 microns to about 1000 microns, or a value within these ranges.

In some embodiments, the method of treating a skin condition comprising applying a dissolvable microneedle patch comprising a plurality of microneedles wherein the microneedles are tapered to a point to facilitate the insertion of the microneedles into the skin. In some embodiments, the dissolvable microneedle patch comprises a plurality of microneedles wherein the microneedles have a tapered tip portion containing a therapeutically active ingredient dispersed in a matrix or suspension of a biodegradable polymer.

In some embodiments, the method of treating a skin condition comprising applying a dissolvable microneedle patch comprising a plurality of microneedles comprising microneedles of at least two different lengths are composed of equal volumes of biodegradable polymer. In some embodiments, the dissolvable microneedle patch comprises a plurality of microneedles wherein the volume of each microneedle may remain constant which is achieved by changing the diameter of each of the microneedles as required. In some embodiments, the dissolvable microneedle patch comprises a plurality of microneedles wherein the volume of each microneedle is unequal. In some embodiments, the dissolvable microneedle patch comprises a plurality of microneedles wherein the volume will depend on the concentration of the specific immune stimulants used.

In some embodiments, the method of treating a skin condition comprising applying a dissolvable microneedle patch comprising a plurality of microneedles wherein the tip portion constitutes 5-99% of the total volume of the microneedle. In some embodiments, the microneedle tip portion constitutes about 20% to about 90% of the total volume of the microneedle. In some embodiments, the microneedle tip portion constitutes about 50% of the total volume of the microneedle. In some embodiments, the microneedle tip portion constitutes about 75% of the total volume of the microneedle. In some embodiments, the microneedle tip portion constitutes about 5% to about 99%, about 5% to about 95%, about 5% to about 90%, about 5% to about 85%, about 5% to about 80%, about 5% to about 75%, about 5% to about 70%, about 5% to about 60%, about 5% to about 50%, about 5% to about 40%, about 5% to about 30%, about 5% to about 20%, about 5% to about 15%, about 5% to about 10%, about 10% to about 99%, about 10% to about 95%, about 10% to about 90%, about 10% to about 85%, about 10% to about 80%, about 10% to about 75%, about 10% to about 70%, about 10% to about 60%, about 10% to about 50%, about 10% to about 40%, about 10% to about 30%, about 10% to about 20%, about 10% to about 15%, about 15% to about 99%, about 15% to about 95%, about 15% to about 90%, about 15% to about 85%, about 15% to about 80%, about 15% to about 75%, about 15% to about 70%, about 15% to about 60%, about 15% to about 50%, about 15% to about 40%, about 15% to about 30%, about 15% to about 20%, about 25% to about 99%, about 25% to about 95%, about 25% to about 90%, about 25% to about 85%, about 25% to about 80%, about 25% to about 75%, about 25% to about 70%, about 25% to about 60%, about 25% to about 50%, about 25% to about 40%, about 25% to about 30%, about 50% to about 99%, about 50% to about 95%, about 50% to about 90%, about 50% to about 85%, about 50% to about 80%, about 50% to about 75%, about 50% to about 70%, about 50% to about 60%, about 60% to about 99%, about 60% to about 95%, about 60% to about 90%, about 60% to about 85%, about 60% to about 80%, about 60% to about 75%, about 60% to about 70%, about 70% to about 99%, about 70% to about 95%, about 70% to about 90%, about 70% to about 85%, about 70% to about 80%, about 70% to about 75%, about 80% to about 99%, about 80% to about 95%, about 80% to about 90%, about 80% to about 85%, about 90% to about 99%, about 90% to about 95%, or a value within these ranges. Specific examples may include about 99%, about 95%, about 90%, about 85%, about 80%, about 75%, about 70%, about 65%, about 60%, about 55%, about 50%, about 45%, about 40%, about 35%, about 30%, about 25%, about 20% about 15%, about 10%, about 9%, about 8%, about 7%, about 6%, about 5%, or a range between any two of these values. In some embodiments, the plurality of microneedles comprise a therapeutically active ingredient. In some embodiments, the plurality of microneedles each comprise about the same amount of the therapeutically active ingredient. In some embodiments, the plurality of microneedles each comprise different amounts of the therapeutically active ingredient.

In some embodiments, the method of treating a skin condition comprising applying a dissolvable microneedle patch wherein the skin condition is a wart, condyloma acuminatum, Bowenoid papulosis, molluscum contagiosum, actinic keratosis, squamous cell carcinoma, basal cell carcinoma, verrucous carcinoma, epidermodysplasia verruciformis, and alopecia areata, vitiligo.

Certain compounds disclosed herein may possess useful immune stimulating activity and may be used in the treatment or prophylaxis of a disease or condition in which the immune system can play an active role. In some embodiments, successful delivery of immune stimulant results in classic clinical signs of inflammation such as, rubor, tumor, and calor (redness, swelling and warmth, respectively). Thus, embodiments are also directed to pharmaceutical compositions comprising one or more compounds disclosed herein together with a pharmaceutically acceptable carrier, as well as methods of making and using the compounds and compositions. Certain embodiments are directed to methods for stimulating the immune system. Other embodiments are directed to methods for treating a skin condition in a patient in need of such treatment, comprising administering to said patient a therapeutically effective amount of a compound or composition according to the present invention. Also provided is the use of certain compounds disclosed herein in the manufacture of a medicament for the treatment of a disease or condition ameliorated by the activation of the immune system.

In some embodiments, a method of treating a skin condition by administering a pharmaceutical composition of embodiments disclosed herein. In some embodiments, the compound is in a therapeutically effective amount. In some embodiments, the therapeutically effective amount is an amount disclosed herein. In some embodiments, administration of the dissolvable microneedle patch leads to a disappearance of the conditions being treated. In some embodiments, administration of the dissolvable microneedle patch leads to disappearance of the skin lesion or skin lesions in direct contact with the dissolvable microneedle patch. In some embodiments, administration of the dissolvable microneedle patch leads to the disappearance of the skin lesion or skin lesions adjacent to the dissolvable microneedle patch.

In some embodiments, the method of treating a skin condition comprising a plurality of microneedles comprising a therapeutically active ingredient wherein therapeutically active ingredient is selected from the group consisting of a vaccine, an immune stimulating molecule, immune stimulating organism, and an immune stimulating protein. In some embodiments, the dissolvable microneedle patch delivers the therapeutically active ingredient to stimulate a local immune response. In some embodiments, the therapeutically active ingredient is a vaccine, wherein the vaccine is selected from the group consisting of measles-mumps-rubella vaccine, mumps vaccine, *Bacillus* Calmette-Guérin vaccine, human papilloma virus vaccine, and *Mycobacterium w* vaccine. In some embodiments, the therapeutically active ingredient is an immune stimulating molecule, wherein the immune stimulating molecule is imiquimod. In some embodiments, the therapeutically active ingredient is an immune stimulating organism, wherein the immune stimulating organism is *Corynebacterium parvus, Cutibacterium acnes, Propionibacterium,* and/or *Mycobacterium indicus pranii* (formerly *Mycobacterium w*). In some embodiments, the therapeutically active ingredient is an immune stimulating protein, wherein the immune stimulating protein is selected from the group consisting of *Candida* antigen, *Trichophyton* antigen, tuberculin, purified protein derivative (also), human papilloma virus surface proteins, interferon alpha, interferon beta, and interferon gamma.

In some embodiments, the method of treating a skin condition comprising a plurality of microneedles comprising a therapeutically active ingredient wherein therapeutically active ingredient is *Candida* antigen. In some embodiments, the therapeutically active ingredient is *Candida* antigen. In some embodiments, the *Candida* antigen is substantially free of glycerin. In some embodiments, the *Candida* antigen is glycerin free. In some embodiments, the glycerin free *Candida* antigen is lyophilized.

In some embodiments, the method of treating a skin condition comprising a plurality of microneedles comprising a therapeutically active ingredient wherein therapeutically active ingredient is dispersed throughout the polymer. In some embodiments, the plurality of microneedles comprise a therapeutically active ingredient wherein the therapeutically active ingredient is evenly distributed throughout the microneedle. In some embodiments, the plurality of microneedles comprise a therapeutically active ingredient wherein the therapeutically active ingredient is concentrated at the tip of the microneedle. In some embodiments, the plurality of microneedles comprise a microneedle with essentially no therapeutically active ingredient in the half of the microneedle closest to the base. In some embodiments, the plurality of microneedles comprise a microneedle with no therapeutically active ingredient in the half of the microneedle closest to the base. In some embodiments, the therapeutically active ingredient is a solid powder. In some embodiments, the therapeutically active ingredient is a solid powder dispersed throughout the polymer. In some embodiments, the therapeutically active ingredient is lyophilized. In some embodiments, the therapeutically active ingredient is lyophilized and dispersed throughout the polymer.

Some embodiments disclosed herein also include pharmaceutical compositions which contain, as the active ingredient, one or more of the compounds disclosed herein in combination with one or more pharmaceutically acceptable carriers (excipients).

The active compound can be effective over a wide dosage range and can be generally administered in a therapeutically effective amount. It will be understood, however, that the amount of the compound actually administered will usually be determined by a physician, according to the relevant circumstances, including the condition to be treated, the actual compound administered, the age, weight, and response of the individual patient, the severity of the patient's symptoms, and the like. In some embodiments, the plurality of microneedles will contain equal amounts of therapeutically active ingredient. In some embodiments, the plurality of microneedles will contain unequal amounts of therapeutically active ingredient.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. In some embodiments, that condition is selected from a wart, condyloma acuminatum, Bowenoid papulosis, molluscum contagiosum, actinic keratosis, squamous cell carcinoma, basal cell carcinoma, verrucous carcinoma, epidermodysplasia verruciformis and successful treatment of these conditions results in a one point improvement on any ordinal or interval assessment scale, such as the Physician Global Assessment or the Investigator Global Assessment. In some embodiments, the condition is selected from a wart, condyloma acuminatum, Bowenoid papulosis, molluscum contagiosum, actinic keratosis, squamous cell carcinoma, basal cell carcinoma, verrucous carcinoma, epidermodysplasia verruciformis and successful treatment of these conditions results in about 100% loss of skin lesions by clinical, histopathological, or dermatoscopic assessment as well as assessment by optical coherence tomography or confocal microscopy in the location of the patch is administered. In some embodiments, the condition is selected from a wart, condyloma acuminatum, Bowenoid papulosis, molluscum contagiosum, actinic keratosis, squamous cell carcinoma, basal cell carcinoma, verrucous carcinoma, epidermodysplasia verruciformis and successful treatment of these conditions results in about 50% loss of skin lesions by clinical, histopathological, or dermatoscopic assessment as well as assessment by optical coherence tomography or confocal microscopy in the location of the patch is administered. In some embodiments, successful treatment of a wart, condyloma acuminatum, Bowenoid papulosis, molluscum contagiosum, actinic keratosis, squamous cell carcinoma, basal cell carcinoma, verrucous carcinoma, epidermodysplasia verruciformis with the dissolvable microneedle patch results in reduction of skin lesions in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include reducing skin lesions, by clinical, histopathological, or dermatoscopic assessment as well as assessment by optical coherence tomography or confocal microscopy by about 100%, about 99%, about 95%, about 90%, about 85%, about 80%, about 75%, about 70%, about 65%, about 60%, about 55%, about 50% or a range between any two of these values.

In some embodiments, the method of treating a skin condition comprising the successful treatment of a wart, condyloma acuminatum, Bowenoid papulosis, molluscum contagiosum, actinic keratosis, squamous cell carcinoma, basal cell carcinoma, verrucous carcinoma, epidermodysplasia verruciformis with the dissolvable microneedle patch results in reduction of in the width, length, or height of skin lesions in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include reducing the width, length, or height of skin lesions measured by clinical, histopathological, or dermatoscopic assessment as well as assessment by optical coherence tomography or confocal microscopy by about 100%, about 99%, about 95%, about 90%, about 85%, about 80%, about 75%, about 70%, about 65%, about 60%, about 55%, about 50% or a range between any two of these values.

In some embodiments, the method of treating the skin condition alopecia areata with a dissolvable microneedle patch, wherein successful treatment of this condition results in a one point improvement on any ordinal or interval assessment scale, such as the Physician Global Assessment or the Investigator Global Assessment. In some embodiments, the condition is alopecia areata and successful treatment of this condition results in about 100% restoration of hair growth in the location of the patch is administered. In some embodiments, the condition is alopecia areata and successful treatment of this condition results in at least about 50% increase in hair growth as defined by number of hair follicles with actively growing hair shafts as seen with clinical, trichoscopic, or histopathological assessment in the location of the patch is administered. In some embodiments, successful treatment of alopecia areata with the dissolvable microneedle patch results in an increase in hair growth in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include increasing hair growth as defined by the number of hair follicles with actively growing hair shafts as seen with clinical, trichoscopic, or histopathologic assessment, by about 100%, about 99%, about 95%, about 90%, about 85%, about 80%, about 75%, about 70%, about 65%, about 60%, about 55%, about 50% or a range between any two of these values.

In some embodiments, the method of treating the skin condition alopecia areata with a dissolvable microneedle patch, wherein successful treatment results in improvement in the Severity Alopecia Tool (SALT) score in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include improving the Severity Alopecia Tool (SALT) score by about 100%, about 99%, about 95%, about 90%, about 85%, about 80%, about 75%, about 70%, about 65%, about 60%, about 55%, about 50% or a range between any two of these values.

In some embodiments, the method of treating a skin condition with a dissolvable microneedle patch, wherein each dissolvable microneedle patch contains a standardized amount of therapeutically active ingredient.

In some embodiments, the method of treating a skin condition with a dissolvable microneedle patch, wherein the dissolvable microneedles may comprise about 1% to about 90% of one or more therapeutically active ingredients disclosed herein. In some embodiments, the dissolvable microneedles may comprise about 50% to about 75% of one or more therapeutically active ingredients disclosed herein. In some embodiments, the dissolvable microneedles may comprise about 25% to about 50% of one or more therapeutically active ingredients disclosed herein. In some embodiments, the dissolvable microneedles may comprise about 25% to about 75% of one or more therapeutically active ingredients disclosed herein. In some embodiments, the dissolvable microneedles may comprise about 40% to about 60% of one or more therapeutically active ingredients disclosed herein. In some embodiments, the dissolvable microneedles may comprise about 60% to about 80% of one or more therapeutically active ingredients disclosed herein. In some embodiments, the one or more therapeutically active ingredients are in an amount of about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45% about 15% to about 40%, about 15% to about 35%, about 15% to about 30%, about 15% to about 25%, about 15% to about 20%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 35% to about 90%, about 35% to about 85%, about 35% to about 80%, about 35% to about 75%, about 35% to about 70%, about 35% to about 65%, about 35% to about 60%, about 35% to about 55%, about 35% to about 50%, about 35% to about 45%, about 35% to about 40%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 45% to about 90%, about 45% to about 85%, about 45% to about 80%, about 45% to about 75%, about 45% to about 70%, about 45% to about 65%, about 45% to about 60%, about 45% to about 55%, about 45% to about 50%, about 50% to about 90%, about 50% to about 85%, about 50% to about 80%, about 50% to about 75%, about 50% to about 70%, about 50% to about 65%, about 50% to about 60%, about 50% to about 55%, about 55% to about 90%, about 55% to about 85%, about 55% to about 80%, about 55% to about 75%, about 55% to about 70%, about 55% to about 65%, about 55% to about 60%, about 60% to about 90%, about 60% to about 85%, about 60% to about 80%, about 60% to about 75%, about 60% to about 70%, about 60% to about 65%, about 65% to about 90%, about 65% to about 85%, about 65% to about 80%, about 65% to about 75%, about 65% to about 70%, about 70% to about 90%, about 70% to about 85%, about 70% to about 80%, about 70% to about 75%, about 75% to about 90%, about 75% to about 85%, about 75% to about 80%, about 80% to about 90%, about 80% to about 85%, about 85% to about 90%, or a value within one of these ranges. Specific examples may include about 90%, about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 9%, about 8%, about 7%, about 6%, about 5%, about 4% about 3%, about 2%, about 1%. The foregoing all representing weight percentages of the pharmaceutical composition. In some embodiments, the pharmaceutical composition is suitable for transdermal administration.

In some embodiments, the method of treating a skin condition with a dissolvable microneedle patch comprising a therapeutically active ingredient, wherein the therapeutically active ingredient is in a therapeutically effective amount. In some embodiments, the therapeutically effective amount may be about 1 microgram to 999 micrograms, 1 microgram to 100 micrograms, 100 micrograms to 200 micrograms, 200 micrograms to 300 micrograms, 300 micrograms to 400 micrograms, 400 micrograms to 500 micrograms, 500 micrograms to 600 micrograms, 600 micrograms to 700 micrograms, 700 micrograms to 800 micrograms, 800 micrograms to 900 micrograms, 900 micrograms to 999 micrograms, 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg, or any value between the ranges disclosed above.

In some embodiments, the method of treating a skin condition with a dissolvable microneedle patch comprising a therapeutically effective amount of active ingredient, the therapeutically effective amount can vary according to, for example, the particular use for which the treatment is made, the location of administration of the microneedle patch, the health and condition of the patient, and the judgment of the prescribing physician. The proportion or concentration of a compound in a dissolvable microneedle can vary depending upon a number of factors including dosage, chemical characteristics (e.g., hydrophobicity), and the type of microneedle polymer. The dosage is likely to depend on such variables as the type and extent of progression of the disease or disorder, the overall health status of the particular patient, the relative biological efficacy of the compound selected, composition of the excipient, and its location of administration. Effective doses can be extrapolated from dose-response curves derived from in vitro or animal model test systems.

In some embodiments, the method of treating a skin condition comprising applying a dissolvable microneedle patch comprises a plurality of microneedles, wherein the microneedles comprise a biodegradable polymer. In some embodiments, the dissolvable microneedle patch comprises a plurality of microneedles, wherein the microneedles comprise poly(lactic-co-glycolic acid) (PLGA). In some embodiments, the dissolvable microneedle patch comprises a plurality of microneedles, wherein the microneedles comprise a polymer selected from PLGA (poly(lactic-co-glycolic acid)), polyglycolic acid, fibroin, PLA (polylactic acid), PVP (polyvinylpyrrolidone) or PCL (polycaprolactone). In some embodiments, the dissolvable microneedle patch comprises a plurality of microneedles, wherein the microneedles comprise a single biodegradable polymer. In some embodiments, the dissolvable microneedle patch comprises a plurality of microneedles, wherein the microneedles comprise two biodegradable polymers. In some embodiments, the dissolvable microneedle patch comprises a plurality of microneedles, wherein the microneedles comprise a plurality of biodegradable polymers.

In some embodiments, the method of treating a skin condition comprising applying a dissolvable microneedle patch comprising a biodegradable polymer, wherein the biodegradable polymer is capable of providing immediate release of a therapeutically active ingredient after insertion of the microneedle patch into the skin. In further embodiments, the immediate release biodegradable polymer is water soluble and comprises carboxy methylcellulose, chondroitin sulfate, dextran, dextrin, polyvinylpyrrolidone, maltose, trehalose, sucrose, galactose, amylopectin, polyvinyl alcohol, and/or polyvinylpyrrolidone-methacrylic acid. In further embodiments, the immediate release biodegradable polymer releases the therapeutically active ingredient within about 0 hours to about 24 hours after insertion of the microneedle patch to the skin. In some embodiments, the immediate release biodegradable polymer releases at least about 75% of the therapeutically active ingredient on a timescale of about 0 hours to about 24 hours. In some embodiments, the immediate release biodegradable polymer releases about 100% of the therapeutically active ingredient on a timescale of about 0 hours to about 24 hours. In some embodiments, the immediate release biodegradable polymer releases therapeutically active ingredient on a timescale of about 0 hours to about 24 hours in a range of about 75% to about 100%, about 75% to about 95%, about 75% to about 90%, about 75% to about 85%, about 75% to about 80%, about 80% to about 100%, about 80% to about 95%, about 80% to about 90%, about 80% to about 85%, about 85% to about 100%, about 85% to about 95%, about 85% to about 90%, about 90% to about 100%, about 90% to about 95%, about 95% to about 100%, or a value within these ranges. Specific examples may include about 75%, about 80%, about 85%, about 90%, about 95%, about 99%, about 100%, or a range between any two of these values.

In some embodiments, the immediate release biodegradable polymer releases the therapeutically active ingredient within about 0 hours to about 24 hours after insertion of the microneedle patch to the skin. In some embodiments, the immediate release biodegradable polymer releases the therapeutically active ingredient within about 0 minutes to about 10 minutes after insertion of the microneedle patch to the skin. In some embodiments, the immediate release biodegradable polymer releases the therapeutically active ingredient within about 0 minutes to about 5 minutes after insertion of the microneedle patch to the skin. In some embodiments, the immediate release biodegradable polymer releases therapeutically active ingredient within about 0 hours to about 24 hours, about 0 hours to about 23 hours, about 0 hours to about 22 hours, about 0 hours to about 21 hours, about 0 hours to about 20 hours, about 0 hours to about 18 hours, about 0 hours to about 16 hours, about 0 hours to about 14 hours, about 0 hours to about 12 hours, about 0 hours to about 10 hours, about 0 hours to about 9 hours, about 0 hours to about 8 hours, about 0 hours to about 7 hours, about 0 hours to about 6 hours, about 0 hours to about 5 hours, about 0 hours to about 4 hours, about 0 hours to about 3 hours, about 0 hours to about 2 hours, about 0 hours to about 1 hour, about 1 hour to about 24 hours, about 1 hour to about 23 hours, about 1 hour to about 22 hours, about 1 hour to about 21 hours, about 1 hour to about 20 hours, about 1 hour to about 18 hours, about 1 hour to about 16 hours, about 1 hour to about 14 hours, about 1 hour to about 12 hours, about 1 hour to about 10 hours, about 1 hour to about 9 hours, about 1 hour to about 8 hours, about 1 hour to about 7 hours, about 1 hour to about 6 hours, about 1 hour to about 5 hours, about 1 hour to about 4 hours, about 1 hour to about 3 hours, about 1 hour to about 2 hours, about 2 hours to about 24 hours, about 2 hours to about 23 hours, about 2 hours to about 22 hours, about 2 hours to about 21 hours, about 2 hours to about 20 hours, about 2 hours to about 18 hours, about 2 hours to about 16 hours, about 2 hours to about 14 hours, about 2 hours to about 12 hours, about 2 hours to about 10 hours, about 2 hours to about 9 hours, about 2 hours to about 8 hours, about 2 hours to about 7 hours, about 2 hours to about 6 hours, about 2 hours to about 5 hours, about 2 hours to about 4 hours, about 2 hours to about 3 hours, about 5 hours to about 24 hours, about 5 hours to about 23 hours, about 5 hours to about 22 hours, about 5 hours to about 21 hours, about 5 hours to about 20 hours, about 5 hours to about 18 hours, about 5 hours to about 16 hours, about 5 hours to about 14 hours, about 5 hours to about 12 hours, about 5 hours to about 10 hours, about 5 hours to about 9 hours, about 5 hours to about 8 hours, about 5 hours to about 7 hours, about 5 hours to about 6 hours, about 12 hours to about 24 hours, about 12 hours to about 23 hours, about 12 hours to about 22 hours, about 12 hours to about 21 hours, about 12 hours to about 20 hours, about 12 hours to about 18 hours, 12 hours to about 16 hours, about 12 hours to about 14 hours, about 12 hours to about 13 hours, about 18 hours to about 24 hours, about 18 hours to about 23 hours, about 18 hours to about 22 hours, about 18 hours to about 21 hours, about 18 hours to about 20 hours, about 18 hours to about 19 hours, about 20 hours to about 24 hours, about 20 hours to about 23 hours, about 20 hours to about 22 hours, about 20 hours to about 21 hours, about 0 minutes to about 60 minutes, about 0 minutes to about 50 minutes, about 0 minutes to about 45 minutes, about 0 minutes to about 30 minutes, about 0 minutes to about 15 minutes, about 0 minutes to about 10 minutes, about 0 minutes to about 5 minutes, about 0 minutes to about 4 minutes, about 0 minutes to about 3 minutes, 0 minutes to about 2 minutes, 0 minutes to about 1 minute, about 5 minutes to about 60 minutes, about 5 minutes to about 50 minutes, about 5 minutes to about 45 minutes, about 5 minutes to about 30 minutes, about 5 minutes to about 15 minutes, about 5 minutes to about 10 minutes, about 10 minutes to about 60 minutes, about 10 minutes to about 50 minutes, about 10 minutes to about 45 minutes, about 10 minutes to about 30 minutes, about 10 minutes to about 15 minutes, about 15 minutes to about 60 minutes, about 15 minutes to about 50 minutes, about 15 minutes to about 45 minutes, about 15 minutes to about 30 minutes, about 15 minutes to about 25 minutes, about 15 minutes to about 20 minutes, about 30 minutes to about 60 minutes, about 30 minutes to about 50 minutes, about 30 minutes to about 45 minutes, about 30 minutes to about 40 minutes, about 30 minutes to about 35 minutes, about 45 minutes to about 60 minutes, about 45 minutes to about 50 minutes, or a value within these ranges. Specific examples may include about 24 hours, about 23 hours, about 22 hours, about 21 hours, about 20 hours, about 18 hours, about 16 hours, about 14 hours, about 12 hours, about 10 hours, about 9 hours, about 8 hours, about 7 hours, about 6 hours, about 5 hours, about 4 hours, about 3 hours, about 2 hours about 1 hour, about 60 minutes, about 55 minutes, about 50 minutes, about 45 minutes, about 40 minutes, about 35 minutes, about 30 minutes, about 25 minutes, about 20 minutes, about 15 minutes, about 10 minutes, about 9 minutes, about 8 minutes, about 7 minutes, about 6 minutes, about 5 minutes, about 4 minutes about 3 minutes, about 2 minutes, about 1 minute, or a range between any two of these values.

In some embodiments, the method of treating a skin condition comprising applying a dissolvable microneedle patch comprising a biodegradable polymer, wherein the biodegradable polymer is capable of providing sustained release of a therapeutically active ingredient after insertion of the microneedle patch into the skin. In further embodiments, the sustained release biodegradable polymer is water soluble and includes PLGA (poly(lactic-co-glycolic acid)), polyglycolic acid, fibroin, PLA (polylactic acid), PVP (polyvinylpyrrolidone), or PCL (polycaprolactone). In further embodiments, the sustained release biodegradable polymer releases the therapeutically active ingredient after about 24 hours of insertion of the microneedle patch to the skin. In some embodiments, the sustained release biodegradable polymer does not release more than 75% of the therapeutically active ingredient until a time greater than about 24 hours after insertion of the microneedle patch to the skin. In some embodiments, the sustained release biodegradable polymer does not release therapeutically active ingredient until a time greater than about 24 hours in amounts of about 75% to about 100%, about 75% to about 99%, about 75% to about 95%, about 75% to about 90%, about 75% to about 85%, about 75% to about 80%, about 80% to about 100%, about 80% to about 99%, about 80% to about 95%, about 80% to about 90%, about 80% to about 85%, about 85% to about 100%, about 85% to about 99%, 85% to about 95%, about 85% to about 90%, about 90% to about 100%, about 90% to about 99%, about 90% to about 95%, about 95% to about 100%, about 95% to about 99%, about 99% to about 100%, or a value within these ranges. Specific examples may include about 75%, about 80% about 85%, about 90%, about 95%, about 99%, about 100%.

In some embodiments, the sustained release biodegradable polymer releases the therapeutically active ingredient over about 1 day to about 30 days. In some embodiments, the sustained release biodegradable polymer releases the therapeutically active ingredient over about 2 days to about 21 days. In some embodiments the sustained release biodegradable polymer releases the therapeutically active over about 1 day to about 30 days, about 1 day to about 28 days, about 1 day to about 26 days, about 1 day to about 24 days, about 1 days to about 22 days, about 1 day to about 21 days, about 1 day to about 14 days, about 1 day to about 7 days, about 1 day to about 6 days, about 1 day to about 5 days, about 1 day to about 4 days, about 1 day to about 3 days, about 1 day to about 2 days, about 2 days to about 30 days, about 2 days to about 28 days, about 2 days to about 26 days, about 2 days to about 24 days, about 2 days to about 22 days, about 2 days to about 21 days, about 2 days to about 14 days, about 2 days to about 7 days, about 2 days to about 6 days, about 2 days to about 5 days, about 2 days to about 4 days, about 2 days to about 3 days, about 3 days to about 30 days, about 3 days to about 28 days, about 3 days to about 26 days, about 3 days to about 24 days, about 3 days to about 22 days, about 3 days to about 21 days, about 3 days to about 14 days, about 3 days to about 7 days, about 3 days to about 6 days, about 3 days to about 5 days, about 3 days to about 4 days, about 4 days to about 30 days, about 4 days to about 28 days, about 4 days to about 26 days, about 4 days to about 24 days, about 4 days to about 22 days, about 4 days to about 21 days, about 4 days to about 14 days, about 4 days to about 7 days, about 4 days to about 6 days, about 4 days to about 5 days, about 5 days to about 30 days, about 5 days to about 28 days, about 5 days to about 26 days, about 5 days to about 24 days, about 5 days to about 22 days, about 5 days to about 21 days, about 5 days to about 14 days, about 5 days to about 7 days, about 5 days to about 6 days, about 7 days to about 30 day, about 7 days to about 28 days, about 7 days to about 26 days, about 7 days to about 24 days, about 7 days to about 24 days, about 7 days to about 22 days, about 7 days to about 21 days, about 7 days to about 14 days, about 14 days to about 30 days, about 14 days to about 28 days, about 14 days to about 26 days, about 14 days to about 24 days, about 14 days to about 22 days, about 14 days to about 21 days, about 21 days to about 30 days, about 21 days to about 28 days, about 21 days to about 26 days, about 21 days to about 24 days, about 21 days to about 22 days or a value within these ranges. Specific examples may include about 30 days, about 28 days, about 26 days, about 24 days, about 22 days about 21 days, about 14 days, about 7 days, about 6 days, about 5 days, about 4 days, about 3 days, about 2 days, about 1 day or a range between any two of these values.

In some embodiments, the method of treating a skin condition comprising applying a dissolvable microneedle patch comprising a biodegradable polymer wherein the biodegradable polymer is capable of providing both sustained release and immediate release of a therapeutically active ingredient after insertion of the microneedle patch into the skin. In some embodiments, the plurality of microneedles comprise immediate release biodegradable polymer and sustained release biodegradable polymer. In some embodiments, the plurality of microneedles contain immediate release biodegradable polymer at the base of the microneedle and sustained release biodegradable polymer at the tip of the microneedle. In some embodiments, the plurality of microneedles contain immediate release biodegradable polymer at the base of the microneedle and alternating layers of immediate release biodegradable polymer and sustained release biodegradable polymer at the tip of the microneedle.

In some embodiments, the method of treating a skin condition comprising applying a dissolvable microneedle patch, wherein the dissolvable microneedle patch is applied on a skin lesion of a patient in need thereof to treat a skin condition. In some embodiments, the dissolvable microneedle patch is applied adjacent to a skin lesion of a patient in need thereof to treat a skin condition. In some embodiments, the dissolvable microneedle patch is applied to an area of the skin that is determined to be optimal based on the age of the patient. In some embodiments, the dissolvable microneedle patch is applied to an area of the skin that is determined to be optimal based on the type of skin in need of treatment.

In some embodiments, the method of treating a skin condition comprising applying a dissolvable microneedle patch comprises a plurality of microneedles, wherein the plurality of microneedles are spatially separated within the skin wherein one microneedle does not touch another microneedle. In some embodiments, the dissolvable microneedle patch comprises a plurality of microneedles, wherein the microneedle patch comprises at least about one to about 200 microneedles per square centimeter, about one to about 175 microneedles per square centimeter, about one to about 150 microneedles per square centimeter, about one to about 125 microneedles per square centimeter, about one to about 100 microneedles per square centimeter, about one to about 90 microneedles per square centimeter, about one to about 80 microneedles per square centimeter, about one to about 70 microneedles per square centimeter, about one to about 60 microneedles per square centimeter, about one to about 50 microneedles per square centimeter, about one to about 40 microneedles per square centimeter, about one to about 30 microneedles per square centimeter, about one to about 25 microneedles per square centimeter, about one to about 20 microneedles per square centimeter, about one to about 15, about one to about 10 microneedles per square centimeter, about one to about 5 microneedles per square centimeter, about 5 to about 200 microneedles per square centimeter, about 5 to about 175 microneedles per square centimeter, about 5 to about 150 microneedles per square centimeter, about 5 to about 125 microneedles per square centimeter, about 5 to about 100 microneedles per square centimeter, about 5 to about 90 microneedles per square centimeter, about 5 to about 80 microneedles per square centimeter, about 5 to about 70 microneedles per square centimeter, about 5 to about 60 microneedles per square centimeter, about 5 to about 50 microneedles per square centimeter, about 5 to about 40 microneedles per square centimeter, about 5 to about 30 microneedles per square centimeter, about 5 to about 25 microneedles per square centimeter, about 5 to about 20 microneedles per square centimeter, about 5 to about 15 microneedles per square centimeter, about 5 to about 20 microneedles per square centimeter, about 10 to about 200 microneedles per square centimeter, about 10 to about 175 microneedles per square centimeter, about 10 to about 150 microneedles per square centimeter, about 10 to about 150 microneedles per square centimeter, about 10 to about 125 microneedles per square centimeter, about 10 to about 100 microneedles per square centimeter, about 10 to about 90 microneedles per square centimeter, about 10 to about 80 microneedles per square centimeter, about 10 to about 70 microneedles per square centimeter, about 10 to about 60 microneedles per square centimeter, about 10 to about 50 microneedles per square centimeter, about 10 to about 40 microneedles per square centimeter, about 10 to about 30 microneedles per square centimeter, about 10 to about 25 microneedles per square centimeter, about 10 to about 20 microneedles per square centimeter, about 10 to about 15 microneedles per square centimeter, about 25 to about 200 microneedles per square centimeter, about 25 to about 175 microneedles per square centimeter, about 25 to about 150 microneedles per square centimeter, about 25 to about 125 microneedles per square centimeter, about 25 to about 100 microneedles per square centimeter, about 25 to about 90 microneedles per square centimeter, about 25 to about 80 microneedles per square centimeter, about 25 to about 70 microneedles per square centimeter, about 25 to about 60 microneedles per square centimeter, about 25 to about 50 microneedles per square centimeter, about 25 to about 40 microneedles per square centimeter, about 25 to about 30 microneedles per square centimeter, about 50 to about 200 microneedles per square centimeter, about 50 to about 175 microneedles per square centimeter, about 50 to about 150 microneedles per square centimeter, about 50 to about 125 microneedles per square centimeter, about 50 to about 100 microneedles per square centimeter, about 50 to about 90 microneedles per square centimeter, about 50 to about 80 microneedles per square centimeter, about 50 to about 70 microneedles per square centimeter, about 50 to about 60 microneedles per square centimeter, about 75 to about 200 microneedles per square centimeter, about 75 to about 175 microneedles per square centimeter, about 75 to about 150 microneedles per square centimeter, about 75 to about 125 microneedles per square centimeter, about 75 to about 100 microneedles per square centimeter, about 75 to about 90 microneedles per square centimeter, about 75 to about 80 microneedles per square centimeter, about 100 to about 200 microneedles per square centimeter, about 100 to about 175 microneedles per square centimeter, about 100 to about 150 microneedles per square centimeter, about 100 to about 125 microneedles per square centimeter, about 125 to about 200 microneedles per square centimeter, about 125 to about 175 microneedles per square centimeter, about 125 to about 150 microneedles per square centimeter, about 150 to about 200 microneedles per square centimeter, about 150 to about 175 microneedles per square centimeter, about 175 to about 200 microneedles per square centimeter, or a value within these ranges. Specific examples may include a dissolvable microneedle patch comprising a plurality of microneedles, wherein the microneedle patch comprises at least about 200 microneedles per square centimeter, at least about 175 microneedles per square centimeter, at least about 150 microneedles per square centimeter, at least about 125 microneedles per square centimeter, at least about 100 microneedles per square centimeter, at least about 90 microneedles per square centimeter, at least about 80 microneedles per square centimeter, at least about 70 microneedles per square centimeter, at least about 60 microneedles per square centimeter, at least about 50 microneedles per square centimeter, at least about 40 microneedles per square centimeter, at least about 30 microneedles per square centimeter, at least about 25 microneedles per square centimeter, at least about 20 microneedles per square centimeter, at least about 15 microneedles per square centimeter, at least about 10 microneedles per square centimeter, at least about 5 microneedles per square centimeter, at least about 4 microneedles per square centimeter, at least about 3 microneedles per square centimeter, at least about 2 microneedles per square centimeter, at least about 1 microneedle per square centimeter, or a range between any two of these values.

In some embodiments, the method of treating a skin condition comprising applying a dissolvable microneedle patch, wherein the dissolvable microneedle patch is any shape necessary to accommodate the surface topology of the skin. In some embodiments, the dissolvable microneedle patch has any of n number of sides with n ranging from about 0 sides to about 1000 sides. In some embodiments, the dissolvable microneedle patch has about 0 sides to about 1000 sides, about 0 sides to about 900 sides, about 0 sides to about 800 sides, about 0 sides to about 700 sides, about 0 sides to about 600 sides, about 0 sides to about 500 sides, about 0 sides to about 400 sides, about 0 sides to about 300 sides, about 0 sides to about 200 sides, about 0 sides to about 100 sides, about 0 sides to about 90 sides, about 0 sides to about 80 sides, about 0 sides to about 70 sides, about 0 sides to about 60 sides, about 0 sides to about 50 sides, about 0 sides to about 40 sides, about 0 sides to about 30 sides, about 0 sides to about 20 sides, about 0 sides to about 10 sides, about 0 sides to about 9 sides, about 0 sides to about 8 sides, about 0 sides to about 7 sides, about 0 sides to about 6 sides, about 0 sides to about 5 sides, about 0 sides to about 4 sides, about 0 sides to about 3 sides, about 0 sides to about 2 sides, about 10 sides to about 1000 sides, about 10 sides to about 900 sides, about 10 sides to about 800 sides, about 10 sides to about 700 sides, about 10 sides to about 600 sides, about 10 sides to about 500 sides, about 10 sides to about 400 sides, about 10 sides to about 300 sides, about 10 sides to about 200 sides, about 10 sides to about 100 sides, about 10 sides to about 90 sides, about 10 sides to about 80 sides, about 10 sides to about 70 sides, about 10 sides to about 60 sides, about 10 sides to about 50 sides, about 10 sides to about 40 sides, about 10 sides to about 30 sides, about 10 sides to about 20 sides, about 20 sides to about 1000 sides, about 20 sides to about 900 sides, about 20 sides to about 800 sides, about 20 sides to about 700 sides, about 20 sides to about 600 sides, about 20 sides to about 500 sides, about 20 sides to about 400 sides, about 20 sides to about 300 sides, about 20 sides to about 200 sides, about 20 sides to about 100 sides, about 20 sides to about 90 sides, about 20 sides to about 80 sides, about 20 sides to about 70 sides, about 20 sides to about 60 sides, about 20 sides to about 50 sides, about 20 sides to about 40 sides, about 20 sides to about 30 sides, about 30 sides to about 1000 sides, about 30 sides to about 900 sides, about 30 sides to about 800 sides, about 30 sides to about 700 sides, about 30 sides to about 600 sides, about 30 sides to about 500 sides, about 30 sides to about 400 sides, about 30 sides to about 300 sides, about 30 sides to about 200 sides, about 30 sides to about 100 sides, about 30 sides to about 90 sides, about 30 sides to about 80 sides, about 30 sides to about 70 sides, about 30 sides to about 60 sides, about 30 sides to about 50 sides, about 30 sides to about 40 sides, about 50 sides to about 1000 sides, about 50 sides to about 900 sides, about 50 sides to about 800 sides, about 50 sides to about 700 sides, about 50 sides to about 600 sides, about 50 sides to about 500 sides, about 50 sides to about 400 sides, about 50 sides to about 300 sides, about 50 sides to about 200 sides, about 50 sides to about 100 sides, about 50 sides to about 90 sides, about 50 sides to about 80 sides, about 50 sides to about 70 sides, about 50 sides to about 60 sides, about 75 side to about 1000 sides, about 75 to about 900 sides, about 75 to about 800 sides, about 75 to about 700 sides, about 75 to about 600 sides, about 75 to about 500 sides, about 75 to about 400 sides, about 75 to about 300 sides, about 75 to about 200 sides, about 75 to about 200 sides, about 75 to about 100 sides, about 75 to about 90 sides, about 75 to about 80 sides, about 100 sides to about 1000 sides, about 100 sides to about 900 sides, about 100 sides to about 800 sides, about 100 sides to about 700 sides, about 100 sides to about 600 sides, about 100 sides to about 500 sides, about 100 sides to about 400 sides, about 100 sides to about 300 sides, about 100 sides to about 200 sides, about 250 sides to about 1000 sides, about 250 sides to about 900 sides, about 250 sides to about 800 sides, about 250 to about 700 sides, about 250 sides to about 600 sides, about 250 sides to about 500 sides, about 250 sides to about 400 sides, about 250 sides to about 300 sides, about 500 sides to about 1000 sides, about 500 sides to about 900 sides, about 500 sides to about 800 sides, about 500 sides to about 700 sides, about 500 sides to about 600 sides, about 750 sides to about 1000 sides, about 750 sides to about 900 sides, about 750 sides to about 800 sides, about 900 sides to about 1000 sides or a value within these ranges. Specific examples may include a dissolvable microneedle patch has about 1000 sides, about 900 sides, about 800 sides, about 700 sides, about 600 sides, about 500 sides, about 400 sides, about 300 sides, about 200 sides, about 100 sides, about 90 sides, about 80 sides, about 70 sides, about 60 sides, about 50 sides, about 40 sides, about 30 sides, about 20 sides, about 10 sides, about 9 sides, about 8 sides, about 7 sides, about 6 sides, about 5 sides, about 4 sides, about 3 sides, about 2 sides, or a range between any two of these values.

In further embodiments, the method of treating a skin condition comprising applying a dissolvable microneedle patch, wherein the dissolvable microneedle patch may have sides of equal length. In further embodiments, the dissolvable microneedle patch may have sides of unequal length. In some embodiments, the dissolvable microneedle patch is shaped as a medical bandage. In some embodiments, the dissolvable microneedle patch ranges in size from about 0.1 square centimeters to about 1000 square centimeters, about 0.1 square centimeters to about 900 square centimeters, about 0.1 square centimeters to about 800 square centimeters, about 0.1 square centimeters to about 700 square centimeters, about 0.1 square centimeters to about 600 square centimeters, about 0.1 square centimeters to about 500 square centimeters, about 0.1 square centimeters to about 400 square centimeters, about 0.1 square centimeters to about 300 square centimeters, about 0.1 square centimeters to about 200 square centimeters, about 0.1 square centimeters to about 100 square centimeters, about 0.1 square centimeters to about 90 square centimeters, about 0.1 square centimeters to about 80 square centimeters, about 0.1 square centimeters to about 70 square centimeters, about 0.1 square centimeters to about 60 square centimeters, about 0.1 square centimeters to about 50 square centimeters, about 0.1 square centimeters to about 40 square centimeters, about 0.1 square centimeters to about 30 square centimeters, about 0.1 square centimeters to about 20 square centimeters, about 0.1 square centimeters to about 10 square centimeters, about 0.1 square centimeters to about 5 square centimeters, about 0.1 square centimeters to about 4 square centimeters, about 0.1 square centimeters to about 3 square centimeters, about 0.1 square centimeters to about 2 square centimeters, about 0.1 square centimeters to about 1 square centimeters, about 0.1 square centimeters to about 0.9 square centimeters, about 0.1 square centimeters to about 0.8 square centimeters, about 0.1 square centimeters to about 0.7 square centimeters, about 0.1 square centimeters to about 0.6 square centimeters, about 0.1 square centimeters to about 0.5 square centimeters, about 0.1 square centimeters to about 0.4 square centimeters, about 0.1 square centimeters to about 0.3 square centimeters, about 0.1 square centimeters to about 0.2 square centimeters, about 0.5 square centimeters to about 1000 square centimeters, about 0.5 square centimeters to about 900 square centimeters, about 0.5 square centimeters to about 800 square centimeters, about 0.5 square centimeters to about 700 square centimeters, about 0.5 square centimeters to about to about 600 square centimeters, about 0.5 square centimeters to about to about 500 square centimeters, about 0.5 square centimeters to about 400 square centimeters, about 0.5 square centimeters to about 300 square centimeters, about 0.5 square centimeters to about 200 square centimeters, about 0.5 square centimeters to about 100 square centimeters, about 0.5 square centimeters to about 90 square centimeters, about 0.5 square centimeters to about 80 square centimeters, about 0.5 square centimeters to about 70 square centimeters, about 0.5 square centimeters to about 60 square centimeters, about 0.5 square centimeters to about 50 square centimeters, about 0.5 square centimeters to about 40 square centimeters, about 0.5 square centimeters to about 30 square centimeters, about 0.5 square centimeters to about 20 square centimeters, about 0.5 square centimeters to about 10 square centimeters, about 0.5 square centimeters to about 5 square centimeters, about 0.5 square centimeters to about 4 square centimeters, about 0.5 square centimeters to about 3 square centimeters, about 0.5 square centimeters to about 2 square centimeters, about 0.5 square centimeters to about 1 square centimeters, about 0.5 square centimeters to about 0.9 square centimeters, about 0.5 square centimeters to about 0.8 square centimeters, about 0.5 square centimeters to about 0.7 square centimeters, about 0.5 square centimeters to about 0.6 square centimeters, about 1 square centimeters to about 1000 square centimeters, about 1 square centimeters to about 900 square centimeters, about 1 square centimeters to about 800 square centimeters, about 1 square centimeters to about 700 square centimeters, about 1 square centimeters to about 600 square centimeters, about 1 square centimeters to about 500 square centimeters, about 1 square centimeters to about 400 square centimeters, about 1 square centimeters to about 300 square centimeters, about 1 square centimeters to about 200 square centimeters, about 1 square centimeters to about 100 square centimeters, about 1 square centimeters to about 90 square centimeters, about 1 square centimeters to about 80 square centimeters, about 1 square centimeters to about 70 square centimeters, about 1 square centimeters to about 60 square centimeters, about 1 square centimeters to about 50 square centimeters, about 1 square centimeters to about 40 square centimeters, about 1 square centimeters to about 30 square centimeters, about 1 square centimeters to about 20 square centimeters, about 1 square centimeters to about 10 square centimeters, about 1 square centimeters to about 5 square centimeters, about 1 square centimeters to about 4 square centimeters, about 1 square centimeters to about 3 square centimeters, about 1 square centimeters to about 2 square centimeters, about 10 square centimeters to about 1000 square centimeters, about 10 square centimeters to about 900 square centimeters, about 10 square centimeters to about 800 square centimeters, about 10 square centimeters to about 700 square centimeters, about 10 square centimeters to about 600 square centimeters, about 10 square centimeters to about 500 square centimeters, about 10 square centimeters to about 400 square centimeters, about 10 square centimeters to about 300 square centimeters, about 10 square centimeters to about 200 square centimeters, about 10 square centimeters to about 100 square centimeters, about 10 square centimeters to about 90 square centimeters, about 10 square centimeters to about 80 square centimeters, about 10 square centimeters to about 70 square centimeters, about 10 square centimeters to about 60 square centimeters, about 10 square centimeters to about 50 square centimeters, about 10 square centimeters to about 40 square centimeters, about 10 square centimeters to about 30 square centimeters, about 10 square centimeters to about 20 square centimeters, about 50 square centimeters to about 1000 square centimeters, about 50 square centimeters to about 900 square centimeters, about 50 square centimeters to about 800 square centimeters, about 50 square centimeters to about 700 square centimeters, about 50 square centimeters to about 600 square centimeters, about 50 square centimeters to about 500 square centimeters, about 50 square centimeters to about 400 square centimeters, about 50 square centimeters to about 300 square centimeters, about 50 square centimeters to about 200 square centimeters, about 50 square centimeters to about 100 square centimeters, about 75 square centimeters to about 1000 square centimeters, about 75 square centimeters to about 900 square centimeters, about 75 square centimeters to about 800 square centimeters, about 75 square centimeters to about 700 square centimeters, about 75 square centimeters to about 600 square centimeters, about 75 square centimeters to about 500 square centimeters, about 75 square centimeters to about 400 square centimeters, about 75 square centimeters to about 300 square centimeters, about 75 square centimeters to about 200 square centimeters, about 75 square centimeters to about 100 square centimeters, about 100 square centimeters to about 1000 square centimeters, about 100 square centimeters to about 900 square centimeters, about 100 square centimeters to about 800 square centimeters, about 100 square centimeters to about 700 square centimeters, about 100 square centimeters to about 600 square centimeters, about 100 square centimeters to about 500 square centimeters, about 100 square centimeters to about 400 square centimeters, about 100 square centimeters to about 300 square centimeters, about 100 square centimeters to about 200 square centimeters, about 250 square centimeters to about 1000 square centimeters, about 250 square centimeters to about 900 square centimeters, about 250 square centimeters to about 800 square centimeters, about 250 square centimeters to about 700 square centimeters, about 250 square centimeters to about 600 square centimeters, about 250 square centimeters to about 500 square centimeters, about 250 square centimeters to about 400 square centimeters, about 250 square centimeters to about 300 square centimeters, about 500 square centimeters to about 1000 square centimeters, about 500 square centimeters to about 900 square centimeters, about 500 square centimeters to about 800 square centimeters, about 500 square centimeters to about 700 square centimeters, about 500 square centimeters to about 600 square centimeters, about 750 square centimeters to about 1000 square centimeters, about 750 square centimeters to about 900 square centimeters, about 750 square centimeters to about 800 square centimeters, or a range between any two of these values. Specific examples of the dissolvable microneedle patch range in size from about 1000 square centimeters, about 900 square centimeters, about 800 square centimeters, about 700 square centimeters, about 600 square centimeters, about 500 square centimeters, about 400 square centimeters, about 300 square centimeters, about 200 square centimeters, about 100 square centimeters, about 90 square centimeters, about 80 square centimeters, about 70 square centimeters, about 60 square centimeters, about 50 square centimeters, about 40 square centimeters, about 30 square centimeters, about 20 square centimeters, about 10 square centimeters, about 5 square centimeters, about 4 square centimeters, about 3 square centimeters, about 2 square centimeters, about 1 square centimeters, about 0.9 square centimeters, about 0.8 square centimeters, about 0.7 square centimeters, about 0.6 square centimeters, about 0.7 square centimeters, about 0.6 square centimeters, about 0.5 square centimeters, about 0.4 square centimeters, about 0.3 square centimeters, about 0.2 square centimeters, about 0.1 square centimeters, or a range between any two of these values.

In some embodiments, the method of treating a skin condition comprising applying a dissolvable microneedle patch, wherein the dissolvable microneedle patch comprises a backing layer and a microneedle layer. In some embodiments, the dissolvable microneedle patch comprises a backing layer and a microneedle layer wherein the microneedle layer is placed directly on top of the skin. In some embodiments, the dissolvable microneedle patch comprises a backing layer wherein the backing layer is composed of adhesive medical tape. In some embodiments, the dissolvable microneedle patch comprises a backing layer wherein the backing layer comprises a therapeutically active ingredient.

In some embodiments, the method of treating a skin condition comprising applying a dissolvable microneedle patch, wherein the dissolvable microneedle patch comprises a backing layer wherein the backing layer is a removable substrate. In some embodiments, the dissolvable microneedle patch wherein the removable substrate comprises an adhesive medical tape. In some embodiments, the backing layer comprises a quick dissolving polymer. In some embodiments, the dissolvable microneedle patch wherein the removable substrate comprises a therapeutically active ingredient dispersed in a polymer. In some embodiments, the dissolvable microneedle patch wherein the plurality of microneedles are attached to the removable substrate and comprise a tapered tip that extends away from the removal substrate. In some embodiments, the dissolvable microneedle patch wherein the removable substrate releases at least about 90% of the microneedles from the adhesive surface within a period of about 20 minutes after application to skin. In some embodiments, the dissolvable microneedle patch wherein the removable substrate releases at least about 90% of the microneedles from the adhesive surface within a period of about 5 minutes after application to skin. In some embodiments, the dissolvable microneedle patch wherein 90% of the microneedles are released from the adhesive surface within a period of about 0 minutes to about 20 minutes, about 0 minutes to about 15 minutes, about 0 minutes to about 10 minutes, about 0 minutes to about 9 minutes, about 0 minutes to about 8 minutes, about 0 minutes to about 7 minutes, about 0 minutes to about 6 minutes, about 0 minutes to about 5 minutes, about 0 minutes to about 4 minutes, about 0 minutes to about 3 minutes, about 0 minutes to about 2 minutes, about 0 minutes to about 1 minutes, about 1 minute to about 20 minutes, about 1 minute to about 15 minutes, about 1 minute to about 10 minutes, about 1 minute to about 9 minutes, about 1 minute to about 8 minutes, about 1 minute to about 7 minutes, about 1 minute to about 6 minutes, about 1 minute to about 5 minutes, about 1 minute to about 4 minutes, about 1 minute to about 3 minutes, about 1 minute to about 2 minutes, about 2 minutes to about 20 minutes, about 2 minutes to about 15 minutes, about 2 minutes to about 10 minutes, about 2 minutes to about 9 minutes, about 2 minutes to about 8 minutes, about 2 minutes to about 7 minutes, about 2 minutes to about 6 minutes, about 2 minutes to about 5 minutes, about 2 minutes to about 4 minutes, about 2 minutes to about 3 minutes, about 5 minutes to about 20 minutes, about 5 minutes to about 15 minutes, about 5 minutes to about 10 minutes, about 5 minutes to about 9 minutes, about 5 minutes to about 8 minutes, about 5 minutes to about 7 minutes, about 5 minutes to about 6 minutes, about 10 minutes to about 20 minutes, about 10 minutes to about 15 minutes, about 15 minutes to about 20 minutes, about 0 seconds to about 60 seconds, about 0 seconds to about 0 seconds to about 45 seconds, about 0 seconds to about 30 seconds, about 0 seconds to about 15 seconds, about 0 seconds to about 10 seconds, about 0 seconds to about 9 seconds, about 0 seconds to about 8 seconds, about 0 seconds to about 7 seconds, about 0 seconds to about 6 seconds, about 0 seconds to about 5 seconds, about 0 seconds to about 4 seconds, about 0 seconds to about 3 seconds, about 0 seconds to about 2 seconds, about 0 seconds to about 1 seconds, about 1 second to about 60 seconds, about 1 second to about 45 seconds, about 1 second to about 30 seconds, about 1 second to about 15 seconds, about 1 second to about 10 seconds, about 1 second to about 9 seconds, about 1 second to about 8 seconds, about 1 second to about 7 seconds, about 1 second to about 6 seconds, about 1 second to about 5 seconds, about 1 second to about 4 seconds, about 1 second to about 3 seconds, about 1 second to about 2 seconds, about 2 seconds to about 60 seconds, about 2 seconds to about 45 seconds, about 2 seconds to about 30 seconds, about 2 seconds to about 15 seconds, about 2 seconds to about 10 seconds, about 2 seconds to about 9 seconds, about 2 seconds to about 8 seconds, about 2 seconds to about 7 seconds, about 2 seconds to about 6 seconds, about 2 seconds to about 5 seconds, about 2 seconds to about 4 seconds, about 2 seconds to about 3 seconds, about 5 seconds to about 60 seconds, about 5 seconds to about 45 seconds, about 5 seconds to about 30 seconds, about 5 seconds to about 15 seconds, about 5 seconds to about 10 seconds, about 5 seconds to about 9 seconds, about 5 seconds to about 8 seconds, about 5 seconds to about 7 seconds, about 5 seconds to about 6 seconds, about 10 seconds to about 60 seconds, about 10 seconds to about 45 seconds, about 10 seconds to about 30 seconds, about 10 seconds to about 15 seconds, about 15 seconds to about 60 seconds, about 15 seconds to about 45 seconds, about 15 seconds to about 30 seconds, about 30 seconds to about 60 seconds, about 30 seconds to about 45 seconds, about 45 seconds to about 60 seconds, or a value within these ranges. In specific examples, 90% of the microneedles are released from the adhesive surface of the dissolvable microneedle patch within about 20 minutes, about 15 minutes, about 10 minutes, about 9 minutes, about 8 minutes, about 7 minutes, about 6 minutes, about 5 minutes, about 4 minutes, about 3 minutes, about 2 minutes, about 1 minute, about 60 seconds, about 45 seconds, about 30 seconds, about 15 seconds, about 10 seconds, about 9 seconds, about 8 seconds, about 7 seconds, about 6 seconds, about 5 seconds, about 4 seconds, about 3 seconds, about 2 seconds, about 1 second or a range between any two of these values.

In some embodiments, the method of treating a skin condition comprising applying a dissolvable microneedle patch comprising a backing layer, wherein the backing layer overlays the base of the tip portion in such a manner that each microneedle is separated from the other microneedles on the patch and forms a discrete entity when the substrate is removed upon application of the patch on the skin.

In some embodiments, the method of treating a skin condition comprising applying a dissolvable microneedle patch, wherein the dissolvable microneedle patch is (i) placed on a surface area of the skin of a patient in need of treatment, or pre-treatment testing to assess for hypersensitivity reaction, general tolerability, or other adverse events, (ii) exerting sufficient force on the patch composition to permit the microneedles to penetrate through the epidermis into the papillary dermis, and (iii) allowing the plurality of microneedles to remain in the skin until the biodegradable polymer degrades (iv) removing the adhesive substrate from the patch composition, wherein the step (ii) is carried out by applying pressure with a finger, wherein the pressure is sufficient for a force ranging from about 0N to about 1,000N. In the preferred embodiment of the present application, the pressure applied is about 10N. In an alternate embodiment of the present application the step (ii) is carried out by impact insertion using an applicator device, wherein the pressure is sufficient for a force ranging from about 0 to about 1,000N. In the preferred embodiment of the present application, the pressure applied is about 10N. In some embodiments, the force applied by a finger or an applicator device ranges from about 0N to about 1,000 N, about 0N to about 900N, about 0N to about 800N, about 0N to about 700N, about 0N to about 600N, about 0N to about 500N, about 0N to about 400N, about 0N to about 300N, about 0N to about 200N, about 0N to about 100N, about 0N to about 90N, about 0N to about 80N, about 0N to about 70N, about 0N to about 60N, about 0N to about 50N, about 0N to about 40N, about 0N to about 30N, about 0N to about 20N, about 0N to about 10N, about 0N to about 9N, about 0N to about 8N, about 0N to about 7N, about 0N to about 6N, about 0N to about 5N, about 0N to about 4N, about 0N to about 3N, about 0N to about 2N, about 0 N to about 1N, about 0N to about 0.9N, about 0N to about 0.8N, about 0N to about 0.7N, about 0N to about 0.6N, about 0N to about 0.5N, about 0N to about 0.4N, about 0N to about 0.3N, about 0N to about 0.2N, about 0N to about 0.1N, about 0.1N to about 1000N, about 0.1N to about 900N, about 0.1 N to about 800N, about 0.1N to about 700N, about 0.1N to about 600N, about 0.1N to about 500N, about 0.1N to about 400N, about 0.1N to about 300N, about 0.1N to about 200N, about 0.1N to about 100N, about 0.1N to about 90N, about 0.1N to about 80N, about 0.1N to about 70N, about 0.1N to about 60N, about 0.1N to about 50N, about 0.1N to about 40N, about 0.1N to about 30N, about 0.1N to about 20N, about 0.1N to about 10N, about 9N, about 0.1N to about 8N, about 0.1N to about 7N, about 0.1N to about 6N, about 0.1N to about 5N, about 0.1N to about 4N, about 0.1N to about 3N, about 0.1N to about 2N, about 0.1N to about 1N, about 0.1N to about 0.9N, about 0.1N to about 0.8N, about 0.1N to about 0.7N, about 0.1N to about 0.6N, about 0.1N to about 0.5N, about 0.1N to about 0.4N, about 0.1N to about 0.3N, about 0.1N to about 0.2N, about 1N to about 1000N, about 1N to about 900N, about 1N to about 800 N, about 1N to about 700N, about 1N to about 600N, about 1N to about 500N, about 1N to about 400N, about 1N to about 300N, about 1N to about 200N, about 1N to about 100N, about 1N to about 90N, about 1N to about 80N, about 1N to about 70N, about 1N to about 60N, about 1N to about 50N, about 1N to about 40N, about 1N to about 30N, about 1N to about 20N, about 1N to about 10N, about 1N to about 9N, about 1N to about 8N, about 1N to about 7N, about 1N to about 6N, about 1N to about 5N, about 1N to about 4N, about 1N to about 3N, about 1N to about 2N, about 10N to about 1000N, about 10N to about 900 N, about 10N to about 800N, about 10N to about 700N, about 10N to about 600N, about 10N to about 500N, about 10N to about 400N, about 10N to about 300N, about 10N to about 200N, about 10N to about 100N, about 10N to about 90N, about 10N to about 80N, about 10N to about 70N, about 10N to about 60N, about 10N to about 50N, about 10N to about 40N, about 10N to about 30N, about 10N to about 20N, about 50N to about 1000N, about 50N to about 900N, about 50N to about 800N, about 50N to about 700N, about 50N to about 600N, about 50N to about 500N, about 50N to about 400N, about 50N to about 300N, about 50N to about 200N, about 50N to about 100N, about 100N to about 1000N, about 100N to about 900N, about 100N to about 800N, about 100N to about 700N, about 100N to about 600N, about 100N to about 500N, about 100N to about 400N, about 100N to about 300N, about 100N to about 200N, about 200N to about 1000N, about 200N to about 900N, about 200N to about 800N, about 200N to about 700N, about 200N to about 600N, about 200N to about 500N, about 200N to about 400N, about 200N to about 300N, about 500N to about 1000N, about 500N to about 900N, about 500N to about 800N, about 500N to about 700N, about 500N to about 600N, or a value within these ranges. In specific examples, the force applied by a finger or an applicator device is about 0N, about 0.1N, about 0.2N, about 0.3N, about 0.4N, about 0.5N, about 0.6N, about 0.7N, about 0.8N, about 0.9N, about 1N, about 2N, about 3N, about 4N, about 5N, about 6N, about 7N, about 8N, about 9N, about 10N, about 15N, about 20N, about 30N, about 40N, about 50N, about 60N, about 70N, about 80N, about 90N, about 100N, about 200N, about 300N, about 400N, about 500N, about 600N, about 700N, about 800N, about 900N, or a range between and two of these values.

In some embodiments, the method of treating a skin condition comprising applying a dissolvable microneedle patch wherein the dissolvable microneedle patch is (i) placed on a surface area of the skin of a patient in need of treatment, or pre-treatment testing to assess for hypersensitivity reaction, general tolerability, or other adverse events, (ii) exerting sufficient force on the patch composition to permit the microneedles to penetrate through the epidermis into the papillary dermis, wherein the sufficient force is applied by impact insertion using an applicator device. In some embodiments, the sufficient force applied by impact insertion ranges from 0N to about 1000N. In some embodiments, the sufficient force applied by impact insertion is 10N.

In some embodiments, the method of treating a skin condition comprising applying a dissolvable microneedle patch comprising both immediate and sustained release polymers, wherein the skin condition comprises a viral condition or a neoplastic condition.

In some embodiments, the method of treating a skin condition comprising applying a dissolvable microneedle patch comprising immediate release polymer, wherein the skin condition comprises alopecia areata or vitiligo. In some embodiments, the method of applying a dissolvable microneedle patch comprising immediate release polymer, wherein the method comprises the medical procedure for testing allergies or hypersensitivity to the therapeutically active agent.

Embodiments of the application are directed to the method of testing a patient in need thereof for allergies comprising applying a dissolvable microneedle patch for delivery of a therapeutically active ingredient to the skin; exerting sufficient force on the dissolvable microneedle patch to permit the microneedles to penetrate to a location selected from the group consisting of the epidermis, the dermis and the papillary dermis; removing adhesive substrate from the patch composition; and allowing the plurality of microneedles to remain in the skin until the biodegradable polymer degrades.

In some embodiments, the method of testing a patient in need thereof for hypersensitivity comprising applying a dissolvable microneedle patch for delivery of a therapeutically active ingredient to the skin; exerting sufficient force on the dissolvable microneedle patch to permit the microneedles to penetrate to a location selected from the group consisting of the epidermis, the dermis and the papillary dermis; removing adhesive substrate from the patch composition; and allowing the plurality of microneedles to remain in the skin until the biodegradable polymer degrades.

In some embodiments, the method of sensitizing a patient to the immune stimulating active ingredient in need thereof comprising applying a dissolvable microneedle patch for delivery of a therapeutically active ingredient to the skin; exerting sufficient force on the dissolvable microneedle patch to permit the microneedles to penetrate to a location selected from the group consisting of the epidermis, the dermis and the papillary dermis; removing adhesive substrate from the patch composition; and allowing the plurality of microneedles to remain in the skin until the biodegradable polymer degrades.

Method of Manufacturing a Dissolvable Microneedle Patch

Embodiments of the application are directed to a method of manufacturing a dissolvable microneedle patch for delivery of a therapeutically active ingredient to the skin comprising, dispersing a lyophilized therapeutically active ingredient into a first biodegradable polymer, dispensing the first biodegradable polymer into a mold to form a plurality of microneedles with a tip portion, body portion, and base portion, dispensing a second biodegradable polymer on top of the first biodegradable polymer to form a backing layer, applying an adhesive substrate to the second biodegradable polymer; wherein the plurality of microneedles comprise microneedles of at least two different lengths; and wherein the therapeutically active ingredient is selected from the group consisting of a vaccine, and immune stimulating molecule, an immune stimulating organism, and an immune-stimulating protein.

In some embodiments, the method of manufacturing a dissolvable microneedle patch wherein the dissolvable microneedle patch comprises a plurality of microneedles comprising microneedles of at least two different lengths are selected from the group consisting of a length to terminate in the epidermis and a length to terminate in the reticular or papillary dermis. In some embodiments, the dissolvable microneedle patch comprises a plurality of microneedles with one to five different lengths. In some embodiments, the dissolvable microneedle patch comprises a plurality of microneedles wherein the at least two varying lengths may be different based on the location on the body, patient age, or the skin condition to be treated. In some embodiments, the needles of at least two different lengths are of equal proportion. In some embodiments, the needles of at least two different lengths can be of different proportions. In an alternate embodiment, the dissolvable microneedle patch comprises a plurality of microneedles wherein the microneedles are of a single length. In some embodiments, the dissolvable microneedle patch comprises a plurality of microneedles wherein the microneedles are of equal lengths. In some embodiments, the dissolvable microneedle patch comprises a plurality of microneedles wherein the length of the microneedles range from about 10 microns to about 1000 microns, about 10 microns to about 900 microns, about 10 microns to about 800 microns, about 10 microns to about 700 microns, about 10 microns to about 600 microns, about 10 microns to about 500 microns, about 10 microns to about 400 microns, about 10 microns to about 300 microns, about 10 microns to about 200 microns, about 10 microns to about 100 microns, about 10 microns to about 90 microns, about 10 microns to about 80 microns, about 10 microns to about 70 microns, about 10 microns to about 60 microns, about 10 microns to about 50 microns, about 10 microns to about 40 microns, about 10 microns to about 30 microns, about 10 microns to about 20 microns, about 10 microns to about 15 microns, about 20 microns to about 1000 microns, about 20 microns to about 900 microns, about 20 microns to about 800 microns, about 20 microns to about 700 microns, about 20 microns to about 600 microns, about 20 microns to about 500 microns, about 20 microns to about 400 microns, about 20 microns to about 300 microns, about 20 microns to about 200 microns, about 20 microns to about 100 microns, about 20 microns to about 90 microns, about 20 microns to about 80 microns, about 20 microns to about 70 microns, about 20 microns to about 60 microns, about 20 microns to about 50 microns, about 20 microns to about 40 microns, about 20 microns to about 30 microns, about 20 microns to about 25 microns, about 50 microns to about 1000 microns, about 50 microns to about 900 microns, about 50 microns to about 800 microns, about 50 microns to about 700 microns, about 50 microns to about 600 microns, about 50 microns to about 500 microns, about 50 microns to about 400 microns, about 50 microns to about 300 microns, about 50 microns to about 200 microns, about 50 microns to about 100 microns, about 100 microns to about 1000 microns, about 100 microns to about 900 microns, about 100 microns to about 800 microns, about 100 microns to about 700 microns, about 100 microns to about 600 microns, about 100 microns to about 500 microns, about 100 microns to about 400 microns, about 100 microns to about 300 microns, about 100 microns to about 200 microns, about 200 microns to about 1000 microns, about 200 microns to about 900 microns, about 200 microns to about 800 microns, about 200 microns to about 700 microns, about 200 microns to about 600 microns, about 200 microns to about 500 microns, about 200 microns to about 400 microns, about 200 microns to about 300 microns, about 500 microns to about 1000 microns, about 500 microns to about 900 microns, about 500 microns to about 800 microns, about 500 microns to about 700 microns, about 500 microns to about 600 microns, about 800 microns to about 1000 microns, about 800 microns to about 900 microns, about 900 microns to about 1000 microns, or a value within these ranges.

In some embodiments, the method of manufacturing a dissolvable microneedle patch wherein the microneedles are tapered to a point to facilitate the insertion of the microneedles into the skin. In some embodiments, the dissolvable microneedle patch comprises a plurality of microneedles wherein the microneedles have a tapered tip portion containing a therapeutically active ingredient dispersed in a matrix or suspension of a biodegradable polymer.

In some embodiments, the method of manufacturing a dissolvable microneedle patch wherein the dissolvable microneedle patch comprises a plurality of microneedles comprising microneedles of at least two different lengths are composed of equal volumes of biodegradable polymer. In some embodiments, the dissolvable microneedle patch comprises a plurality of microneedles wherein the volume of each microneedle may remain constant which is achieved by changing the diameter of each of the microneedles as required. In some embodiments, the dissolvable microneedle patch comprises a plurality of microneedles wherein the volume of each microneedle is unequal. In some embodiments, the dissolvable microneedle patch comprises a plurality of microneedles wherein the volume will depend on the concentration of the specific immune stimulants used.

In some embodiments, the method of manufacturing a dissolvable microneedle patch wherein the dissolvable microneedle patch comprises a plurality of microneedles wherein the tip portion constitutes 5-99% of the total volume of the microneedle. In some embodiments, the microneedle tip portion constitutes about 20% to about 90% of the total volume of the microneedle. In some embodiments, the microneedle tip portion constitutes about 50% of the total volume of the microneedle. In some embodiments, the microneedle tip portion constitutes about 75% of the total volume of the microneedle. In some embodiments, the microneedle tip portion constitutes about 5% to about 99%, about 5% to about 95%, about 5% to about 90%, about 5% to about 85%, about 5% to about 80%, about 5% to about 75%, about 5% to about 70%, about 5% to about 60%, about 5% to about 50%, about 5% to about 40%, about 5% to about 30%, about 5% to about 20%, about 5% to about 15%, about 5% to about 10%, about 10% to about 99%, about 10% to about 95%, about 10% to about 90%, about 10% to about 85%, about 10% to about 80%, about 10% to about 75%, about 10% to about 70%, about 10% to about 60%, about 10% to about 50%, about 10% to about 40%, about 10% to about 30%, about 10% to about 20%, about 10% to about 15%, about 15% to about 99%, about 15% to about 95%, about 15% to about 90%, about 15% to about 85%, about 15% to about 80%, about 15% to about 75%, about 15% to about 70%, about 15% to about 60%, about 15% to about 50%, about 15% to about 40%, about 15% to about 30%, about 15% to about 20%, about 25% to about 99%, about 25% to about 95%, about 25% to about 90%, about 25% to about 85%, about 25% to about 80%, about 25% to about 75%, about 25% to about 70%, about 25% to about 60%, about 25% to about 50%, about 25% to about 40%, about 25% to about 30%, about 50% to about 99%, about 50% to about 95%, about 50% to about 90%, about 50% to about 85%, about 50% to about 80%, about 50% to about 75%, about 50% to about 70%, about 50% to about 60%, about 60% to about 99%, about 60% to about 95%, about 60% to about 90%, about 60% to about 85%, about 60% to about 80%, about 60% to about 75%, about 60% to about 70%, about 70% to about 99%, about 70% to about 95%, about 70% to about 90%, about 70% to about 85%, about 70% to about 80%, about 70% to about 75%, about 80% to about 99%, about 80% to about 95%, about 80% to about 90%, about 80% to about 85%, about 90% to about 99%, about 90% to about 95%, or a value within these ranges. Specific examples may include about 99%, about 95%, about 90%, about 85%, about 80%, about 75%, about 70%, about 65%, about 60%, about 55%, about 50%, about 45%, about 40%, about 35%, about 30%, about 25%, about 20% about 15%, about 10%, about 9%, about 8%, about 7%, about 6%, about 5%, or a range between any two of these values. In some embodiments, the plurality of microneedles comprise a therapeutically active ingredient. In some embodiments, the plurality of microneedles each comprise about the same amount of the therapeutically active ingredient. In some embodiments, the plurality of microneedles each comprise different amounts of the therapeutically active ingredient.

In some embodiments, the method of manufacturing a dissolvable microneedle patch to treat a skin condition wherein the skin condition is a wart, condyloma acuminatum, Bowenoid papulosis, molluscum contagiosum, actinic keratosis, squamous cell carcinoma, basal cell carcinoma, verrucous carcinoma, epidermodysplasia verruciformis, vitiligo, and alopecia areata.

In some embodiments, the method of manufacturing a dissolvable microneedle patch wherein certain compounds disclosed herein may possess useful immune stimulating activity and may be used in the treatment or prophylaxis of a disease or condition in which the immune system can play an active role. In some embodiments, successful delivery of immune stimulant results in classic clinical signs of inflammation such as, rubor, tumor, and calor (redness, swelling and warmth, respectively). Thus, embodiments are also directed to pharmaceutical compositions comprising one or more compounds disclosed herein together with a pharmaceutically acceptable carrier, as well as methods of making and using the compounds and compositions. Certain embodiments are directed to methods for stimulating the immune system. Other embodiments are directed to methods for treating a skin condition in a patient in need of such treatment, comprising administering to said patient a therapeutically effective amount of a compound or composition according to the present invention. Also provided is the use of certain compounds disclosed herein in the manufacture of a medicament for the treatment of a disease or condition ameliorated by the activation of the immune system.

In some embodiments, the method of manufacturing a dissolvable microneedle patch for delivery of a therapeutically active ingredient to the skin. In some embodiments, the therapeutically active ingredient is in a therapeutically effective amount. In some embodiments, the therapeutically effective amount is an amount disclosed herein. In some embodiments, administration of the dissolvable microneedle patch leads to a disappearance of the conditions being treated. In some embodiments, administration of the dissolvable microneedle patch leads to disappearance of the skin lesion or skin lesions in direct contact with the dissolvable microneedle patch. In some embodiments, administration of the dissolvable microneedle patch leads to the disappearance of the skin lesion or skin lesions adjacent to the dissolvable microneedle patch. In some embodiments, the dissolvable microneedle patch delivers the therapeutically active ingredient to stimulate a local immune response.

In some embodiments, the method of manufacturing a dissolvable microneedle patch for delivery of a therapeutically active ingredient, wherein the therapeutically active ingredient is selected from the group consisting of a vaccine, an immune stimulating molecule, immune stimulating organism, and an immune stimulating protein.

In some embodiments, the therapeutically active ingredient is a vaccine, wherein the vaccine is selected from the group consisting of measles-mumps-rubella vaccine, mumps vaccine, *Bacillus* Calmette-Guérin vaccine, human papillomavirus vaccine, *Mycobacterium w* vaccine. In some embodiments, the therapeutically active ingredient is an immune stimulating molecule, wherein the immune stimulating molecule is imiquimod. In some embodiments, the therapeutically active ingredient is an immune stimulating organism, wherein the immune stimulating organism is *Corynebacterium parvus, Cutibacterium acnes, Propionibacterium*, and/or *Mycobacterium*. In some embodiments, the therapeutically active ingredient is an immune stimulating protein, wherein the immune stimulating protein is selected from the group consisting of *Candida* antigen, *Trichophyton* antigen, tuberculin, purified protein derivative (also), human papillomavirus surface proteins, interferon alpha, interferon beta, and interferon gamma.

In some embodiments, the method of manufacturing a dissolvable microneedle patch for delivery of a therapeutically active ingredient, wherein the therapeutically active ingredient is *Candida* antigen. In some embodiments, the therapeutically active ingredient is *Candida* antigen. In some embodiments, the *Candida* antigen is substantially free of glycerin. In some embodiments, the *Candida* antigen is glycerin free. In some embodiments, the glycerin free *Candida* antigen is lyophilized.

Some embodiments are directed to methods of manufacturing a dissolvable microneedle patch comprising an immune stimulating compound comprising adding an immune stimulating compound to a biodegradable polymer; pouring the composition comprising the biodegradable polymer and the immune stimulating compound into a microneedle mold; removing the microneedle mold after the composition comprising the biodegradable polymer and the immune stimulating compound solidify. In some embodiments, the immune stimulating compound contains glycerin. In some embodiments, the method of manufacturing a dissolvable microneedle patch comprising an immune stimulating compound further comprises a step of removing glycerin from the immune stimulating compound. In some embodiments, the method of manufacturing a dissolvable microneedle patch comprising an immune stimulating compound further comprises a step of removing glycerin from the immune stimulating compound, wherein the glycerin is removed by dialysis. In some embodiments, the glycerin is removed prior to adding the immune stimulating compound to a biodegradable polymer.

In some embodiments, the method of manufacturing a dissolvable microneedle patch for delivery of a therapeutically active ingredient, wherein the therapeutically active ingredient is dispersed throughout the polymer. In some embodiments, the plurality of microneedles comprise a therapeutically active ingredient wherein the therapeutically active ingredient is evenly distributed throughout the microneedle. In some embodiments, the plurality of microneedles comprise a therapeutically active ingredient wherein the therapeutically active ingredient is concentrated at the tip of the microneedle. In some embodiments, the plurality of microneedles comprise a microneedle with essentially no therapeutically active ingredient in the half of the microneedle closest to the base. In some embodiments, the plurality of microneedles comprise a microneedle with no therapeutically active ingredient in the half of the microneedle closest to the base. In some embodiments, the therapeutically active ingredient is a solid powder. In some embodiments, the therapeutically active ingredient is a solid powder dispersed throughout the polymer. In some embodiments, the therapeutically active ingredient is lyophilized. In some embodiments, the therapeutically active ingredient is lyophilized and dispersed throughout the polymer.

Some embodiments disclosed herein also include pharmaceutical compositions which contain, as the active ingredient, one or more of the compounds disclosed herein in combination with one or more pharmaceutically acceptable carriers (excipients).

The active compound can be effective over a wide dosage range and can be generally administered in a therapeutically effective amount. It will be understood, however, that the amount of the compound actually administered will usually be determined by a physician, according to the relevant circumstances, including the condition to be treated, the actual compound administered, the age, weight, and response of the individual patient, the severity of the patient's symptoms, and the like. In some embodiments, the plurality of microneedles will contain equal amounts of therapeutically active ingredient. In some embodiments, the plurality of microneedles will contain unequal amounts of therapeutically active ingredient.

In some embodiments, the method of manufacturing a dissolvable microneedle patch for delivery of a therapeutically active ingredient, wherein the amount of therapeutically active ingredient administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. In some embodiments, that condition is selected from a wart, condyloma acuminatum, Bowenoid papulosis, molluscum contagiosum, actinic keratosis, squamous cell carcinoma, basal cell carcinoma, verrucous carcinoma, epidermodysplasia verruciformis and successful treatment of these conditions results in a one point improvement on any ordinal or interval assessment scale, such as the Physician Global Assessment or the Investigator Global Assessment. In some embodiments, the condition is selected from a wart, condyloma acuminatum, Bowenoid papulosis, molluscum contagiosum, actinic keratosis, squamous cell carcinoma, basal cell carcinoma, verrucous carcinoma, epidermodysplasia verruciformis and successful treatment of these conditions results in about 100% loss of skin lesions by clinical, histopathological, or dermatoscopic assessment as well as assessment by optical coherence tomography or confocal microscopy in the location of the patch is administered. In some embodiments, the condition is selected from a wart, condyloma acuminatum, Bowenoid papulosis, molluscum contagiosum, actinic keratosis, squamous cell carcinoma, basal cell carcinoma, verrucous carcinoma, epidermodysplasia verruciformis and successful treatment of these conditions results in about 50% loss of skin lesions by clinical, histopathological, or dermatoscopic assessment as well as assessment by optical coherence tomography or confocal microscopy in the location of the patch is administered. In some embodiments, successful treatment of a wart, condyloma acuminatum, Bowenoid papulosis, molluscum contagiosum, actinic keratosis, squamous cell carcinoma, basal cell carcinoma, verrucous carcinoma, epidermodysplasia verruciformis with the dissolvable microneedle patch results in reduction of skin lesions in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include reducing skin lesions, by clinical, histopathological, or dermatoscopic assessment as well as assessment by optical coherence tomography or confocal microscopy by about 100%, about 99%, about 95%, about 90%, about 85%, about 80%, about 75%, about 70%, about 65%, about 60%, about 55%, about 50% or a range between any two of these values.

In some embodiments, the method of manufacturing a dissolvable microneedle patch for delivery of a therapeutically active ingredient to treat a skin condition, wherein the successful treatment of a wart, condyloma acuminatum, Bowenoid papulosis, molluscum contagiosum, actinic keratosis, squamous cell carcinoma, basal cell carcinoma, verrucous carcinoma, epidermodysplasia verruciformis with the dissolvable microneedle patch results in reduction of in the width, length, or height of skin lesions in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include reducing the width, length, or height of skin lesions measured by clinical, histopathological, or dermatoscopic assessment as well as assessment by optical coherence tomography or confocal microscopy by about 100%, about 99%, about 95%, about 90%, about 85%, about 80%, about 75%, about 70%, about 65%, about 60%, about 55%, about 50% or a range between any two of these values.

In some embodiments, the method of manufacturing a dissolvable microneedle patch for delivery of a therapeutically active ingredient to treat the skin condition alopecia areata with a dissolvable microneedle patch, wherein successful treatment of this condition results in a one point improvement on any ordinal or interval assessment scale, such as the Physician Global Assessment or the Investigator Global Assessment. In some embodiments, the condition is alopecia areata and successful treatment of this condition results in about 100% restoration of hair growth in the location of the patch is administered. In some embodiments, the condition is alopecia areata and successful treatment of this condition results in at least about 50% increase in hair growth as defined by number of hair follicles with actively growing hair shafts as seen with clinical, trichoscopic, or histopathological assessment in the location of the patch is administered. In some embodiments, successful treatment of alopecia areata with the dissolvable microneedle patch results in an increase in hair growth in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include increasing hair growth as defined by the number of hair follicles with actively growing hair shafts as seen with clinical, trichoscopic, or histopathologic assessment, by about 100%, about 99%, about 95%, about 90%, about 85%, about 80%, about 75%, about 70%, about 65%, about 60%, about 55%, about 50% or a range between any two of these values.

In some embodiments, the method of manufacturing a dissolvable microneedle patch for delivery of a therapeutically active ingredient to treat the skin condition alopecia areata with a dissolvable microneedle patch, wherein successful treatment results in improvement in the Severity Alopecia Tool (SALT) score in the location the patch is administered by a range from about 50% to about 100%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 100%, about 60% to about 95%, about 60% to about 90%, about 60% to about 85%, about 60% to about 80%, about 60% to about 75%, about 60% to about 70%, about 60% to about 65%, about 70% to about 100%, about 70% to about 95%, about 70% to about 90%, about 70% to about 85%, about 70% to about 80%, about 70% to about 75%, about 80% to about 100%, about 80% to about 95%, about 80% to about 90%, about 80% to about 85%, about 90% to about 100%, about 90% to about 95%, or a value within these ranges. Specific examples may include improving the Severity Alopecia Tool (SALT) score by about 100%, about 99%, about 95%, about 90%, about 85%, about 80%, about 75%, about 70%, about 65%, about 60%, about 55%, about 50% or a range between any two of these values.

In some embodiments, the method of manufacturing a dissolvable microneedle patch, wherein each dissolvable microneedle patch contains a standardized amount of therapeutically active ingredient.

In some embodiments, the method of manufacturing a dissolvable microneedle patch, wherein the dissolvable microneedles may comprise about 1% to about 90% of one or more therapeutically active ingredients disclosed herein. In some embodiments, the dissolvable microneedles may comprise about 50% to about 75% of one or more therapeutically active ingredients disclosed herein. In some embodiments, the dissolvable microneedles may comprise about 25% to about 50% of one or more therapeutically active ingredients disclosed herein. In some embodiments, the dissolvable microneedles may comprise about 25% to about 75% of one or more therapeutically active ingredients disclosed herein. In some embodiments, the dissolvable microneedles may comprise about 40% to about 60% of one or more therapeutically active ingredients disclosed herein. In some embodiments, the dissolvable microneedles may comprise about 60% to about 80% of one or more therapeutically active ingredients disclosed herein. In some embodiments, the one or more therapeutically active ingredients are in an amount of about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45% about 15% to about 40%, about 15% to about 35%, about 15% to about 30%, about 15% to about 25%, about 15% to about 20%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 35% to about 90%, about 35% to about 85%, about 35% to about 80%, about 35% to about 75%, about 35% to about 70%, about 35% to about 65%, about 35% to about 60%, about 35% to about 60%, about 35% to about 55%, about 35% to about 50%, about 35% to about 45%, about 35% to about 40%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 45% to about 90%, about 45% to about 85%, about 45% to about 80%, about 45% to about 75%, about 45% to about 70%, about 45% to about 65%, about 45% to about 60%, about 45% to about 55%, about 45% to about 50%, about 50% to about 90%, about 50% to about 85%, about 50% to about 80%, about 50% to about 75%, about 50% to about 70%, about 50% to about 65%, about 50% to about 60%, about 50% to about 55%, about 55% to about 90%, about 55% to about 85%, about 55% to about 80%, about 55% to about 75%, about 55% to about 70%, about 55% to about 65%, about 55% to about 60%, about 60% to about 90%, about 60% to about 85%, about 60% to about 80%, about 60% to about 75%, about 60% to about 70%, about 60% to about 65%, about 65% to about 90%, about 65% to about 85%, about 65% to about 80%, about 65% to about 75%, about 65% to about 70%, about 70% to about 90%, about 70% to about 85%, about 70% to about 80%, about 70% to about 75%, about 75% to about 90%, about 75% to about 85%, about 75% to about 80%, about 80% to about 90%, about 80% to about 85%, about 85% to about 90%, or a value within one of these ranges. Specific examples may include about 90%, about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 9%, about 8%, about 7%, about 6%, about 5%, about 4% about 3%, about 2%, about 1%. The foregoing all representing weight percentages of the pharmaceutical composition. In some embodiments, the pharmaceutical composition is suitable for transdermal administration.

In some embodiments, the method of manufacturing a dissolvable microneedle patch for delivery of a therapeutically active ingredient, wherein the therapeutically active ingredient is in a therapeutically effective amount. In some embodiments, the therapeutically effective amount may be about 1 microgram to 999 micrograms, 1 microgram to 100 micrograms, 100 micrograms to 200 micrograms, 200 micrograms to 300 micrograms, 300 micrograms to 400 micrograms, 400 micrograms to 500 micrograms, 500 micrograms to 600 micrograms, 600 micrograms to 700 micrograms, 700 micrograms to 800 micrograms, 800 micrograms to 900 micrograms, 900 micrograms to 999 micrograms, 1 mg to about 1000 mg, about 1 mg to about 900 mg, about 1 mg to about 800 mg, about 1 mg to about 700 mg, about 1 mg to about 600 mg, about 1 mg to about 500 mg, about 1 mg to about 400 mg, about 1 mg to about 300 mg, about 1 mg to about 200 mg, about 1 mg to about 100 mg, about 10 mg to about 1000 mg, about 50 mg to about 1000 mg, about 100 mg to about 1000 mg, about 200 mg to about 1000 mg, about 300 mg to about 1000 mg, about 400 mg to about 1000 mg, about 500 mg to about 1000 mg, about 10 mg to about 500 mg, about 50 mg to about 500 mg, about 100 mg to about 500 mg, about 10 mg to about 300 mg, about 50 mg to about 300 mg, from about 100 mg to about 300 mg, about 10 mg to about 150 mg, about 50 mg to about 150 mg, about 60 mg to about 120 mg, about 50 mg to about 120 mg or a range between any two of these values. Specific examples include, for example, about 1000 mg, about 900 mg, about 800 mg, about 700 mg, about 750 mg, about 600 mg, about 500 mg, about 400 mg, about 450 mg, about 300 mg, about 250 mg, about 200 mg, about 175 mg, about 150 mg, about 125 mg, about 120 mg, about 110 mg, about 100 mg, about 90 mg, about 80 mg, about 70 mg, about 60 mg, about 50 mg, about 30 mg, about 20 mg, or any value between the ranges disclosed above.

In some embodiments, the method of manufacturing a dissolvable microneedle patch comprising a therapeutically effective amount of active ingredient, wherein the therapeutically effective amount can vary according to, for example, the particular use for which the treatment is made, the location of administration of the microneedle patch, the health and condition of the patient, and the judgment of the prescribing physician. The proportion or concentration of a compound in a dissolvable microneedle can vary depending upon a number of factors including dosage, chemical characteristics (e.g., hydrophobicity), and the type of microneedle polymer. The dosage is likely to depend on such variables as the type and extent of progression of the disease or disorder, the overall health status of the particular patient, the relative biological efficacy of the compound selected, composition of the excipient, and its location of administration. Effective doses can be extrapolated from dose-response curves derived from in vitro or animal model test systems.

In some embodiments, the method of manufacturing a dissolvable microneedle patch comprising a plurality of needles, wherein the plurality of microneedles comprise a biodegradable polymer. In some embodiments, the dissolvable microneedle patch comprises a plurality of microneedles, wherein the microneedles comprise poly(lactic-co-glycolic acid). In some embodiments, the dissolvable microneedle patch comprises a plurality of microneedles, wherein the microneedles comprise a polymer selected from PLGA (poly(lactic-co-glycolic acid)), polyglycolic acid, fibroin, PLA (polylactic acid), PVP (polyvinylpyrrolidone), or PCL (polycaprolactone). In some embodiments, the dissolvable microneedle patch comprises a plurality of microneedles, wherein the microneedles comprise a single biodegradable polymer. In some embodiments, the dissolvable microneedle patch comprises a plurality of microneedles, wherein the microneedles comprise two biodegradable polymers. In some embodiments, the dissolvable microneedle patch comprises a plurality of microneedles, wherein the microneedles comprise a plurality of biodegradable polymers.

In some embodiments, the method of manufacturing a dissolvable microneedle patch comprising a biodegradable polymer, wherein the biodegradable polymer is capable of providing immediate release of a therapeutically active ingredient after insertion of the microneedle patch into the skin. In further embodiments, the immediate release biodegradable polymer is water soluble and comprises carboxy methylcellulose, chondroitin sulfate, dextran, dextrin, polyvinylpyrrolidone, maltose, trehalose, sucrose, galactose, amylopectin, polyvinyl alcohol, and/or polyvinylpyrrolidone-methacrylic acid. In further embodiments, the immediate release biodegradable polymer releases the therapeutically active ingredient within about 0 hours to about 24 hours after insertion of the microneedle patch to the skin. In some embodiments, the immediate release biodegradable polymer releases at least about 75% of the therapeutically active ingredient on a timescale of about 0 hours to about 24 hours. In some embodiments, the immediate release biodegradable polymer releases about 100% of the therapeutically active ingredient on a timescale of about 0 hours to about 24 hours. In some embodiments, the immediate release biodegradable polymer releases therapeutically active ingredient on a timescale of about 0 hours to about 24 hours in a range of about 75% to about 100%, about 75% to about 95%, about 75% to about 90%, about 75% to about 85%, about 75% to about 80%, about 80% to about 100%, about 80% to about 95%, about 80% to about 90%, about 80% to about 85%, about 85% to about 100%, about 85% to about 95%, about 85% to about 90%, about 90% to about 100%, about 90% to about 95%, about 95% to about 100%, or a value within these ranges. Specific examples may include about 75%, about 80%, about 85%, about 90%, about 95%, about 99%, about 100%, or a range between any two of these values.

In some embodiments, the immediate release biodegradable polymer releases the therapeutically active ingredient within about 0 hours to about 24 hours after insertion of the microneedle patch to the skin. In some embodiments, the immediate release biodegradable polymer releases the therapeutically active ingredient within about 0 minutes to about 10 minutes after insertion of the microneedle patch to the skin. In some embodiments, the immediate release biodegradable polymer releases the therapeutically active ingredient within about 0 minutes to about 5 minutes after insertion of the microneedle patch to the skin. In some embodiments, the immediate release biodegradable polymer releases therapeutically active ingredient within about 0 hours to about 24 hours, about 0 hours to about 23 hours, about 0 hours to about 22 hours, about 0 hours to about 21 hours, about 0 hours to about 20 hours, about 0 hours to about 18 hours, about 0 hours to about 16 hours, about 0 hours to about 14 hours, about 0 hours to about 12 hours, about 0 hours to about 10 hours, about 0 hours to about 9 hours, about 0 hours to about 8 hours, about 0 hours to about 7 hours, about 0 hours to about 6 hours, about 0 hours to about 5 hours, about 0 hours to about 4 hours, about 0 hours to about 3 hours, about 0 hours to about 2 hours, about 0 hours to about 1 hour, about 1 hour to about 24 hours, about 1 hour to about 23 hours, about 1 hour to about 22 hours, about 1 hour to about 21 hours, about 1 hour to about 20 hours, about 1 hour to about 18 hours, about 1 hour to about 16 hours, about 1 hour to about 14 hours, about 1 hour to about 12 hours, about 1 hour to about 10 hours, about 1 hour to about 9 hours, about 1 hour to about 8 hours, about 1 hour to about 7 hours, about 1 hour to about 6 hours, about 1 hour to about 5 hours, about 1 hour to about 4 hours, about 1 hour to about 3 hours, about 1 hour to about 2 hours, about 2 hours to about 24 hours, about 2 hours to about 23 hours, about 2 hours to about 22 hours, about 2 hours to about 21 hours, about 2 hours to about 20 hours, about 2 hours to about 18 hours, about 2 hours to about 16 hours, about 2 hours to about 14 hours, about 2 hours to about 12 hours, about 2 hours to about 10 hours, about 2 hours to about 9 hours, about 2 hours to about 8 hours, about 2 hours to about 7 hours, about 2 hours to about 6 hours, about 2 hours to about 5 hours, about 2 hours to about 4 hours, about 2 hours to about 3 hours, about 5 hours to about 24 hours, about 5 hours to about 23 hours, about 5 hours to about 22 hours, about 5 hours to about 21 hours, about 5 hours to about 20 hours, about 5 hours to about 18 hours, about 5 hours to about 16 hours, about 5 hours to about 14 hours, about 5 hours to about 12 hours, about 5 hours to about 10 hours, about 5 hours to about 9 hours, about 5 hours to about 8 hours, about 5 hours to about 7 hours, about 5 hours to about 6 hours, about 12 hours to about 24 hours, about 12 hours to about 23 hours, about 12 hours to about 22 hours, about 12 hours to about 21 hours, about 12 hours to about 20 hours, about 12 hours to about 18 hours, 12 hours to about 16 hours, about 12 hours to about 14 hours, about 12 hours to about 13 hours, about 18 hours to about 24 hours, about 18 hours to about 23 hours, about 18 hours to about 22 hours, about 18 hours to about 21 hours, about 18 hours to about 20 hours, about 18 hours to about 19 hours, about 20 hours to about 24 hours, about 20 hours to about 23 hours, about 20 hours to about 22 hours, about 20 hours to about 21 hours, about 0 minutes to about 60 minutes, about 0 minutes to about 50 minutes, about 0 minutes to about 45 minutes, about 0 minutes to about 30 minutes, about 0 minutes to about 15 minutes, about 0 minutes to about 10 minutes, about 0 minutes to about 5 minutes, about 0 minutes to about 4 minutes, about 0 minutes to about 3 minutes, 0 minutes to about 2 minutes, 0 minutes to about 1 minute, about 5 minutes to about 60 minutes, about 5 minutes to about 50 minutes, about 5 minutes to about 45 minutes, about 5 minutes to about 30 minutes, about 5 minutes to about 15 minutes, about 5 minutes to about 10 minutes, about 10 minutes to about 60 minutes, about 10 minutes to about 50 minutes, about 10 minutes to about 45 minutes, about 10 minutes to about 30 minutes, about 10 minutes to about 15 minutes, about 15 minutes to about 60 minutes, about 15 minutes to about 50 minutes, about 15 minutes to about 45 minutes, about 15 minutes to about 30 minutes, about 15 minutes to about 25 minutes, about 15 minutes to about 20 minutes, about 30 minutes to about 60 minutes, about 30 minutes to about 50 minutes, about 30 minutes to about 45 minutes, about 30 minutes to about 40 minutes, about 30 minutes to about 35 minutes, about 45 minutes to about 60 minutes, about 45 minutes to about 50 minutes, or a value within these ranges. Specific examples may include about 24 hours, about 23 hours, about 22 hours, about 21 hours, about 20 hours, about 18 hours, about 16 hours, about 14 hours, about 12 hours, about 10 hours, about 9 hours, about 8 hours, about 7 hours, about 6 hours, about 5 hours, about 4 hours, about 3 hours, about 2 hours about 1 hour, about 60 minutes, about 55 minutes, about 50 minutes, about 45 minutes, about 40 minutes, about 35 minutes, about 30 minutes, about 25 minutes, about 20 minutes, about 15 minutes, about 10 minutes, about 9 minutes, about 8 minutes, about 7 minutes, about 6 minutes, about 5 minutes, about 4 minutes about 3 minutes, about 2 minutes, about 1 minute, or a range between any two of these values.

In some embodiments, the method of manufacturing a dissolvable microneedle patch comprising a biodegradable polymer, wherein the biodegradable polymer is capable of providing sustained release of a therapeutically active ingredient after insertion of the microneedle patch into the skin. In further embodiments, the sustained release biodegradable polymer is water soluble and includes PLGA (poly(lactic-co-glycolic acid)), polyglycolic acid, fibroin, PLA (polylactic acid), PVP (polyvinylpyrrolidone), or PCL (polycaprolactone). In further embodiments, the sustained release biodegradable polymer releases the therapeutically active ingredient after about 24 hours of insertion of the microneedle patch to the skin. In some embodiments, the sustained release biodegradable polymer does not release more than 75% of the therapeutically active ingredient until a time greater than about 24 hours after insertion of the microneedle patch to the skin. In some embodiments, the sustained release biodegradable polymer does not release therapeutically active ingredient until a time greater than about 24 hours in amounts of about 75% to about 100%, about 75% to about 99%, about 75% to about 95%, about 75% to about 90%, about 75% to about 85%, about 75% to about 80%, about 80% to about 100%, about 80% to about 99%, about 80% to about 95%, about 80% to about 90%, about 80% to about 85%, about 85% to about 100%, about 85% to about 99%, 85% to about 95%, about 85% to about 90%, about 90% to about 100%, about 90% to about 99%, about 90% to about 95%, about 95% to about 100%, about 95% to about 99%, about 99% to about 100%, or a value within these ranges. Specific examples may include about 75%, about 80% about 85%, about 90%, about 95%, about 99%, about 100%.

In some embodiments, the sustained release biodegradable polymer releases the therapeutically active ingredient over about 1 day to about 30 days. In some embodiments, the sustained release biodegradable polymer releases the therapeutically active ingredient over about 2 days to about 21 days. In some embodiments, the sustained release biodegradable polymer releases the therapeutically active over about 1 day to about 30 days, about 1 day to about 28 days, about 1 day to about 26 days, about 1 day to about 24 days, about 1 days to about 22 days, about 1 day to about 21 days, about 1 day to about 14 days, about 1 day to about 7 days, about 1 day to about 6 days, about 1 day to about 5 days, about 1 day to about 4 days, about 1 day to about 3 days, about 1 day to about 2 days, about 2 days to about 30 days, about 2 days to about 28 days, about 2 days to about 26 days, about 2 days to about 24 days, about 2 days to about 22 days, about 2 days to about 21 days, about 2 days to about 14 days, about 2 days to about 7 days, about 2 days to about 6 days, about 2 days to about 5 days, about 2 days to about 4 days, about 2 days to about 3 days, about 3 days to about 30 days, about 3 days to about 28 days, about 3 days to about 26 days, about 3 days to about 24 days, about 3 days to about 22 days, about 3 days to about 21 days, about 3 days to about 14 days, about 3 days to about 7 days, about 3 days to about 6 days, about 3 days to about 5 days, about 3 days to about 4 days, about 4 days to about 30 days, about 4 days to about 28 days, about 4 days to about 26 days, about 4 days to about 24 days, about 4 days to about 22 days, about 4 days to about 21 days, about 4 days to about 14 days, about 4 days to about 7 days, about 4 days to about 6 days, about 4 days to about 5 days, about 5 days to about 30 days, about 5 days to about 28 days, about 5 days to about 26 days, about 5 days to about 24 days, about 5 days to about 22 days, about 5 days to about 21 days, about 5 days to about 14 days, about 5 days to about 7 days, about 5 days to about 6 days, about 7 days to about 30 day, about 7 days to about 28 days, about 7 days to about 26 days, about 7 days to about 24 days, about 7 days to about 24 days, about 7 days to about 22 days, about 7 days to about 21 days, about 7 days to about 14 days, about 14 days to about 30 days, about 14 days to about 28 days, about 14 days to about 26 days, about 14 days to about 24 days, about 14 days to about 22 days, about 14 days to about 21 days, about 21 days to about 30 days, about 21 days to about 28 days, about 21 days to about 26 days, about 21 days to about 24 days, about 21 days to about 22 days or a value within these ranges. Specific examples may include about 30 days, about 28 days, about 26 days, about 24 days, about 22 days about 21 days, about 14 days, about 7 days, about 6 days, about 5 days, about 4 days, about 3 days, about 2 days, about 1 day or a range between any two of these values.

In some embodiments, the method of manufacturing a dissolvable microneedle patch comprising a biodegradable polymer, wherein the biodegradable polymer is capable of providing both sustained release and immediate release of a therapeutically active ingredient after insertion of the microneedle patch into the skin. In some embodiments, the plurality of microneedles comprise immediate release biodegradable polymer and sustained release biodegradable polymer. In some embodiments, the plurality of microneedles contain immediate release biodegradable polymer at the base of the microneedle and sustained release biodegradable polymer at the tip of the microneedle. In some embodiments, the plurality of microneedles contain immediate release biodegradable polymer at the base of the microneedle and alternating layers of immediate release biodegradable polymer and sustained release biodegradable polymer at the tip of the microneedle.

In some embodiments, the method of manufacturing a dissolvable microneedle patch to treat a skin condition, wherein the method of treating the skin condition comprises applying a dissolvable microneedle patch, wherein the dissolvable microneedle patch is applied on a skin lesion of a patient in need thereof to treat a skin condition. In some embodiments, the dissolvable microneedle patch is applied adjacent to a skin lesion of a patient in need thereof to treat a skin condition. In some embodiments, the dissolvable microneedle patch is applied to an area of the skin that is determined to be optimal based on the age of the patient. In some embodiments, the dissolvable microneedle patch is applied to an area of the skin that is determined to be optimal based on the type of skin in need of treatment.

In some embodiments, the method of manufacturing a dissolvable microneedle patch comprising a plurality of microneedles, wherein the plurality of microneedles are spatially separated within the skin wherein one microneedle does not touch another microneedle. In some embodiments, the dissolvable microneedle patch comprises a plurality of microneedles, wherein the microneedle patch comprises at least about one to about 200 microneedles per square centimeter, about one to about 175 microneedles per square centimeter, about one to about 150 microneedles per square centimeter, about one to about 125 microneedles per square centimeter, about one to about 100 microneedles per square centimeter, about one to about 90 microneedles per square centimeter, about one to about 80 microneedles per square centimeter, about one to about 70 microneedles per square centimeter, about one to about 60 microneedles per square centimeter, about one to about 50 microneedles per square centimeter, about one to about 40 microneedles per square centimeter, about one to about 30 microneedles per square centimeter, about one to about 25 microneedles per square centimeter, about one to about 20 microneedles per square centimeter, about one to about 15, about one to about 10 microneedles per square centimeter, about one to about 5 microneedles per square centimeter, about 5 to about 200 microneedles per square centimeter, about 5 to about 175 microneedles per square centimeter, about 5 to about 150 microneedles per square centimeter, about 5 to about 125 microneedles per square centimeter, about 5 to about 100 microneedles per square centimeter, about 5 to about 90 microneedles per square centimeter, about 5 to about 80 microneedles per square centimeter, about 5 to about 70 microneedles per square centimeter, about 5 to about 60 microneedles per square centimeter, about 5 to about 50 microneedles per square centimeter, about 5 to about 40 microneedles per square centimeter, about 5 to about 30 microneedles per square centimeter, about 5 to about 25 microneedles per square centimeter, about 5 to about 20 microneedles per square centimeter, about 5 to about 15 microneedles per square centimeter, about 5 to about 20 microneedles per square centimeter, about 10 to about 200 microneedles per square centimeter, about 10 to about 175 microneedles per square centimeter, about 10 to about 150 microneedles per square centimeter, about 10 to about 150 microneedles per square centimeter, about 10 to about 125 microneedles per square centimeter, about 10 to about 100 microneedles per square centimeter, about 10 to about 90 microneedles per square centimeter, about 10 to about 80 microneedles per square centimeter, about 10 to about 70 microneedles per square centimeter, about 10 to about 60 microneedles per square centimeter, about 10 to about 50 microneedles per square centimeter, about 10 to about 40 microneedles per square centimeter, about 10 to about 30 microneedles per square centimeter, about 10 to about 25 microneedles per square centimeter, about 10 to about 20 microneedles per square centimeter, about 10 to about 15 microneedles per square centimeter, about 25 to about 200 microneedles per square centimeter, about 25 to about 175 microneedles per square centimeter, about 25 to about 150 microneedles per square centimeter, about 25 to about 125 microneedles per square centimeter, about 25 to about 100 microneedles per square centimeter, about 25 to about 90 microneedles per square centimeter, about 25 to about 80 microneedles per square centimeter, about 25 to about 70 microneedles per square centimeter, about 25 to about 60 microneedles per square centimeter, about 25 to about 50 microneedles per square centimeter, about 25 to about 40 microneedles per square centimeter, about 25 to about 30 microneedles per square centimeter, about 50 to about 200 microneedles per square centimeter, about 50 to about 175 microneedles per square centimeter, about 50 to about 150 microneedles per square centimeter, about 50 to about 125 microneedles per square centimeter, about 50 to about 100 microneedles per square centimeter, about 50 to about 90 microneedles per square centimeter, about 50 to about 80 microneedles per square centimeter, about 50 to about 70 microneedles per square centimeter, about 50 to about 60 microneedles per square centimeter, about 75 to about 200 microneedles per square centimeter, about 75 to about 175 microneedles per square centimeter, about 75 to about 150 microneedles per square centimeter, about 75 to about 125 microneedles per square centimeter, about 75 to about 100 microneedles per square centimeter, about 75 to about 90 microneedles per square centimeter, about 75 to about 80 microneedles per square centimeter, about 100 to about 200 microneedles per square centimeter, about 100 to about 175 microneedles per square centimeter, about 100 to about 150 microneedles per square centimeter, about 100 to about 125 microneedles per square centimeter, about 125 to about 200 microneedles per square centimeter, about 125 to about 175 microneedles per square centimeter, about 125 to about 150 microneedles per square centimeter, about 150 to about 200 microneedles per square centimeter, about 150 to about 175 microneedles per square centimeter, about 175 to about 200 microneedles per square centimeter, or a value within these ranges. Specific examples may include a dissolvable microneedle patch comprising a plurality of microneedles, wherein the microneedle patch comprises at least about 200 microneedles per square centimeter, at least about 175 microneedles per square centimeter, at least about 150 microneedles per square centimeter, at least about 125 microneedles per square centimeter, at least about 100 microneedles per square centimeter, at least about 90 microneedles per square centimeter, at least about 80 microneedles per square centimeter, at least about 70 microneedles per square centimeter, at least about 60 microneedles per square centimeter, at least about 50 microneedles per square centimeter, at least about 40 microneedles per square centimeter, at least about 30 microneedles per square centimeter, at least about 25 microneedles per square centimeter, at least about 20 microneedles per square centimeter, at least about 15 microneedles per square centimeter, at least about 10 microneedles per square centimeter, at least about 5 microneedles per square centimeter, at least about 4 microneedles per square centimeter, at least about 3 microneedles per square centimeter, at least about 2 microneedles per square centimeter, at least about 1 microneedle per square centimeter, or a range between any two of these values.

In some embodiments, the method of manufacturing a dissolvable microneedle patch, wherein the dissolvable microneedle patch is any shape necessary to accommodate the surface topology of the skin. In some embodiments, the dissolvable microneedle patch has any of n number of sides with n ranging from about 0 sides to about 1000 sides. In some embodiments, the dissolvable microneedle patch has about 0 sides to about 1000 sides, about 0 sides to about 900 sides, about 0 sides to about 800 sides, about 0 sides to about 700 sides, about 0 sides to about 600 sides, about 0 sides to about 500 sides, about 0 sides to about 400 sides, about 0 sides to about 300 sides, about 0 sides to about 200 sides, about 0 sides to about 100 sides, about 0 sides to about 90 sides, about 0 sides to about 80 sides, about 0 sides to about 70 sides, about 0 sides to about 60 sides, about 0 sides to about 50 sides, about 0 sides to about 40 sides, about 0 sides to about 30 sides, about 0 sides to about 20 sides, about 0 sides to about 10 sides, about 0 sides to about 9 sides, about 0 sides to about 8 sides, about 0 sides to about 7 sides, about 0 sides to about 6 sides, about 0 sides to about 5 sides, about 0 sides to about 4 sides, about 0 sides to about 3 sides, about 0 sides to about 2 sides, about 10 sides to about 1000 sides, about 10 sides to about 900 sides, about 10 sides to about 800 sides, about 10 sides to about 700 sides, about 10 sides to about 600 sides, about 10 sides to about 500 sides, about 10 sides to about 400 sides, about 10 sides to about 300 sides, about 10 sides to about 200 sides, about 10 sides to about 100 sides, about 10 sides to about 90 sides, about 10 sides to about 80 sides, about 10 sides to about 70 sides, about 10 sides to about 60 sides, about 10 sides to about 50 sides, about 10 sides to about 40 sides, about 10 sides to about 30 sides, about 10 sides to about 20 sides, about 20 sides to about 1000 sides, about 20 sides to about 900 sides, about 20 sides to about 800 sides, about 20 sides to about 700 sides, about 20 sides to about 600 sides, about 20 sides to about 500 sides, about 20 sides to about 400 sides, about 20 sides to about 300 sides, about 20 sides to about 200 sides, about 20 sides to about 100 sides, about 20 sides to about 90 sides, about 20 sides to about 80 sides, about 20 sides to about 70 sides, about 20 sides to about 60 sides, about 20 sides to about 50 sides, about 20 sides to about 40 sides, about 20 sides to about 30 sides, about 30 sides to about 1000 sides, about 30 sides to about 900 sides, about 30 sides to about 800 sides, about 30 sides to about 700 sides, about 30 sides to about 600 sides, about 30 sides to about 500 sides, about 30 sides to about 400 sides, about 30 sides to about 300 sides, about 30 sides to about 200 sides, about 30 sides to about 100 sides, about 30 sides to about 90 sides, about 30 sides to about 80 sides, about 30 sides to about 70 sides, about 30 sides to about 60 sides, about 30 sides to about 50 sides, about 30 sides to about 40 sides, about 50 sides to about 1000 sides, about 50 sides to about 900 sides, about 50 sides to about 800 sides, about 50 sides to about 700 sides, about 50 sides to about 600 sides, about 50 sides to about 500 sides, about 50 sides to about 400 sides, about 50 sides to about 300 sides, about 50 sides to about 200 sides, about 50 sides to about 100 sides, about 50 sides to about 90 sides, about 50 sides to about 80 sides, about 50 sides to about 70 sides, about 50 sides to about 60 sides, about 75 side to about 1000 sides, about 75 to about 900 sides, about 75 to about 800 sides, about 75 to about 700 sides, about 75 to about 600 sides, about 75 to about 500 sides, about 75 to about 400 sides, about 75 to about 300 sides, about 75 to about 200 sides, about 75 to about 200 sides, about 75 to about 100 sides, about 75 to about 90 sides, about 75 to about 80 sides, about 100 sides to about 1000 sides, about 100 sides to about 900 sides, about 100 sides to about 800 sides, about 100 sides to about 700 sides, about 100 sides to about 600 sides, about 100 sides to about 500 sides, about 100 sides to about 400 sides, about 100 sides to about 300 sides, about 100 sides to about 200 sides, about 250 sides to about 1000 sides, about 250 sides to about 900 sides, about 250 sides to about 800 sides, about 250 to about 700 sides, about 250 sides to about 600 sides, about 250 sides to about 500 sides, about 250 sides to about 400 sides, about 250 sides to about 300 sides, about 500 sides to about 1000 sides, about 500 sides to about 900 sides, about 500 sides to about 800 sides, about 500 sides to about 700 sides, about 500 sides to about 600 sides, about 750 sides to about 1000 sides, about 750 sides to about 900 sides, about 750 sides to about 800 sides, about 900 sides to about 1000 sides or a value within these ranges. Specific examples may include a dissolvable microneedle patch has about 1000 sides, about 900 sides, about 800 sides, about 700 sides, about 600 sides, about 500 sides, about 400 sides, about 300 sides, about 200 sides, about 100 sides, about 90 sides, about 80 sides, about 70 sides, about 60 sides, about 50 sides, about 40 sides, about 30 sides, about 20 sides, about 10 sides, about 9 sides, about 8 sides, about 7 sides, about 6 sides, about 5 sides, about 4 sides, about 3 sides, about 2 sides, or a range between any two of these values.

In some embodiments, the method of manufacturing a dissolvable microneedle patch, wherein the dissolvable microneedle patch may have sides of equal length. In further embodiments, the dissolvable microneedle patch may have sides of unequal length. In some embodiments, the dissolvable microneedle patch is shaped as a medical bandage. In some embodiments, the dissolvable microneedle patch ranges in size from about 0.1 square centimeters to about 1000 square centimeters, about 0.1 square centimeters to about 900 square centimeters, about 0.1 square centimeters to about 800 square centimeters, about 0.1 square centimeters to about 700 square centimeters, about 0.1 square centimeters to about 600 square centimeters, about 0.1 square centimeters to about 500 square centimeters, about 0.1 square centimeters to about 400 square centimeters, about 0.1 square centimeters to about 300 square centimeters, about 0.1 square centimeters to about 200 square centimeters, about 0.1 square centimeters to about 100 square centimeters, about 0.1 square centimeters to about 90 square centimeters, about 0.1 square centimeters to about 80 square centimeters, about 0.1 square centimeters to about 70 square centimeters, about 0.1 square centimeters to about 60 square centimeters, about 0.1 square centimeters to about 50 square centimeters, about 0.1 square centimeters to about 40 square centimeters, about 0.1 square centimeters to about 30 square centimeters, about 0.1 square centimeters to about 20 square centimeters, about 0.1 square centimeters to about 10 square centimeters, about 0.1 square centimeters to about 5 square centimeters, about 0.1 square centimeters to about 4 square centimeters, about 0.1 square centimeters to about 3 square centimeters, about 0.1 square centimeters to about 2 square centimeters, about 0.1 square centimeters to about 1 square centimeters, about 0.1 square centimeters to about 0.9 square centimeters, about 0.1 square centimeters to about 0.8 square centimeters, about 0.1 square centimeters to about 0.7 square centimeters, about 0.1 square centimeters to about 0.6 square centimeters, about 0.1 square centimeters to about 0.5 square centimeters, about 0.1 square centimeters to about 0.4 square centimeters, about 0.1 square centimeters to about 0.3 square centimeters, about 0.1 square centimeters to about 0.2 square centimeters, about 0.5 square centimeters to about 1000 square centimeters, about 0.5 square centimeters to about 900 square centimeters, about 0.5 square centimeters to about 800 square centimeters, about 0.5 square centimeters to about 700 square centimeters, about 0.5 square centimeters to about to about 600 square centimeters, about 0.5 square centimeters to about to about 500 square centimeters, about 0.5 square centimeters to about 400 square centimeters, about 0.5 square centimeters to about 300 square centimeters, about 0.5 square centimeters to about 200 square centimeters, about 0.5 square centimeters to about 100 square centimeters, about 0.5 square centimeters to about 90 square centimeters, about 0.5 square centimeters to about 80 square centimeters, about 0.5 square centimeters to about 70 square centimeters, about 0.5 square centimeters to about 60 square centimeters, about 0.5 square centimeters to about 50 square centimeters, about 0.5 square centimeters to about 40 square centimeters, about 0.5 square centimeters to about 30 square centimeters, about 0.5 square centimeters to about 20 square centimeters, about 0.5 square centimeters to about 10 square centimeters, about 0.5 square centimeters to about 5 square centimeters, about 0.5 square centimeters to about 4 square centimeters, about 0.5 square centimeters to about 3 square centimeters, about 0.5 square centimeters to about 2 square centimeters, about 0.5 square centimeters to about 1 square centimeters, about 0.5 square centimeters to about 0.9 square centimeters, about 0.5 square centimeters to about 0.8 square centimeters, about 0.5 square centimeters to about 0.7 square centimeters, about 0.5 square centimeters to about 0.6 square centimeters, about 1 square centimeters to about 1000 square centimeters, about 1 square centimeters to about 900 square centimeters, about 1 square centimeters to about 800 square centimeters, about 1 square centimeters to about 700 square centimeters, about 1 square centimeters to about 600 square centimeters, about 1 square centimeters to about 500 square centimeters, about 1 square centimeters to about 400 square centimeters, about 1 square centimeters to about 300 square centimeters, about 1 square centimeters to about 200 square centimeters, about 1 square centimeters to about 100 square centimeters, about 1 square centimeters to about 90 square centimeters, about 1 square centimeters to about 80 square centimeters, about 1 square centimeters to about 70 square centimeters, about 1 square centimeters to about 60 square centimeters, about 1 square centimeters to about 50 square centimeters, about 1 square centimeters to about 40 square centimeters, about 1 square centimeters to about 30 square centimeters, about 1 square centimeters to about 20 square centimeters, about 1 square centimeters to about 10 square centimeters, about 1 square centimeters to about 5 square centimeters, about 1 square centimeters to about 4 square centimeters, about 1 square centimeters to about 3 square centimeters, about 1 square centimeters to about 2 square centimeters, about 10 square centimeters to about 1000 square centimeters, about 10 square centimeters to about 900 square centimeters, about 10 square centimeters to about 800 square centimeters, about 10 square centimeters to about 700 square centimeters, about 10 square centimeters to about 600 square centimeters, about 10 square centimeters to about 500 square centimeters, about 10 square centimeters to about 400 square centimeters, about 10 square centimeters to about 300 square centimeters, about 10 square centimeters to about 200 square centimeters, about 10 square centimeters to about 100 square centimeters, about 10 square centimeters to about 90 square centimeters, about 10 square centimeters to about 80 square centimeters, about 10 square centimeters to about 70 square centimeters, about 10 square centimeters to about 60 square centimeters, about 10 square centimeters to about 50 square centimeters, about 10 square centimeters to about 40 square centimeters, about 10 square centimeters to about 30 square centimeters, about 10 square centimeters to about 20 square centimeters, about 50 square centimeters to about 1000 square centimeters, about 50 square centimeters to about 900 square centimeters, about 50 square centimeters to about 800 square centimeters, about 50 square centimeters to about 700 square centimeters, about 50 square centimeters to about 600 square centimeters, about 50 square centimeters to about 500 square centimeters, about 50 square centimeters to about 400 square centimeters, about 50 square centimeters to about 300 square centimeters, about 50 square centimeters to about 200 square centimeters, about 50 square centimeters to about 100 square centimeters, about 75 square centimeters to about 1000 square centimeters, about 75 square centimeters to about 900 square centimeters, about 75 square centimeters to about 800 square centimeters, about 75 square centimeters to about 700 square centimeters, about 75 square centimeters to about 600 square centimeters, about 75 square centimeters to about 500 square centimeters, about 75 square centimeters to about 400 square centimeters, about 75 square centimeters to about 300 square centimeters, about 75 square centimeters to about 200 square centimeters, about 75 square centimeters to about 100 square centimeters, about 100 square centimeters to about 1000 square centimeters, about 100 square centimeters to about 900 square centimeters, about 100 square centimeters to about 800 square centimeters, about 100 square centimeters to about 700 square centimeters, about 100 square centimeters to about 600 square centimeters, about 100 square centimeters to about 500 square centimeters, about 100 square centimeters to about 400 square centimeters, about 100 square centimeters to about 300 square centimeters, about 100 square centimeters to about 200 square centimeters, about 250 square centimeters to about 1000 square centimeters, about 250 square centimeters to about 900 square centimeters, about 250 square centimeters to about 800 square centimeters, about 250 square centimeters to about 700 square centimeters, about 250 square centimeters to about 600 square centimeters, about 250 square centimeters to about 500 square centimeters, about 250 square centimeters to about 400 square centimeters, about 250 square centimeters to about 300 square centimeters, about 500 square centimeters to about 1000 square centimeters, about 500 square centimeters to about 900 square centimeters, about 500 square centimeters to about 800 square centimeters, about 500 square centimeters to about 700 square centimeters, about 500 square centimeters to about 600 square centimeters, about 750 square centimeters to about 1000 square centimeters, about 750 square centimeters to about 900 square centimeters, about 750 square centimeters to about 800 square centimeters, or a range between any two of these values. Specific examples of the dissolvable microneedle patch range in size from about 1000 square centimeters, about 900 square centimeters, about 800 square centimeters, about 700 square centimeters, about 600 square centimeters, about 500 square centimeters, about 400 square centimeters, about 300 square centimeters, about 200 square centimeters, about 100 square centimeters, about 90 square centimeters, about 80 square centimeters, about 70 square centimeters, about 60 square centimeters, about 50 square centimeters, about 40 square centimeters, about 30 square centimeters, about 20 square centimeters, about 10 square centimeters, about 5 square centimeters, about 4 square centimeters, about 3 square centimeters, about 2 square centimeters, about 1 square centimeters, about 0.9 square centimeters, about 0.8 square centimeters, about 0.7 square centimeters, about 0.6 square centimeters, about 0.7 square centimeters, about 0.6 square centimeters, about 0.5 square centimeters, about 0.4 square centimeters, about 0.3 square centimeters, about 0.2 square centimeters, about 0.1 square centimeters, or a range between any two of these values.

In some embodiments, the method of manufacturing a dissolvable microneedle patch, wherein the dissolvable microneedle patch comprises a backing layer and a microneedle layer. In some embodiments, the dissolvable microneedle patch comprises a backing layer and a microneedle layer wherein the microneedle layer is placed directly on top of the skin. In some embodiments, the dissolvable microneedle patch comprises a backing layer wherein the backing layer is composed of adhesive medical tape. In some embodiments, the dissolvable microneedle patch comprises a backing layer wherein the backing layer comprises a therapeutically active ingredient.

In some embodiments, the method of manufacturing a dissolvable microneedle patch, wherein the dissolvable microneedle patch comprises a backing layer wherein the backing layer is a removable substrate. In some embodiments, the dissolvable microneedle patch wherein the removable substrate comprises an adhesive medical tape. In some embodiments, the backing layer comprises a quick dissolving polymer. In some embodiments, the dissolvable microneedle patch wherein the removable substrate comprises a therapeutically active ingredient dispersed in a polymer. In some embodiments, the dissolvable microneedle patch wherein the plurality of microneedles are attached to the removable substrate and comprise a tapered tip that extends away from the removal substrate. In some embodiments, the dissolvable microneedle patch wherein the removable substrate releases at least about 90% of the microneedles from the adhesive surface within a period of about 20 minutes after application to skin. In some embodiments, the dissolvable microneedle patch wherein the removable substrate releases at least about 90% of the microneedles from the adhesive surface within a period of about 5 minutes after application to skin. In some embodiments, the dissolvable microneedle patch wherein 90% of the microneedles are released from the adhesive surface within a period of about 0 minutes to about 20 minutes, about 0 minutes to about 15 minutes, about 0 minutes to about 10 minutes, about 0 minutes to about 9 minutes, about 0 minutes to about 8 minutes, about 0 minutes to about 7 minutes, about 0 minutes to about 6 minutes, about 0 minutes to about 5 minutes, about 0 minutes to about 4 minutes, about 0 minutes to about 3 minutes, about 0 minutes to about 2 minutes, about 0 minutes to about 1 minutes, about 1 minute to about 20 minutes, about 1 minute to about 15 minutes, about 1 minute to about 10 minutes, about 1 minute to about 9 minutes, about 1 minute to about 8 minutes, about 1 minute to about 7 minutes, about 1 minute to about 6 minutes, about 1 minute to about 5 minutes, about 1 minute to about 4 minutes, about 1 minute to about 3 minutes, about 1 minute to about 2 minutes, about 2 minutes to about 20 minutes, about 2 minutes to about 15 minutes, about 2 minutes to about 10 minutes, about 2 minutes to about 9 minutes, about 2 minutes to about 8 minutes, about 2 minutes to about 7 minutes, about 2 minutes to about 6 minutes, about 2 minutes to about 5 minutes, about 2 minutes to about 4 minutes, about 2 minutes to about 3 minutes, about 5 minutes to about 20 minutes, about 5 minutes to about 15 minutes, about 5 minutes to about 10 minutes, about 5 minutes to about 9 minutes, about 5 minutes to about 8 minutes, about 5 minutes to about 7 minutes, about 5 minutes to about 6 minutes, about 10 minutes to about 20 minutes, about 10 minutes to about 15 minutes, about 15 minutes to about 20 minutes, about 0 seconds to about 60 seconds, about 0 seconds to about 0 seconds to about 45 seconds, about 0 seconds to about 30 seconds, about 0 seconds to about 15 seconds, about 0 seconds to about 10 seconds, about 0 seconds to about 9 seconds, about 0 seconds to about 8 seconds, about 0 seconds to about 7 seconds, about 0 seconds to about 6 seconds, about 0 seconds to about 5 seconds, about 0 seconds to about 4 seconds, about 0 seconds to about 3 seconds, about 0 seconds to about 2 seconds, about 0 seconds to about 1 seconds, about 1 second to about 60 seconds, about 1 second to about 45 seconds, about 1 second to about 30 seconds, about 1 second to about 15 seconds, about 1 second to about 10 seconds, about 1 second to about 9 seconds, about 1 second to about 8 seconds, about 1 second to about 7 seconds, about 1 second to about 6 seconds, about 1 second to about 5 seconds, about 1 second to about 4 seconds, about 1 second to about 3 seconds, about 1 second to about 2 seconds, about 2 seconds to about 60 seconds, about 2 seconds to about 45 seconds, about 2 seconds to about 30 seconds, about 2 seconds to about 15 seconds, about 2 seconds to about 10 seconds, about 2 seconds to about 9 seconds, about 2 seconds to about 8 seconds, about 2 seconds to about 7 seconds, about 2 seconds to about 6 seconds, about 2 seconds to about 5 seconds, about 2 seconds to about 4 seconds, about 2 seconds to about 3 seconds, about 5 seconds to about 60 seconds, about 5 seconds to about 45 seconds, about 5 seconds to about 30 seconds, about 5 seconds to about 15 seconds, about 5 seconds to about 10 seconds, about 5 seconds to about 9 seconds, about 5 seconds to about 8 seconds, about 5 seconds to about 7 seconds, about 5 seconds to about 6 seconds, about 10 seconds to about 60 seconds, about 10 seconds to about 45 seconds, about 10 seconds to about 30 seconds, about 10 seconds to about 15 seconds, about 15 seconds to about 60 seconds, about 15 seconds to about 45 seconds, about 15 seconds to about 30 seconds, about 30 seconds to about 60 seconds, about 30 seconds to about 45 seconds, about 45 seconds to about 60 seconds, or a value within these ranges. In specific examples, 90% of the microneedles are released from the adhesive surface of the dissolvable microneedle patch within about 20 minutes, about 15 minutes, about 10 minutes, about 9 minutes, about 8 minutes, about 7 minutes, about 6 minutes, about 5 minutes, about 4 minutes, about 3 minutes, about 2 minutes, about 1 minute, about 60 seconds, about 45 seconds, about 30 seconds, about 15 seconds, about 10 seconds, about 9 seconds, about 8 seconds, about 7 seconds, about 6 seconds, about 5 seconds, about 4 seconds, about 3 seconds, about 2 seconds, about 1 second or a range between any two of these values.

In some embodiments, the method of manufacturing a dissolvable microneedle patch comprising a backing layer, wherein the backing layer overlays the base of the tip portion in such a manner that each microneedle is separated from the other microneedles on the patch and forms a discrete entity when the substrate is removed upon application of the patch on the skin.

In some embodiments, the method of manufacturing a dissolvable microneedle patch, wherein the dissolvable microneedle patch is (i) placed on a surface area of the skin of a patient in need of treatment, or pre-treatment testing to assess for hypersensitivity reaction, general tolerability, or other adverse events, (ii) exerting sufficient force on the patch composition to permit the microneedles to penetrate through the epidermis into the papillary dermis, and (iii) allowing the plurality of microneedles to remain in the skin until the biodegradable polymer degrades, and (iv) removing the adhesive substrate from the patch composition, wherein the step (ii) is carried out by applying pressure with a finger, wherein the pressure is sufficient for a force ranging from about 0N to about 1,000N. In the preferred embodiment of the present application, the pressure applied is about 10N. In an alternate embodiment of the present application the step (ii) is carried out by impact insertion using an applicator device, wherein the pressure is sufficient for a force ranging from about 0 to about 1,000N. In the preferred embodiment of the present application, the pressure applied is about 10N. In some embodiments, the force applied by a finger or an applicator device ranges from about 0N to about 1,000 N, about 0N to about 900N, about 0N to about 800N, about 0N to about 700N, about 0N to about 600N, about 0N to about 500N, about 0N to about 400N, about 0N to about 300N, about 0N to about 200N, about 0N to about 100N, about 0N to about 90N, about 0N to about 80N, about 0N to about 70N, about 0N to about 60N, about 0N to about 50N, about 0N to about 40N, about 0N to about 30N, about 0N to about 20N, about 0N to about 10N, about 0N to about 9N, about 0N to about 8N, about 0N to about 7N, about 0N to about 6N, about 0N to about 5N, about 0N to about 4N, about 0N to about 3N, about 0N to about 2N, about 0 N to about 1N, about 0N to about 0.9N, about 0N to about 0.8N, about 0N to about 0.7N, about 0N to about 0.6N, about 0N to about 0.5N, about 0N to about 0.4N, about 0N to about 0.3N, about 0N to about 0.2N, about 0N to about 0.1N, about 0.1N to about 1000N, about 0.1N to about 900N, about 0.1 N to about 800N, about 0.1N to about 700N, about 0.1N to about 600N, about 0.1N to about 500N, about 0.1N to about 400N, about 0.1N to about 300N, about 0.1N to about 200N, about 0.1N to about 100N, about 0.1N to about 90N, about 0.1N to about 80N, about 0.1N to about 70N, about 0.1N to about 60N, about 0.1N to about 50N, about 0.1N to about 40N, about 0.1N to about 30N, about 0.1N to about 20N, about 0.1N to about 10N, about 9N, about 0.1N to about 8N, about 0.1N to about 7N, about 0.1N to about 6N, about 0.1N to about 5N, about 0.1N to about 4N, about 0.1N to about 3N, about 0.1N to about 2N, about 0.1N to about 1N, about 0.1N to about 0.9N, about 0.1N to about 0.8N, about 0.1N to about 0.7N, about 0.1N to about 0.6N, about 0.1N to about 0.5N, about 0.1N to about 0.4N, about 0.1N to about 0.3N, about 0.1N to about 0.2N, about 1N to about 1000N, about 1N to about 900N, about 1N to about 800 N, about 1N to about 700N, about 1N to about 600N, about 1N to about 500N, about 1N to about 400N, about 1N to about 300N, about 1N to about 200N, about 1N to about 100N, about 1N to about 90N, about 1N to about 80N, about 1N to about 70N, about 1N to about 60N, about 1N to about 50N, about 1N to about 40N, about 1N to about 30N, about 1N to about 20N, about 1N to about 10N, about 1N to about 9N, about 1N to about 8N, about 1N to about 7N, about 1N to about 6N, about 1N to about 5N, about 1N to about 4N, about 1N to about 3N, about 1N to about 2N, about 10N to about 1000N, about 10N to about 900 N, about 10N to about 800N, about 10N to about 700N, about 10N to about 600N, about 10N to about 500N, about 10N to about 400N, about 10N to about 300N, about 10N to about 200N, about 10N to about 100N, about 10N to about 90N, about 10N to about 80N, about 10N to about 70N, about 10N to about 60N, about 10N to about 50N, about 10N to about 40N, about 10N to about 30N, about 10N to about 20N, about 50N to about 1000N, about 50N to about 900N, about 50N to about 800N, about 50N to about 700N, about 50N to about 600N, about 50N to about 500N, about 50N to about 400N, about 50N to about 300N, about 50N to about 200N, about 50N to about 100N, about 100N to about 1000N, about 100N to about 900N, about 100N to about 800N, about 100N to about 700N, about 100N to about 600N, about 100N to about 500N, about 100N to about 400N, about 100N to about 300N, about 100N to about 200N, about 200N to about 1000N, about 200N to about 900N, about 200N to about 800N, about 200N to about 700N, about 200N to about 600N, about 200N to about 500N, about 200N to about 400N, about 200N to about 300N, about 500N to about 1000N, about 500N to about 900N, about 500N to about 800N, about 500N to about 700N, about 500N to about 600N, or a value within these ranges. In specific examples, the force applied by a finger or an applicator device is about 0N, about 0.1N, about 0.2N, about 0.3N, about 0.4N, about 0.5N, about 0.6N, about 0.7N, about 0.8N, about 0.9N, about 1N, about 2N, about 3N, about 4N, about 5N, about 6N, about 7N, about 8N, about 9N, about 10N, about 15N, about 20N, about 30N, about 40N, about 50N, about 60N, about 70N, about 80N, about 90N, about 100N, about 200N, about 300N, about 400N, about 500N, about 600N, about 700N, about 800N, about 900N, or a range between and two of these values.

In some embodiments, the method of manufacturing a dissolvable microneedle patch, wherein the dissolvable microneedle patch is (i) placed on a surface area of the skin of a patient in need of treatment, or pre, treatment testing to assess for hypersensitivity reaction, general tolerability, or other adverse events, (ii) exerting sufficient force on the patch composition to permit the microneedles to penetrate through the epidermis into the papillary dermis, wherein the sufficient force is applied by impact insertion using an applicator device. In some embodiments, the sufficient force applied by impact insertion ranges from 0N to about 1000N. In some embodiments, the sufficient force applied by impact insertion is 10N.

In some embodiments, the method of manufacturing a dissolvable microneedle patch comprising immediate release polymer and sustained release polymer for delivery of a therapeutically active ingredient to treat a skin condition, wherein the skin condition comprises a viral condition or a neoplastic condition.

In some embodiments, the method of manufacturing a dissolvable microneedle patch comprising immediate release polymer for delivery of a therapeutically active ingredient to treat a skin condition, wherein the skin condition comprises alopecia areata or vitiligo. In some embodiments, the method of manufacturing a dissolvable microneedle patch comprising immediate release polymer for delivery of a therapeutically active ingredient, wherein the method comprises a medical procedure for testing allergies or hypersensitivity to the therapeutically active agent.

Embodiments of the application are directed to the method of manufacturing a dissolvable microneedle patch, wherein the dissolvable microneedle patch is used to test a patient in need thereof for allergies comprising applying a dissolvable microneedle patch for delivery of a therapeutically active ingredient to the skin; exerting sufficient force on the dissolvable microneedle patch to permit the microneedles to penetrate to a location selected from the group consisting of the epidermis, the dermis and the papillary dermis; removing adhesive substrate from the patch composition; and allowing the plurality of microneedles to remain in the skin until the biodegradable polymer degrades.

In some embodiments, the method manufacturing a dissolvable microneedle patch, wherein the dissolvable microneedle patch is used to test a patient in need thereof for hypersensitivity comprising applying a dissolvable microneedle patch for delivery of a therapeutically active ingredient to the skin; exerting sufficient force on the dissolvable microneedle patch to permit the microneedles to penetrate to a location selected from the group consisting of the epidermis, the dermis and the papillary dermis; removing adhesive substrate from the patch composition; and allowing the plurality of microneedles to remain in the skin until the biodegradable polymer degrades.

In some embodiments, the method manufacturing a dissolvable microneedle patch, wherein the dissolvable microneedle patch is used to sensitize a patient in need thereof comprising applying a dissolvable microneedle patch for delivery of a therapeutically active ingredient to the skin; exerting sufficient force on the dissolvable microneedle patch to permit the microneedles to penetrate to a location selected from the group consisting of the epidermis, the dermis and the papillary dermis; removing adhesive substrate from the patch composition; and allowing the plurality of microneedles to remain in the skin until the biodegradable polymer degrades.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

EXAMPLES

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples:

Example 1

Microneedle Patch

Two reverse microneedle molds with an array of 100 microneedles in a square configuration were created using polydimethylsiloxane elastomer (SLYGARD 184, Dow).

Figure 2:
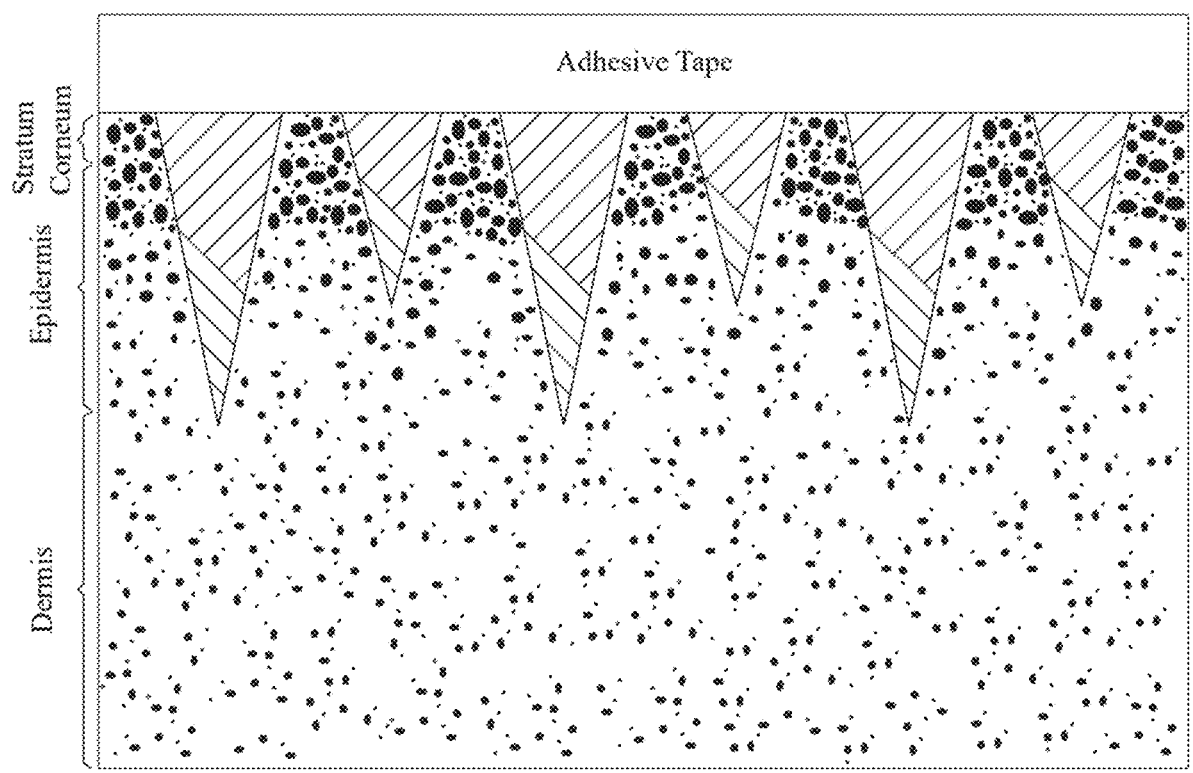
FIG. 2 is an illustration of the microneedle patch of the present application, viewed from the side, applied to the skin of a patient wherein the stratum corneum, epidermis and dermis are labeled to demonstrate the penetrance of the microneedles to deliver active ingredients in various strata of the skin.

The dimensions of the microneedles to be created by these molds were square pyramids with a base width and length of 200 microns and lengths of 500 microns and 800 microns, respectively. The microneedles cast in these molds would obtain a configuration similar to FIG. 1. In the preferred embodiment, these varying length microneedles would alternate 1:1 within the same patch approximating a configuration upon skin insertion seen in FIG. 2. This alternating length configuration ensures concentrated delivery of active ingredient simultaneously into the epidermis and dermis where key inflammatory cells of the immune system reside, namely Langerhans cells in the epidermis and dermal dendritic cells in the dermis.

Example 2

Microneedle Patch

Figure 3:
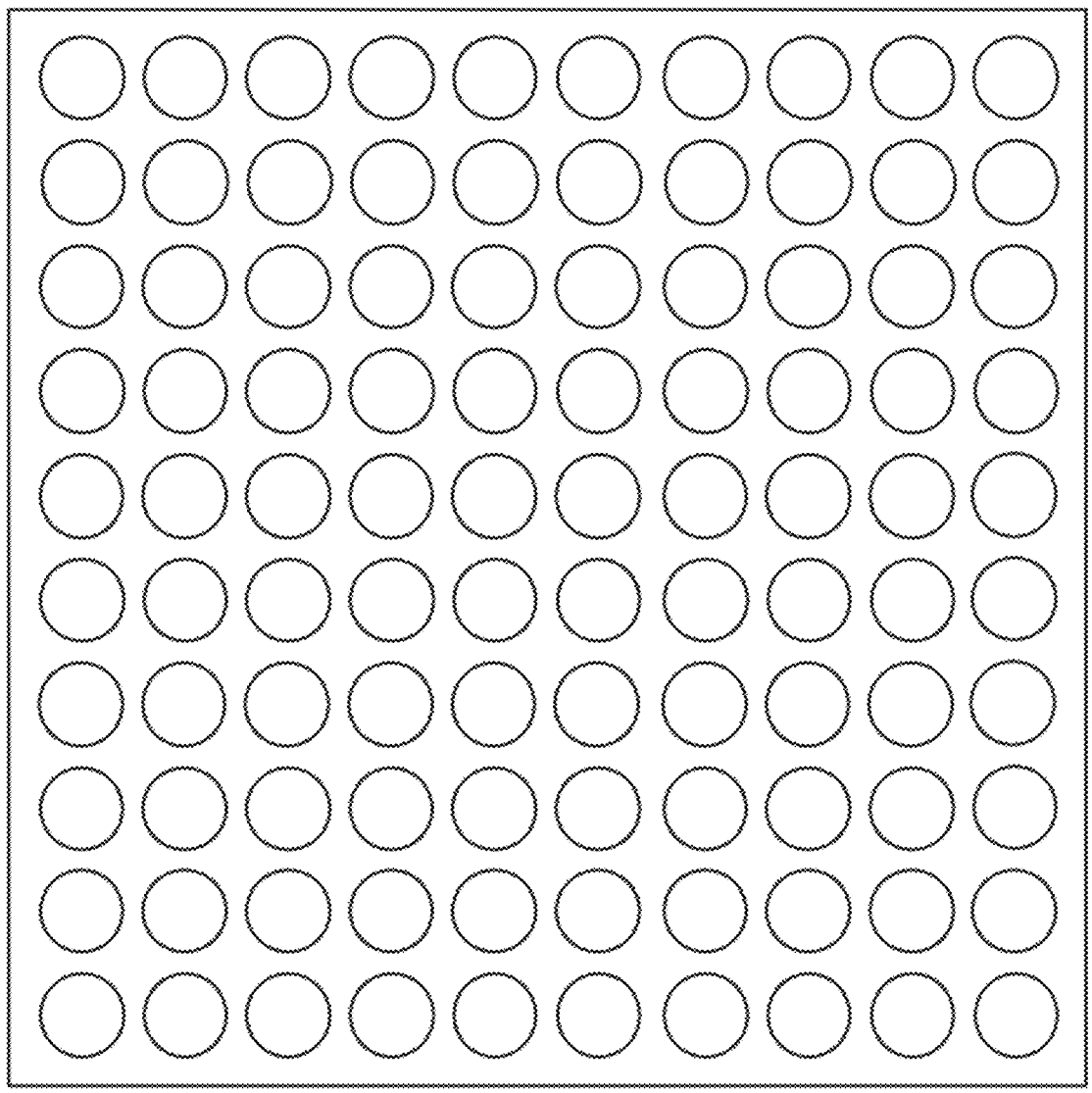
FIG. 3 is an illustration of the microneedle patch of the present application as viewed from the top, if the adhesive were translucent, to show cone shaped needles below.
Figure 4:
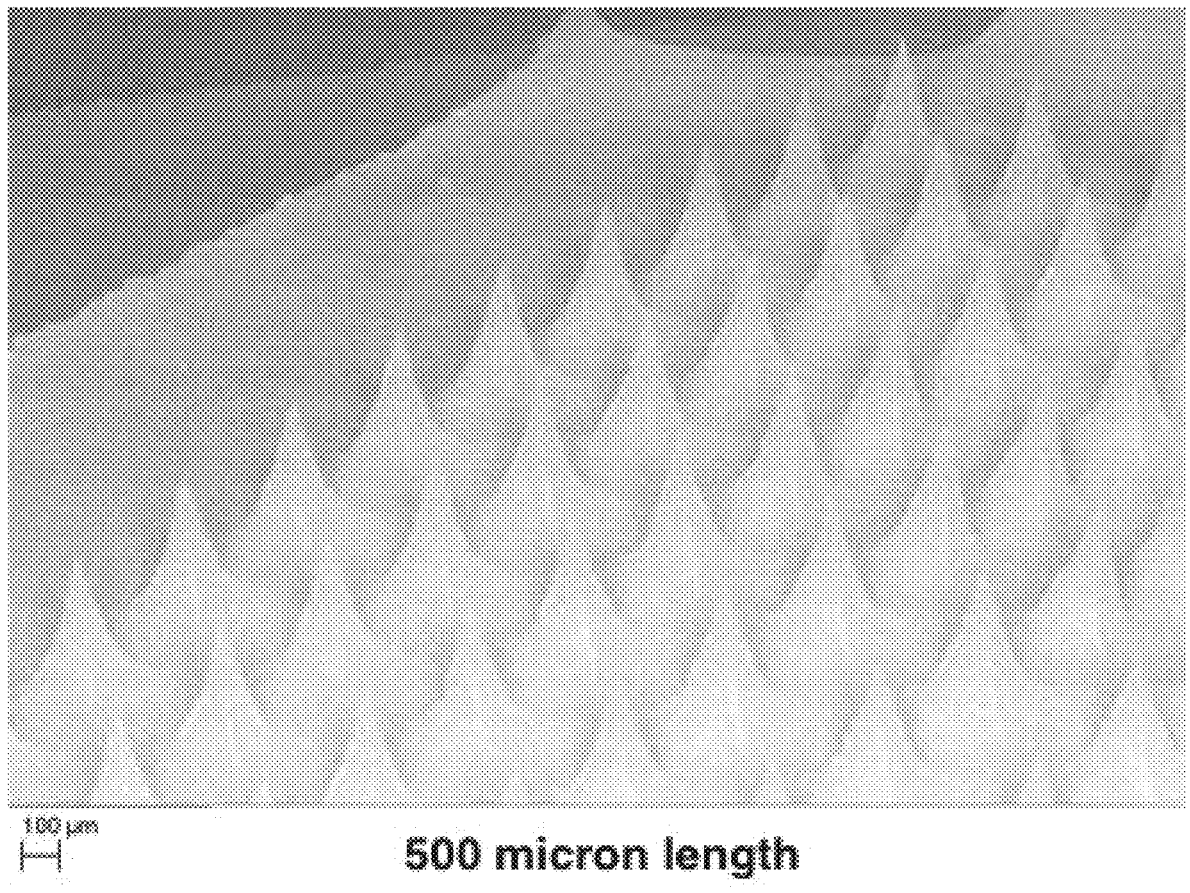
FIG. 4 is an image from a scanning electron micrograph of a microneedle patch with microneedles of 500 microns in length.
Figure 5:
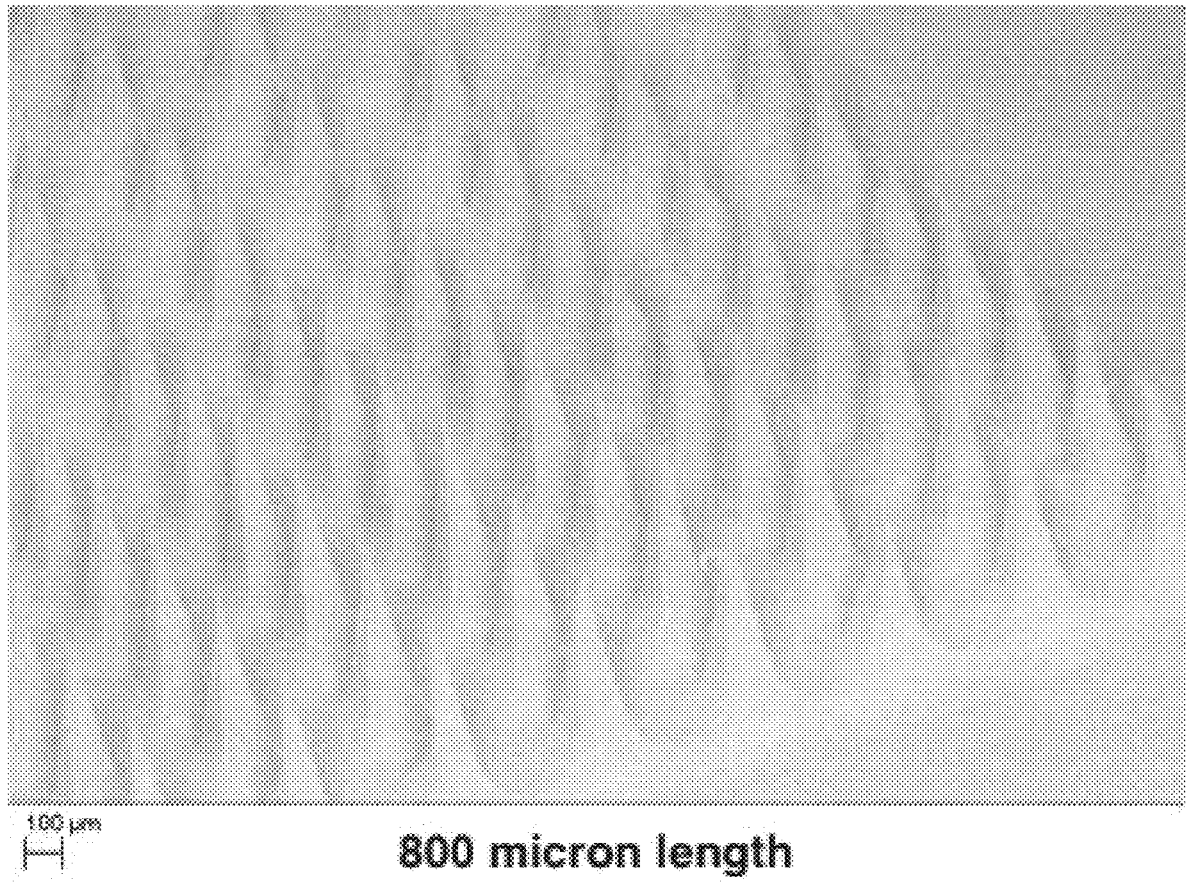
FIG. 5 is an image from a scanning electron micrograph of a microneedle patch with microneedles of 800 microns in length.
Figure 6:
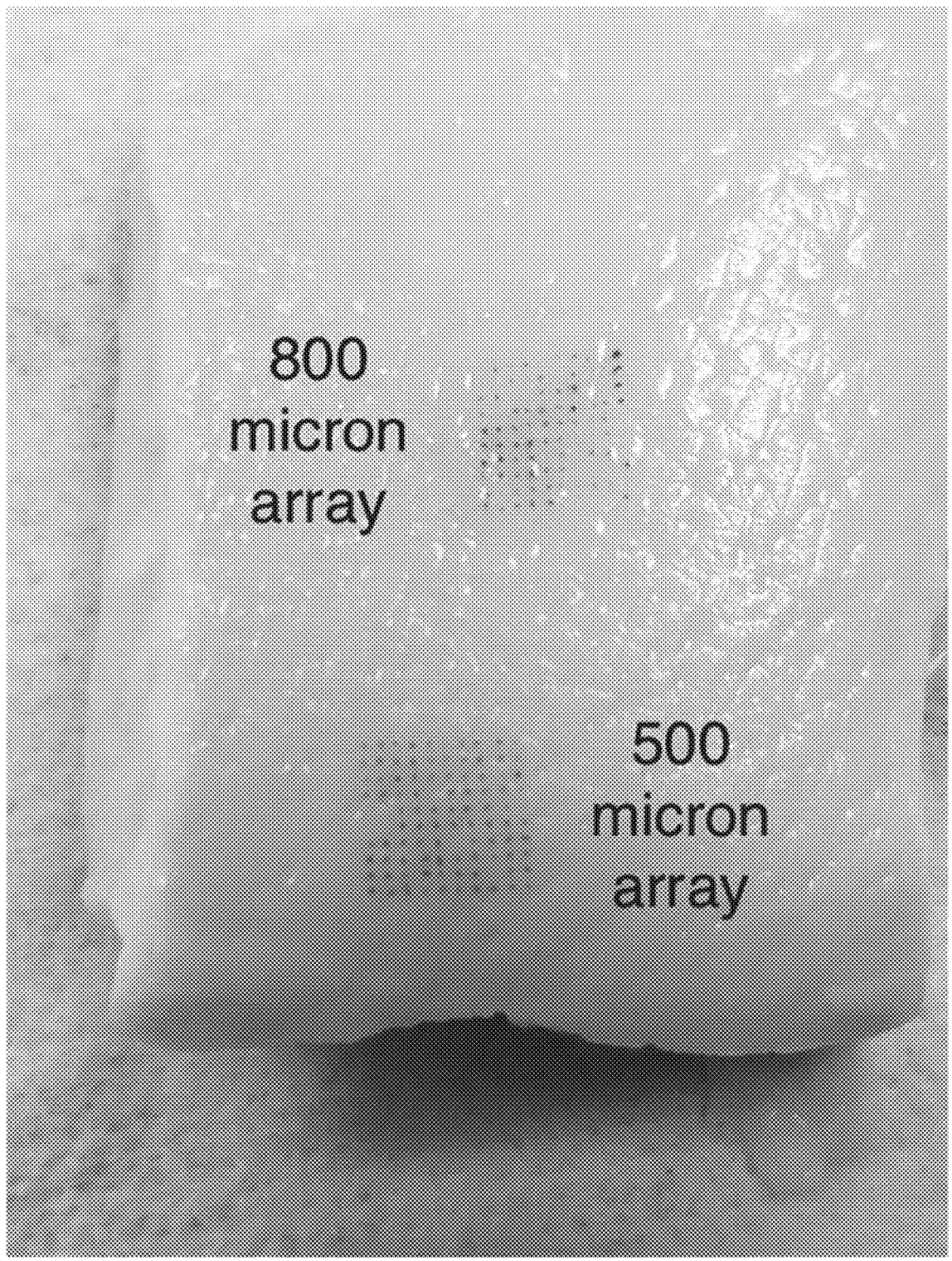
FIG. 6 is an image of porcine skin, as seen from the top, after insertion of a microneedle patch containing a blue tissue marking dye.
Figure 7:
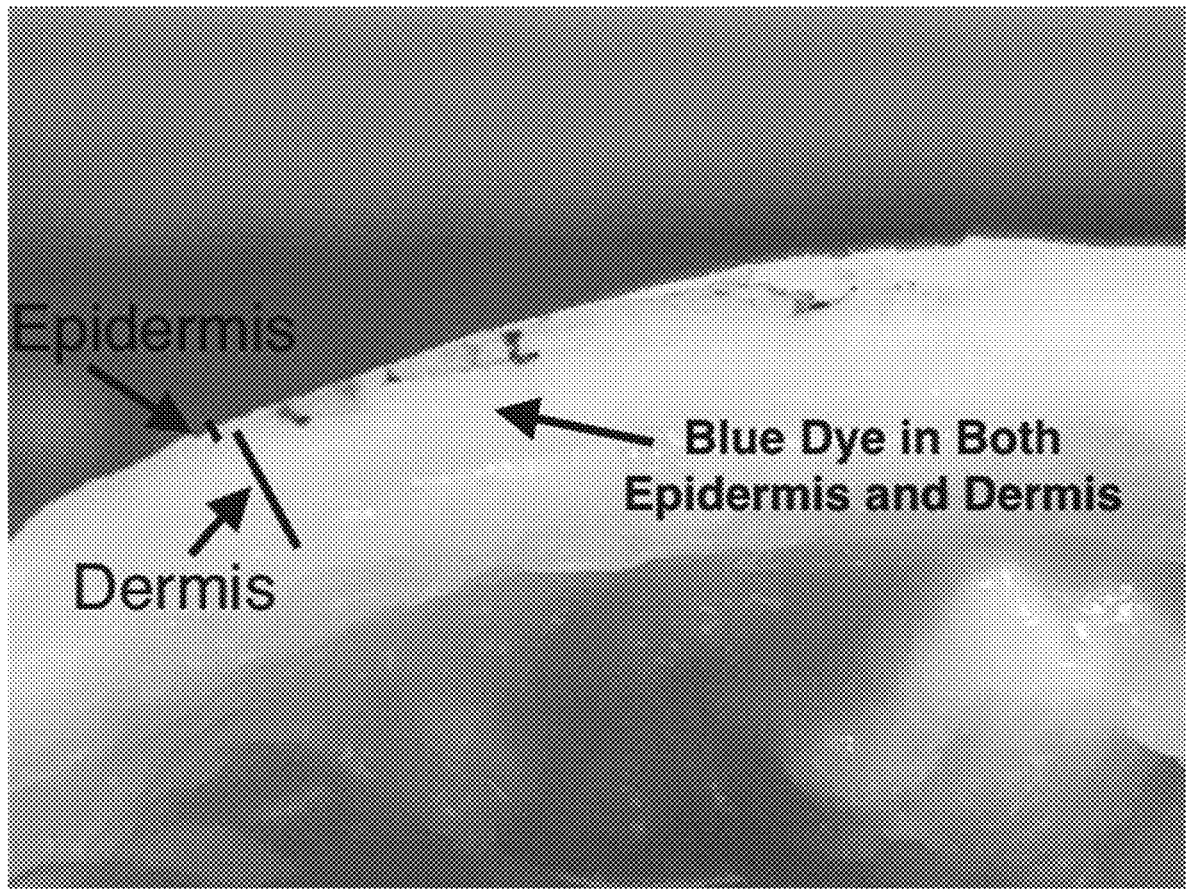
FIG. 7 is an image of porcine skin, as seen from a cross section, after insertion of a microneedle patch containing a blue tissue marking dye.

The microneedle patch comprises conical needles (FIG. 3) to maintain the same volume/dose delivered in both the longer and shorter needles, the shorter needle will have a larger radius compared to the longer needle, where the normal volume of a cone for a given height (h) and radius (r) is as follows: $(h/3)*\pi*r^2$ where, larger needle radius—r1; larger needle height—h1; smaller needle height—h2; smaller needle radius—r2 and the radius of the smaller needle will depend on the heights of both needles and the radius of the larger needle and to calculate the smaller needle radius when the other values are defined, the following equation will be used: $r2=r1*sqrt(h1/h2)$. In microneedle patches where the microneedle patch comprises pyramidal needles to maintain the same volume/dose delivered in both the longer and shorter needles, the shorter needle will have a larger radius compared to the longer needle, and the normal volume of a square-based pyramid for a given base length (L) and height (H) is as follows: $(1/3)*L^2*H$, where larger needle base length—L1, larger needle height—H1, smaller needle height—H2, smaller needle base length—L2, and the base length of the smaller needle will depend on the heights of both needles and the base length of the larger needle and to calculate the smaller needle radius when the other values are defined, the following equation will be used: $L2=L1*sqrt(H1/H2)$.

Example 3

Glycerin Removal from *Candida* Antigen

Figure 8:
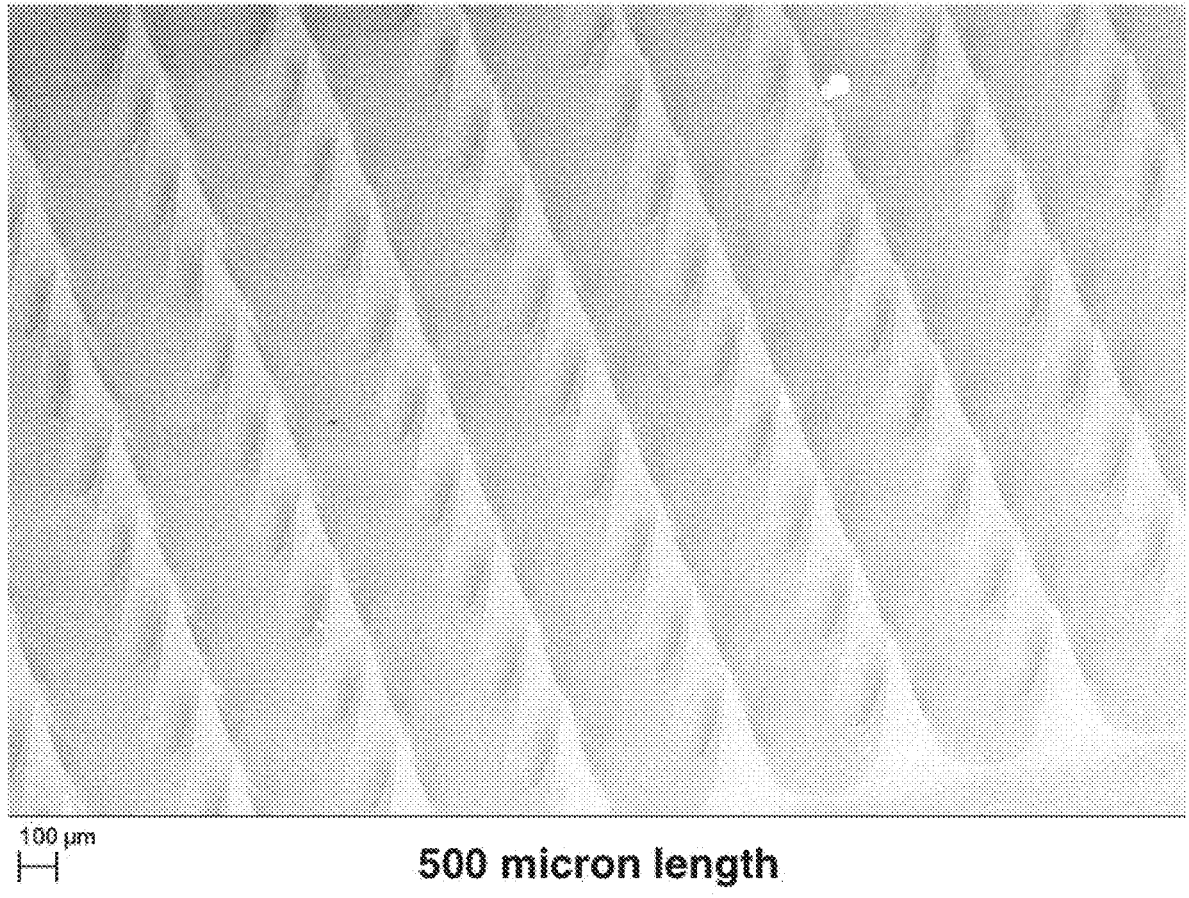
FIG. 8 is an image from a scanning electron micrograph of a microneedle patch comprising immediate release biodegradable polymer microneedles of 500 microns in length.
Figure 9:
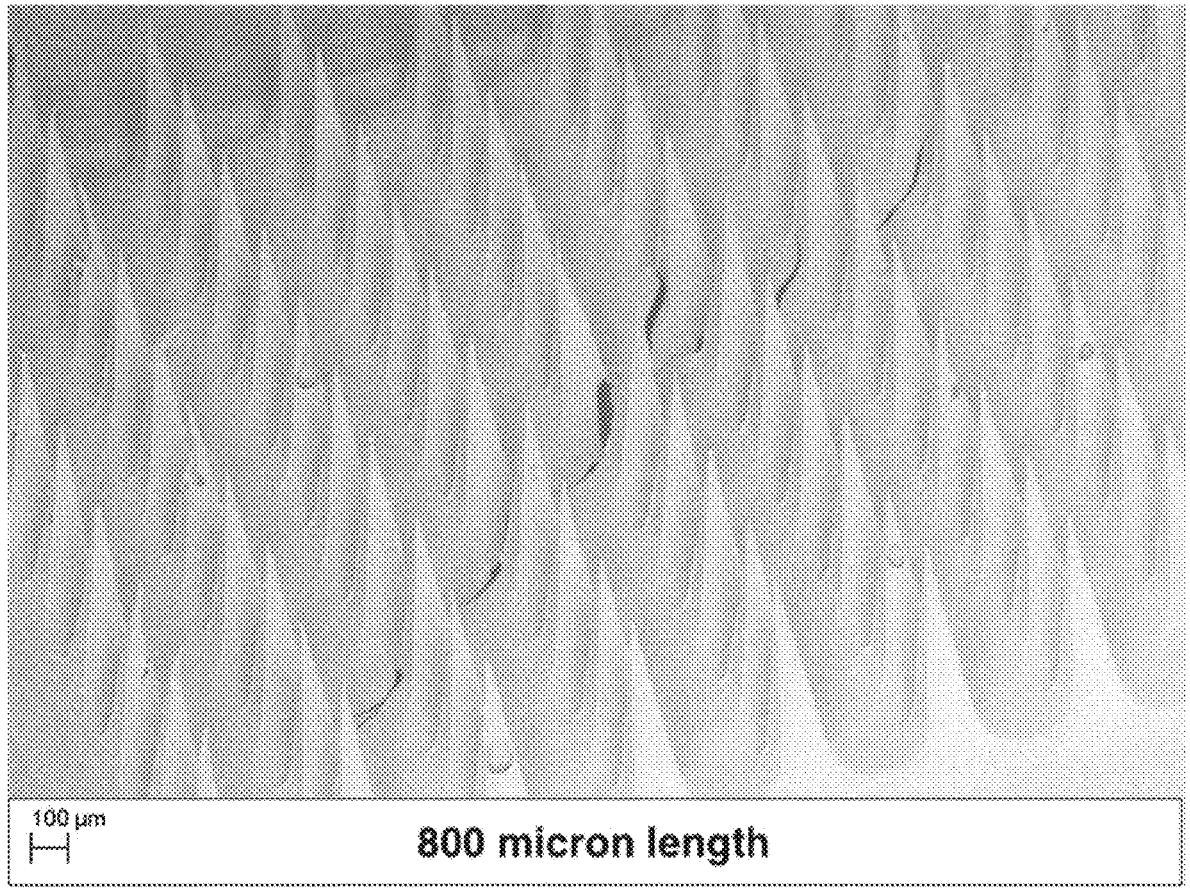
FIG. 9 is an image from a scanning electron micrograph of a microneedle patch comprising immediate release biodegradable polymer microneedles of 800 microns in length.
Figure 10:
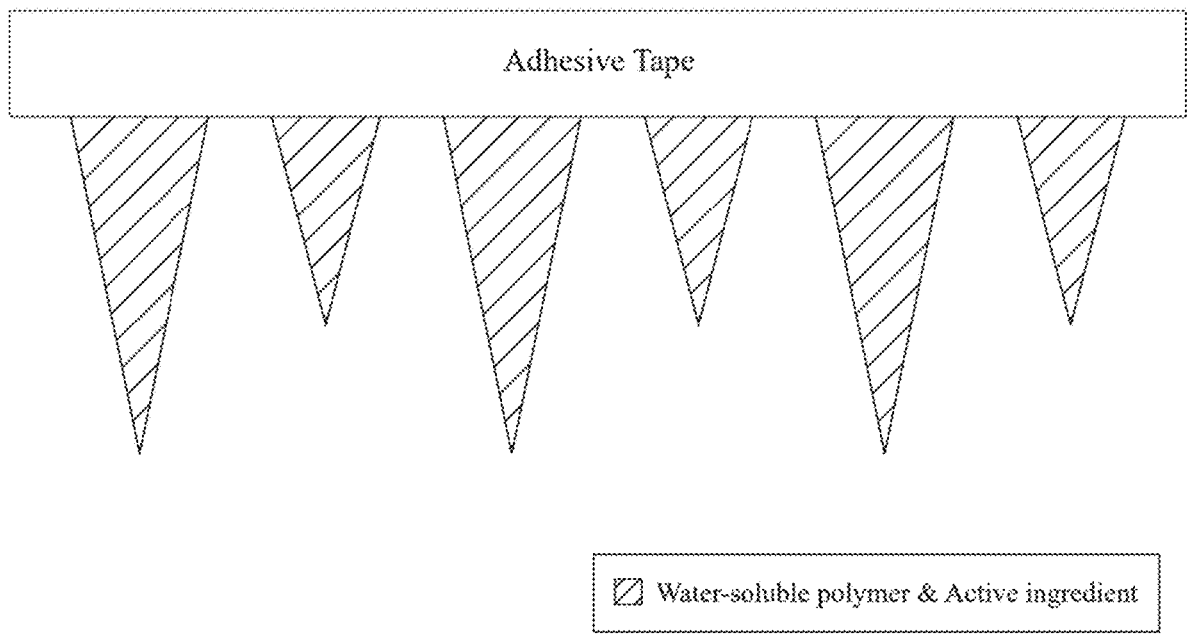
FIG. 10 is an illustration of a microneedle patch as viewed from the side, to show immediate release microneedles of varying lengths and microneedles comprising one or more water soluble polymers and one or more active ingredients.
Figure 11:
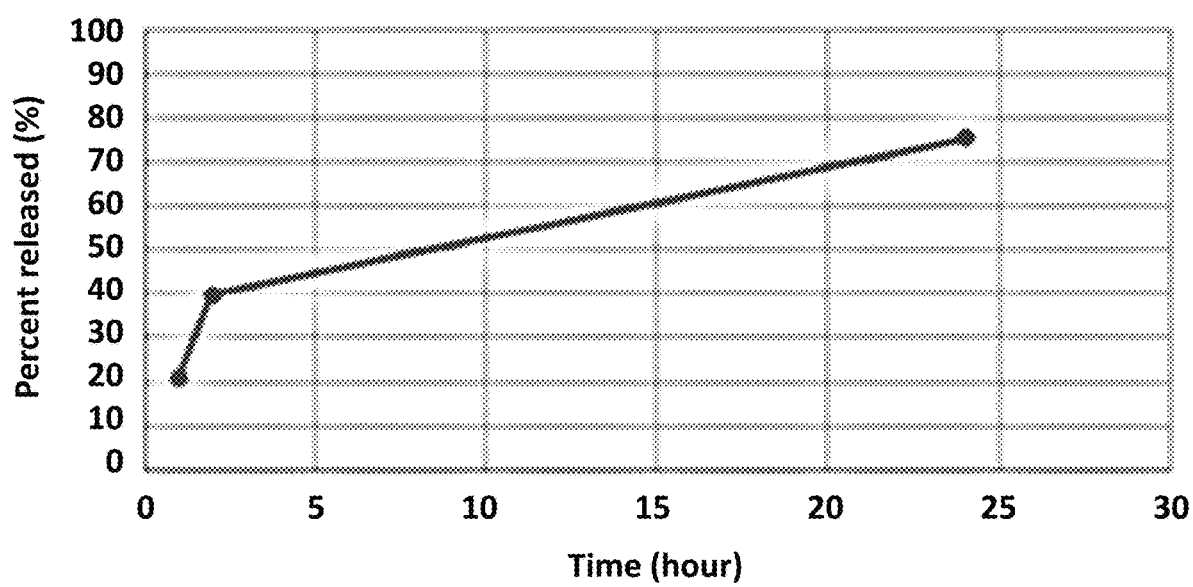
FIG. 11 is a graphical depiction of the release of *Candida* antigen from a microneedle array over a period of 24 hours.
Figure 12:
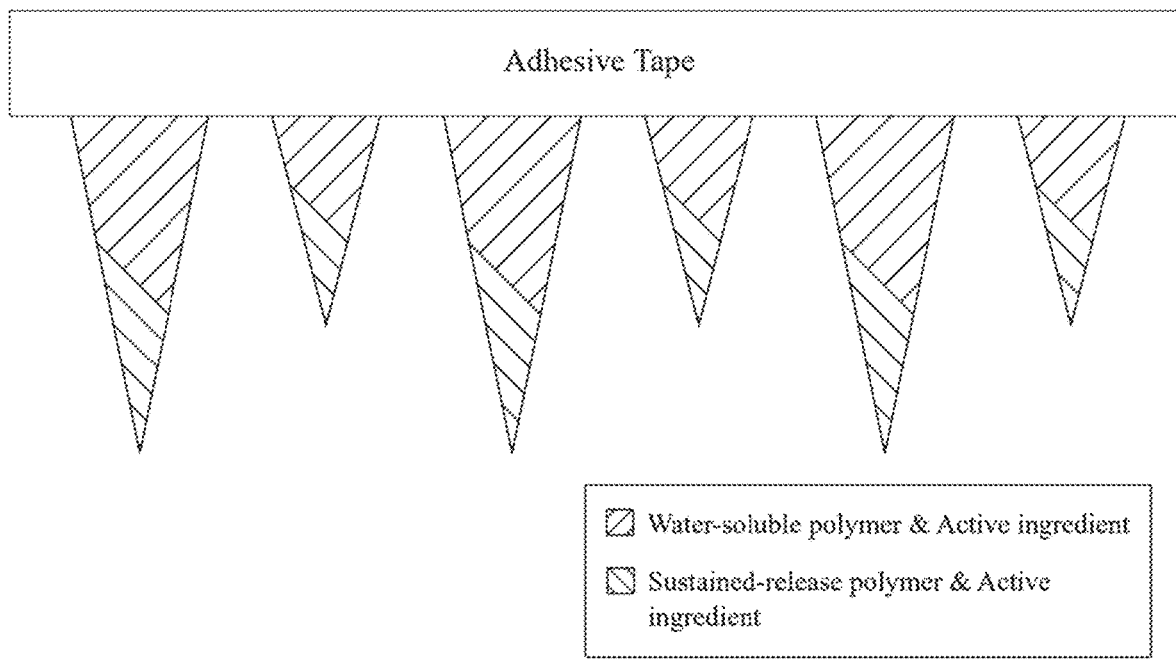
FIG. 12 is an illustration of the microneedle patch as viewed from the side, comprising microneedles of two lengths wherein the microneedles comprise an immediate release, water soluble polymer and one or more therapeutically active ingredients at the base of the microneedle and a sustained release polymer and one or more therapeutically active ingredients at the tip of the microneedle.
Figure 13:
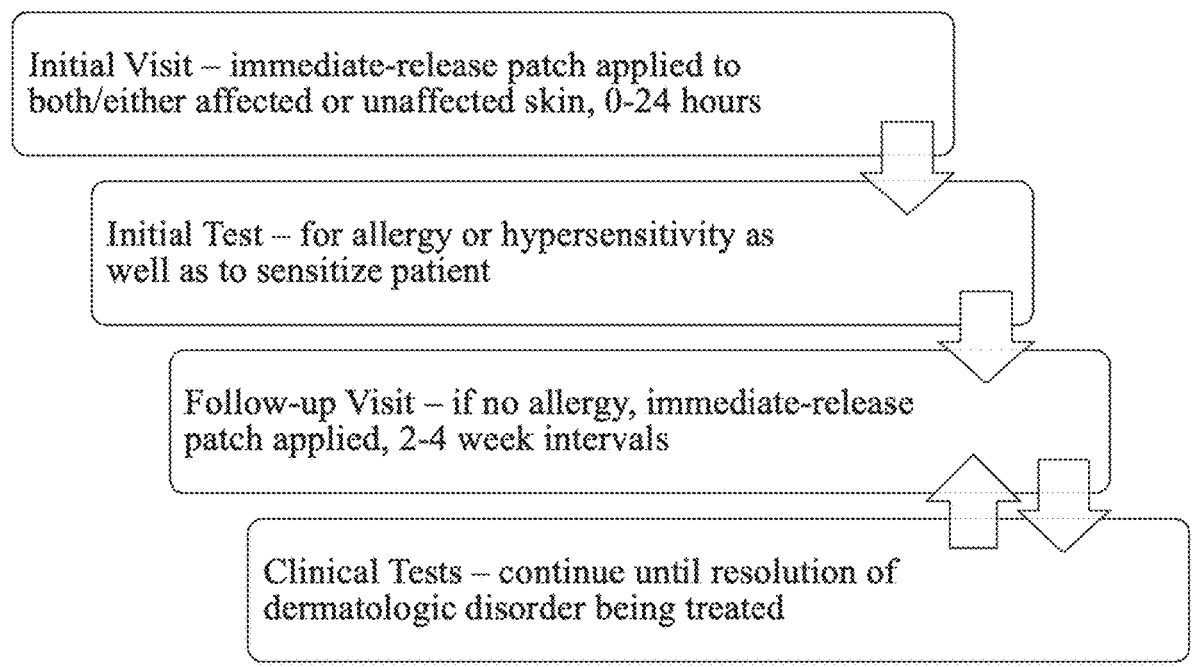
FIG. 13 is a treatment regimen consisting of serial applications of a microneedle patch containing immediate release polymer.
Figure 14:
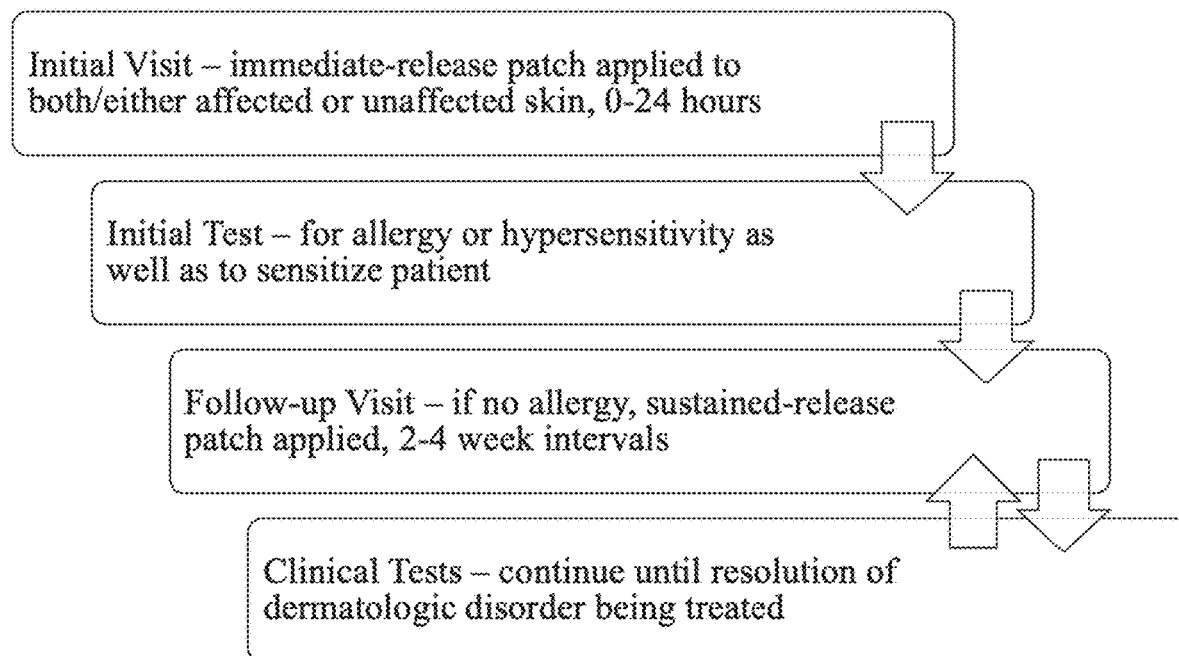
FIG. 14 is a treatment regimen consisting of serial applications of a microneedle patch containing sustained release polymer.

Many commercially available immune stimulating compounds are suspended within a solution containing glycerin. For example, HS Allergy's *Candida* antigen (both the 1:10 w/v and 1:1000 w/v concentrations) contains 50% glycerin by weight. When glycerin containing solutions are mixed with microneedle polymers, precipitation and/or lack of solidification results. For example, precipitation was noted when glycerin-containing *Candida* antigen was mixed with poly lactic-co-glycolic acid (PLGA) 5050 (7-17 k molecular weight, or simply 7-17 k). For example, lack of solidification was noted when glycerin-containing *Candida* antigen was mixed with carboxymethylcellulose (CMC). Therefore, glycerin needs to be removed from immune stimulating compound solutions prior to incorporation with microneedle polymers.

4 g of 1:10 w/v *Candida* antigen solution (HS Allergy) was dialyzed to remove all traces of glycerin from the solution. An 18 g sample remained after dialysis (4.5× dilution). Ultraviolet-visible spectroscopy (UV-Vis) was used to establish the absorbance characteristics of undialyzed *Candida* antigen. Using this UV-Vis method, 36× dilution of the original active ingredient solution and 2× dilution of the dialyzed sample showed similar absorbance, therefore the glycerin-free dialyzed sample was approximately 1/20th of the original concentration.

Example 4

Lyophilized *Candida* Antigen

Certain microneedle polymers, such as PLGA5050 7-17 k, are ideally incorporated with a lyophilized form of active ingredient prior to microneedle molding. The process of lyophilization removes water and results in a powder. Glycerin creates a similar problem as outlined in Example 2 when it comes to lyophilization. When lyophilization was attempted using glycerin-containing 1:10 w/v *Candida* antigen solution (HS Allergy), a viscous liquid was obtained as opposed to a solid. Solid formation is the sign of successful lyophilization. Once glycerin was removed using the dialysis method outlined in Example 3, lyophilization of the dialyzed *Candida* antigen resulted in solid white flakes indicating all water was removed.

Example 5

Carboxymethylcellulose Microneedle Array

The molds from Example 1 were filled with a 2% solution of CMC and allowed to dry before demolding. After demolding, the resultant microneedle arrays were analyzed by scanning electron micrograph. These microneedle arrays were shown to have successfully produced microneedles with dimensions noted in Example 1 (FIG. 4 and FIG. 5).

Example 6

Skin Penetration of Microneedle Array

Microneedle arrays were prepared in a similar fashion to Example 5 with the addition of a blue tissue-marking dye to the CMC solution. After drying, the resultant microneedle arrays were demolded and inserted into porcine skin to assess penetrative strength and ability to deliver active ingredients. The needles were left on the skin for less than 10 minutes after insertion. The porcine skin was then washed with copious amounts of water. After washing, blue dye was visibly apparent at the insertion sites of both the 500 micron and 800 micron microneedle arrays (FIG. 6) indicating successful skin penetration and dissolution. A cross section of the porcine skin showed effective dye delivery into the epidermis and into the superficial dermis (FIG. 7).

Example 7

*Candida* Antigen Microneedle Patch

An immediate release polymer formulation was made using 1 g of the dialyzed sample of *Candida* antigen from Example 3 (representing approximately 50 mg of original undialyzed material) was mixed with approximately 17 g of aqueous CMC. This mixture was then poured into molds from Example 1 to create microneedle arrays. Upon drying and demolding, these microneedle arrays containing approximately 75% payload of 1:10 w/v *Candida* antigen solution were analyzed by scanning electron micrograph.

These microneedle arrays were shown to have successfully produced active-ingredient microneedles with dimensions noted in Example 1 (FIG. 8 and FIG. 9). If these needles were alternated in the same microneedle array, the resulting microneedle array upon insertion into the skin would approximate the appearance of FIG. 10.

Example 8

Immediate and Sustained Release Microneedles

A microneedle patch and composition for the sustained release patch that nonetheless also has an immediate release component as a separate layer. To extend the release of active ingredient, lyophilized *Candida* antigen from Example 4 was mixed with PLGA5050 7-17 k. The resulting mixture was then poured into molds from Example 1 to create microneedle arrays. Upon drying and demolding, these microneedle arrays were then analyzed for in-vitro release using the UV-Vis assay from Example 3. The microneedle arrays were placed in deionized water at 32 degrees Celsius. *Candida* antigen was shown to release consistently (but no more than 75% total release) from the microneedle over a period of 24 hours with anticipated full release consistently over 2 days based on release kinetics (FIG. 11).

An additional layer of active ingredient and polymer mixture from Example 7 could be poured overlying the microneedle array from this Example prior to demolding to create a sustained-release microneedle tip and quick-dissolving water-soluble microneedle base (FIG. 12). Upon skin insertion, the water-soluble polymer layer would quickly dissolve and release the sustained-release polymer layer into the skin. The adhesive backing could then be removed within minutes but allow for release of active ingredient for days as demonstrated in the release kinetics of FIG. 11.

Example 9

Use of Microneedle Array for Treatment Pretesting

Given the immune stimulating nature of the microneedle arrays described in the prior Examples, treating a patient first with a sustained-release version of the active ingredient without prior pre-testing with an immediate-release formulation may lead to serious or life-threatening reactions if the patient is allergic to the active ingredient being delivered in a continuous manner over the course of days. Pre-testing with an immediate-release patch as a first test in all patients is necessary to prevent complications as well as to sensitize the patient's immune system to the immune stimulating compounds. Therefore, patients may be treated with either a treatment regimen consisting of serial applications of the microneedle array of FIG. 10 (regimen seen in FIG. 13) or an initial application of the microneedle array of FIG. 10 followed by serial application of the microneedle array of FIG. 12 (regimen in FIG. 14).

Example 10

Immediate Release Microneedles

FIG. 10, such a microneedle patch and composition is for the immediate release patch as used for pre-testing the patient for allergy/hypersensitivity testing as well as for sensitization of the patient to the therapeutically active ingredient before moving onto the sustained release patch for therapeutic application against the dermatological disorder being targeted by the local immune stimulation triggered by active therapeutic molecule so tested. The immediate release patch is usually applied for 0-24 hours of active ingredient delivery and testing.

Example 11

Glycerin Removal

To remove glycerin from a glycerin-containing immune stimulating compound solution, the solution containing glycerin was added to a dialysis device with built-in dialysis membrane (Repligen (Waltham, MA, USA) Float-A-Lyzer G2 Dialysis Device, Biotech Cellulose Ester membrane, 10 mL, 0.1 to 0.5 kD). The dialysis device was soaked in deionized water with gentle stirring at ambient temperature for 2-4 hours. The deionized water was then exchanged for the same volume of new deionized water, and the device was left to soak with gentle stirring at ambient temperature for an additional 12-24 hours. During this process, glycerin diffused from the dialysis device into the surrounding deionized water. After the total process of soaking in deionized water above, the dialysis device was removed from the deionized water, and the sample within contained a glycerin-free solution of immune-stimulating compound. This processed solution can then be incorporated directly with a water-soluble polymer, lyophilized and incorporated with a water-soluble polymer, or it can then be resuspended and incorporated with a water-soluble polymer.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Instead, this application is intended to cover any variations, uses, or adaptations of the present teachings and use its general principles. Further, this application is intended to cover such departures from the present disclosure as come within known or customary practice in the art to which these teachings pertain. Many modifications and variations can be made to the particular embodiments described without departing from the spirit and scope of the present disclosure, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A dissolvable microneedle patch for delivery of a therapeutically active ingredient to skin comprising:
a plurality of microneedles and a removable substrate;
wherein the plurality of microneedles are attached to the removable substrate;
wherein the plurality of microneedles comprise a tapered tip that extends away from the removable substrate;
wherein the plurality of microneedles comprise a biodegradable polymer and a therapeutically active ingredient dispersed in the biodegradable polymer; and
wherein the therapeutically active ingredient is an immunogenic stimulator selected from the group consisting of *Candida* antigen, *trichophyton* antigen, and tuberculin; and
wherein the immunogenic stimulator is substantially free of glycerin.

2. The dissolvable microneedle patch of claim 1, wherein the plurality of microneedles can range from about 10 microns to about 1000 microns in length.

3. The dissolvable microneedle patch of claim 1, wherein the plurality of microneedles each comprise about equal amounts of the therapeutically active ingredient.

4. The dissolvable microneedle patch of claim 1, wherein the plurality of microneedles each comprise unequal amount of the therapeutically active ingredient.

5. The dissolvable microneedle patch of claim 1, wherein the *Candida* antigen is lyophilized.

6. The dissolvable microneedle patch of claim 1, wherein the dissolvable microneedle patch comprises at least about 1 to about 200 microneedles per square centimeter.

7. The dissolvable microneedle patch of claim 1, wherein the dissolvable microneedle patch ranges from about 0.1 to about 1000 square centimeters and may be trimmed to fit any shape necessary to accommodate any surface of topology of human skin.

8. The dissolvable microneedle patch of claim 1, wherein the plurality of microneedles are configured to have a sustained release of therapeutically active ingredient into the skin.

9. The dissolvable microneedle patch of claim 8, is configured to release the therapeutically active ingredient from about 1 day to about 30 days after application of the dissolvable microneedle patch into the skin.

10. The dissolvable microneedle patch of claim 1, wherein the plurality of microneedles are configured to have an immediate release of therapeutically active ingredient into the skin.

11. The dissolvable microneedle patch of claim 10, wherein the plurality of microneedles are configured to release the therapeutically active ingredient from about 0 hours to about 24 hours after application of the dissolvable microneedle patch into the skin.

12. The dissolvable microneedle patch of claim 1, wherein the plurality of microneedles are configured to have both sustained release and an immediate release of therapeutically active ingredient into the skin.

13. The dissolvable microneedle patch of claim 1, wherein the plurality of microneedles are spatially separated within the skin where one microneedle does not touch another microneedle.

14. The dissolvable microneedle patch of claim 1, wherein the tapered tip constitutes about 5% to about 99% of a total volume of the plurality of microneedles.

15. The dissolvable microneedle patch of claim 1, wherein the removable substrate comprises a therapeutically active ingredient dispersed in a polymer.

16. The dissolvable microneedle patch of claim 1, wherein the removable substrate comprises an adhesive medical tape.

17. The dissolvable microneedle patch of claim 1, wherein the dissolvable microneedle patch administers to a subject in need thereof a therapeutically effective amount of the immunogenic stimulator.

18. The dissolvable microneedle patch of claim 1, wherein the therapeutically active ingredient stimulates a local immune response.

19. A method of treating a skin condition comprising:
applying a dissolvable microneedle patch for delivery of a therapeutically active ingredient to skin comprising:
a plurality of microneedles and a removable substrate;
wherein the plurality of microneedles are attached to the removable substrate;
wherein the plurality of microneedles comprise a tapered tip that extends away from the removable substrate;
wherein the plurality of microneedles comprise a biodegradable polymer and a therapeutically active ingredient dispersed in the biodegradable polymer;
wherein the therapeutically active ingredient is an immunogenic stimulator selected from the group consisting of *Candida* antigen, *trichophyton* antigen, and tuberculin; and
wherein the immunogenic stimulator is substantially free of glycerin;
exerting sufficient force on the dissolvable microneedle patch to permit the plurality of microneedles to penetrate to a location selected from the group consisting of epidermis, dermis, and papillary dermis;
allowing the plurality of microneedles to remain in the skin until the biodegradable polymer degrades; and
removing an adhesive substrate from the dissolvable microneedle patch.

20. The method of claim 19, wherein at least 90% of the plurality of microneedles detach from the removable substrate within about 20 minutes after application of the dissolvable microneedle patch.

21. The method of claim 19, wherein at least 90% of the plurality of microneedles detach from the adhesive substrate of the removable substrate upon removal of the removable substrate within a period of 5 minutes.

22. The method of claim 19, wherein the biodegradable polymer degrades and releases therapeutically active ingredient into the skin.

23. The method of claim 19, wherein the biodegradable polymer degrades and releases therapeutically active ingredient into the skin over a period of about 1 day to about 30 days.

24. The method of claim 19, wherein the biodegradable polymer degrades and releases therapeutically active ingredient into the skin over a period of about 2 days to about 21 days.

25. The method of claim 19, wherein the sufficient force is applied to the skin by a finger.

26. The method of claim 25, wherein the sufficient force applied to the skin ranges from 0N to about 1000N.

27. The method of claim 25, wherein the sufficient force applied to the skin is 10N.

28. The method of claim 19, wherein the sufficient force is applied by impact insertion using an applicator device.

29. The method of claim 28, wherein the sufficient force applied to the skin ranges from 0N to about 1000N.

30. The method of claim 28, wherein the sufficient force applied to the skin is 10N.

\* \* \* \* \*